United States Patent
Zagar et al.

(10) Patent No.: US 6,482,774 B1
(45) Date of Patent: Nov. 19, 2002

(54) SUBSTITUTED (4-BROMPYRAZOLE-3-YL) BENZAZOLES

(75) Inventors: Cyrill Zagar, Ludwigshafen (DE); Gerhard Hamprecht, Weinheim (DE); Markus Menges, Bensheim (DE); Olaf Menke, Altleiningen (DE); Robert Reinhard, Ludwigshafen (DE); Peter Schäfer, Ottersheim (DE); Karl-Otto Westphalen, Speyer (DE); Martina Otten, Ludwigshafen (DE); Helmut Walter, Obrigheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/673,996

(22) PCT Filed: Apr. 22, 1999

(86) PCT No.: PCT/EP99/02699
§ 371 (c)(1),
(2), (4) Date: Oct. 25, 2000

(87) PCT Pub. No.: WO99/55702
PCT Pub. Date: Nov. 4, 1999

(30) Foreign Application Priority Data

Apr. 29, 1998 (DE) .......................... 198 19 060

(51) Int. Cl.⁷ .................... C07D 417/04; C07D 413/04; C07F 9/6541; A01N 43/78; A01N 43/76
(52) U.S. Cl. ................... 504/267; 504/270; 504/280; 548/217; 548/166; 548/377.1
(58) Field of Search ................... 548/217, 166, 548/377.1; 504/270, 267, 280

(56) References Cited

U.S. PATENT DOCUMENTS 6,232,407 B1 * 5/2001 Zagar et al. ............... 548/217

FOREIGN PATENT DOCUMENTS

| WO | WO 92/06962 | 4/1992 |
| WO | WO 96/15115 | 5/1996 |
| WO | WO 96/15116 | 5/1996 |
| WO | WO 98/27090 | 6/1998 |

OTHER PUBLICATIONS

U.S. patent application Ser. No. 09/331,065, Zager et al., filed Jun. 16, 1999.

* cited by examiner

Primary Examiner—Mukund J. Shah
Assistant Examiner—Hong Liu
(74) Attorney, Agent, or Firm—Keil & Weinkauf

(57) ABSTRACT

Substituted (4-bromopyrazol-3-yl)benzazoles I

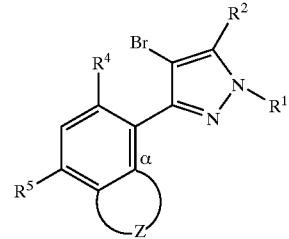

and their salts where $R^1$=H, $C_1$–$C_4$-alkyl, $C_1$–$C_4$-haloalkyl;

$R^2$=CN, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfinyl, $C_1$–$C_4$-haloalkylsulfinyl, $C_1$–$C_4$-alkylsulfonyl, $C_1$–$C_4$-haloalkylsulfonyl;

$R^4$=H, halogen;

$R^5$=H, CN, halogen, $C_1$–$C_4$-alkyl, $C_1$–$C_4$-haloalkyl, $C_1$–$C_4$-alkoxy or $C_1$–$C_4$-haloalkoxy;

Z=—N=C($XR^6$)—O— or —N=C($XR^6$)—S—, attached to α via the nitrogen, oxygen or sulfur;

X=a chemical bond, oxygen, sulfur, —S(O)—, —$SO_2$—, —NH— or —N($R^7$)—;

$R^6$, $R^7$=$C_1$–$C_6$-alkyl, $C_1$–$C_6$-haloalkyl, cyano-$C_1$–$C_4$-alkyl, hydroxy-$C_1$–$C_4$-alkyl, $C_3$–$C_6$-alkenyl, cyano-$C_3$–$C_6$-alkenyl, $C_3$–$C_6$-haloalkenyl, $C_3$–$C_6$-alkynyl, cyano-$C_3$–$C_6$-alkynyl, $C_3$–$C_6$-haloalkynyl, $C_1$–$C_4$-alkoxy-$C_1$–$C_4$-alkyl, $C_1$–$C_4$-haloalkoxy-$C_1$–$C_4$-alkyl, $C_3$–$C_4$-alkenyloxy-$C_1$–$C_4$-alkyl, $C_3$–$C_4$-alkynyloxy-$C_1$–$C_4$-alkyl, $C_3$–$C_8$-cycloalkyloxy-$C_1$–$C_4$-alkyl, amino-$C_1$–$C_4$-alkyl, $C_1$–$C_4$-alkylamino-$C_1$–$C_4$-alkyl, di($C_1$–$C_4$-alkyl)amino-$C_1$–$C_4$-alkyl, $C_1$–$C_4$-alkylthio-$C_1$–$C_4$-alkyl, $C_1$–$C_4$-haloalkylthio-$C_1$–$C_4$-alkyl, $C_3$–$C_4$-alkenylthio-$C_1$–$C_4$-alkyl, $C_3$–$C_4$-alkynylthio-$C_1$–$C_4$-alkyl, $C_1$–$C_4$-alkylsulfinyl-$C_1$–$C_4$-alkyl, $C_1$–$C_4$-haloalkylsulfinyl-$C_1$–$C_4$-alkyl, $C_3$–$C_4$-alkenylsulfinyl-$C_1$–$C_4$-alkyl, $C_3$–$C_4$-alkynylsulfinyl-$C_1$–$C_4$-alkyl, $C_1$–$C_4$-alkylsulfonyl-$C_1$–$C_4$-alkyl, $C_1$–$C_4$-haloalkylsulfonyl-$C_1$–$C_4$-alkyl, $C_3$–$C_4$-alkenylsulfonyl-$C_1$–$C_4$-alkyl, $C_3$–$C_4$-alkynylsulfonyl-$C_1$–$C_4$-alkyl, hydroxycarbonyl-$C_1$–$C_4$-alkyl, $C_1$–$C_4$-alkoxycarbonyl-$C_1$–$C_4$-alkyl, which may carry a CN or $C_1$–$C_4$-alkoxycarbonyl group, $C_1$–$C_4$-alkylthiocarbonyl-$C_1$–$C_4$-alkyl, aminocarbonyl-$C_1$–$C_4$-alkyl, $C_1$–$C_4$-alkylaminocarbonyl-$C_1$–$C_4$-alkyl, di($C_1$–$C_4$-alkyl)aminocarbonyl-$C_1$–$C_4$-alkyl, di($C_1$–$C_4$-alkyl)-phosphonyl-$C_1$–$C_4$-alkyl, $C_1$–$C_4$-alkoxyimino-$C_1$–$C_4$-alkyl, $C_3$–$C_4$-alkenyloxyimino-$C_1$–$C_4$-alkyl, unsubstituted or substituted $C_3$–$C_8$-cycloalkyl, $C_3$–$C_8$-cycloalkyl-$C_1$–$C_4$-alkyl, phenyl, phenyl-$C_1$–$C_4$-alkyl, 3- to 7-membered heterocyclyl or heterocyclyl-$C_1$–$C_4$-alkyl, where each cycloalkyl and each heterocyclyl ring may contain a CO or CS ring member;

if X=a chemical bond, —O—, —S—, —NH— or —N($R^7$)—, $R^6$ may also be $C_1$–$C_4$-alkylcarbonyl, $C_1$–$C_4$-haloalkylcarbonyl, $C_1$–$C_4$-alkoxycarbonyl, $C_1$–$C_4$-alkylsulfonyl or $C_1$–$C_4$-haloalkylsulfonyl;

if X=a chemical bond, $R^6$ may furthermore be CN, SH, $NH_2$, halogen, $-CH_2-CH(halogen)-R^8$, $-CH=CH-R^8$ or $-CH=C(halogen)-R^8$, where $R^8$=COOH, $C_1-C_4$-alkoxycarbonyl, $C_1-C_4$-alkylthiocarbonyl, $CONH_2$, $C_1-C_4$-alkylaminocarbonyl, di($C_1-C_4$-alkyl)aminocarbonyl or di($C_1-C_4$-alkyl)phosphonyl;

or $R^6+R^7$=an unsubstituted or substituted 1,3-propylene, tetramethylene, pentamethylene or ethyleneoxyethylene chain.

Use: As herbicides; for the desiccation/defoliation of plants.

17 Claims, No Drawings

SUBSTITUTED (4-BROMPYRAZOLE-3-YL) BENZAZOLES

The present invention relates to novel substituted (4-bromopyrazol-3-yl)benzazoles of the formula I

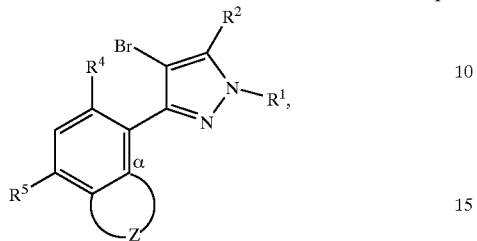

where:
- $R^1$ is hydrogen, $C_1$–$C_4$-alkyl or $C_1$–$C_4$-haloalkyl;
- $R^2$ is cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfinyl, $C_1$–$C_4$-haloalkylsulfinyl, $C_1$–$C_4$-alkylsulfonyl or $C_1$–$C_4$-haloalkylsulfonyl;
- $R^4$ is hydrogen or halogen;
- $R^5$ is hydrogen, halogen, cyano, $C_1$–$C_4$-alkyl, $C_1$–$C_4$-haloalkyl, $C_1$–$C_4$-alkoxy or $C_1$–$C_4$-haloalkoxy;
- Z is a group —N=C($XR^6$)—O— or —N=C($XR^6$)—S— which may be attached to α via the nitrogen, oxygen or sulfur;
- X is a chemical bond, oxygen, sulfur, —S(O)—, —$SO_2$—, —NH— or —N($R^7$)—;
- $R^6$, $R^7$ independently of one another are each $C_1$–$C_6$-alkyl, $C_1$–$C_6$-haloalkyl, cyano-$C_1$–$C_4$-alkyl, hydroxy-$C_1$–$C_4$-alkyl, $C_3$–$C_6$-alkenyl, cyano-$C_3$–$C_6$-alkenyl, $C_3$–$C_6$-haloalkenyl, $C_3$–$C_6$-alkynyl, cyano-$C_3$–$C_6$-alkynyl, $C_3$–$C_6$-haloalkynyl, $C_1$–$C_4$-alkoxy-$C_1$–$C_4$-alkyl, $C_1$–$C_4$-haloalkoxy-$C_1$–$C_4$-alkyl, $C_3$–$C_4$-alkenyloxy-$C_1$–$C_4$-alkyl, $C_3$–$C_4$-alkynyloxy-$C_1$–$C_4$-alkyl, $C_3$–$C_8$-cycloalkyloxy-$C_1$–$C_4$-alkyl, amino-$C_1$–$C_4$-alkyl, $C_1$–$C_4$-alkylamino-$C_1$–$C_4$-alkyl, di($C_1$–$C_4$-alkyl)amino-$C_1$–$C_4$-alkyl, $C_1$–$C_4$-alkylthio-$C_1$–$C_4$-alkyl, $C_1$–$C_4$-haloalkylthio-$C_1$–$C_4$-alkyl, $C_3$–$C_4$-alkenylthio-$C_1$–$C_4$-alkyl, $C_3$–$C_4$-alkynylthio-$C_1$–$C_4$-alkyl, $C_1$–$C_4$-alkyl sulfinyl-$C_1$–$C_4$-alkyl, $C_1$–$C_4$-haloalkylsulfinyl-$C_1$–$C_4$-alkyl, $C_3$–$C_4$-alkenylsulfinyl-$C_1$–$C_4$-alkyl, $C_3$–$C_4$-alkynylsulfinyl-$C_1$–$C_4$-alkyl, $C_1$–$C_4$-alkylsulfonyl-$C_1$–$C_4$-alkyl, $C_1$–$C_4$-haloalkylsulfonyl-$C_1$–$C_4$-alkyl, $C_3$–$C_4$-alkenylsulfonyl-$C_1$–$C_4$-alkyl, $C_3$–$C_4$-alkynylsulfonyl-$C_1$–$C_4$-alkyl, hydroxycarbonyl-$C_1$–$C_4$-alkyl, ($C_1$–$C_4$-alkoxy)carbonyl-$C_1$–$C_4$-alkyl, which may carry a cyano or ($C_1$–$C_4$-alkoxy)carbonyl group, ($C_1$–$C_4$-alkylthio)carbonyl-$C_1$–$C_4$-alkyl, aminocarbonyl-$C_1$–$C_4$-alkyl, $C_1$–$C_4$-alkylaminocarbonyl-$C_1$–$C_4$-alkyl, di($C_1$–$C_4$-alkyl)aminocarbonyl-$C_1$–$C_4$-alkyl, di($C_1$–$C_4$-alkyl)-phosphonyl-$C_1$–$C_4$-alkyl, ($C_1$–$C_4$-alkoxy)imino-$C_1$–$C_4$-alkyl, ($C_3$–$C_4$-alkenyloxy)imino-$C_1$–$C_4$-alkyl, $C_3$–$C_8$-cycloalkyl, $C_3$–$C_8$-cycloalkyl-$C_1$–$C_4$-alkyl, phenyl, phenyl-$C_1$–$C_4$-alkyl, 3- to 7-membered heterocyclyl or heterocyclyl-$C_1$–$C_4$-alkyl, where each cycloalkyl and each heterocyclyl ring may contain a carbonyl or thiocarbonyl ring member, and where each cycloalkyl, phenyl and heterocyclyl ring may be unsubstituted or may carry from one to four substituents, in each case selected from the group consisting of cyano, nitro, amino, hydroxyl, carboxyl, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl, ($C_1$–$C_4$-alkoxy)carbonyl, ($C_1$–$C_4$-alkyl)carbonyl, ($C_1$–$C_4$-haloalkyl)carbonyl, ($C_1$–$C_4$-alkyl)carbonyloxy, ($C_1$–$C_4$-haloalkyl)carbonyloxy and di($C_1$–$C_4$-alkyl)amino;
- if x is a chemical bond, oxygen, sulfur, —NH— or —N($R^7$)—, $R^6$ may also be ($C_1$–$C_4$-alkyl)carbonyl, ($C_1$–$C_4$-haloalkyl)carbonyl, ($C_1$–$C_4$-alkoxy)carbonyl, $C_1$–$C_4$-alkylsulfonyl or $C_1$–$C_4$-haloalkylsulfonyl;
- if X is a chemical bond, $R^6$ may furthermore be hydrogen, cyano, mercapto, amino, halogen, —$CH_2$—CH(halogen)-$R^8$, —CH=CH—$R^8$ or —CH=C(halogen)-$R^8$, where $R^8$ is hydroxycarbonyl, ($C_1$–$C_4$-alkoxy)carbonyl, ($C_1$–$C_4$-alkylthio)carbonyl, aminocarbonyl, $C_1$–$C_4$-alkylaminocarbonyl, di($C_1$–$C_4$-alkyl)aminocarbonyl or di($C_1$–$C_4$-alkyl)phosphonyl;
- or $R^6$ and $R^7$ together are a 1,3-propylene, tetramethylene, pentamethylene or ethyleneoxyethylene chain which may in each case be unsubstituted or may carry from 1 to 4 $C_1$–$C_4$-alkyl groups or one or two ($C_1$–$C_4$-alkoxy)carbonyl groups, and the agriculturally useful salts of these compounds I.

Furthermore, the invention relates to
- the use of the compounds I as herbicides and/or for the desiccation and/or defoliation of plants,
- herbicidal compositions and compositions for the desiccation and/or defoliation of plants which comprise the compounds I as active ingredients,
- processes for preparing the compounds I and herbicidal compositions and compositions for the desiccation/defoliation of plants using the compounds I,
- methods for controlling undesirable vegetation and for the desiccation and/or defoliation of plants using the compounds I, and also
- novel intermediates of the formulae Va and Vb.

The present (4-bromopyrazol-3-yl)benzazoles I are covered by the general formula of active compounds which form part of the subject matter of the earlier application DE-A 19 652 240.

It is an object of the present invention to provide novel herbicidally active pyrazole compounds which allow better selective control of undesirable plants than the compounds of the prior art. It is a further object to provide novel compounds which have a desiccant/defoliant action.

We have found that these objects are achieved by the present substituted (4-bromopyrazol-3-yl)benzazoles of the formula I.

Furthermore, we have found herbicidal compositions which comprise the compounds I and have very good herbicidal activity. Moreover, we have found processes for preparing these compositions and methods for controlling undesirable vegetation using the compounds I.

Furthermore, we have found that the compounds I are also suitable for the desiccation/defoliation of parts of plants, suitable plants being crop plants such as cotton, potatoes, oil seed rape, sunflower, soybean or field beans, in particular cotton. Thus, we have found compositions for the desiccation and/or defoliation of plants, processes for preparing these compositions and methods for the desiccation and/or defoliation of plants using the compounds I.

Depending on the substitution pattern, the compounds of the formula I can contain one or more chiral centers, in which case they exist in the form of enantiomer or diastereomer mixtures. For compounds I having at least one olefinic radical, E/Z isomers may also be possible. The invention provides both the pure enantiomers or diastereomers and also mixtures thereof.

The organic moieties mentioned in the definition of the substituents $R^1$, $R^2$ and $R^5$ to $R^8$ or as radicals on cycloalkyl, phenyl or heterocyclic rings are—like the term halogen—collective terms for individual listings of the individual group members. All carbon chains, i.e. all alkyl, haloalkyl, cyanoalkyl, oxyalkyl, aminoalkyl, oxycarbonylalkyl, aminocarbonylalkyl, phosphonylalkyl, oxyaminoalkyl, phenylalkyl, heterocyclylalkyl, alkenyl, haloalkenyl, cyanoalkenyl, alkynyl, haloalkynyl and cyanoalkynyl moieties, can be straight-chain or branched. Halogenated substituents preferably carry from 1 to 5 identical or different halogen atoms. The term halogen represents in each case fluorine, chlorine, bromine or iodine.

Other examples of meanings are:

$C_1$–$C_4$-alkyl: $CH_3$, $C_2H_5$, n-propyl, $CH(CH_3)_2$, n-butyl, 1-methylpropyl, 2-methylpropyl or $C(CH_3)_3$;

$C_1$–$C_4$-haloalkyl: a $C_1$–$C_4$-alkyl radical as mentioned above which is partially or fully substituted by fluorine, chlorine, bromine and/or iodine, i.e., for example, $CH_2F$, $CHF_2$, $CF_3$, $CH_2Cl$, $CH(Cl)_2$, $C(Cl)_3$, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, $C_2F_5$, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, $CH_2$—$C_2F_5$, $CF_2$—$C_2F_5$, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl;

$C_1$–$C_6$-alkyl: $C_1$–$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably $CH_3$, $C_2H_5$, $CH_2$—$C_2H_5$, $CH(CH_3)_2$, n-butyl, $C(CH_3)_3$, n-pentyl or n-hexyl;

$C_1$–$C_6$-haloalkyl: a $C_1$–$C_6$-alkyl radical as mentioned above which is partially or fully substituted by fluorine, chlorine, bromine and/or iodine, i.e., for example, one of the radicals mentioned under $C_1$–$C_4$-haloalkyl or 5-fluoro-1-pentyl, 5-chloro-1-pentyl, 5-bromo-1-pentyl, 5-iodo-1-pentyl, 5,5,5-trichloro-1-pentyl, n-$C_5F_{11}$, 6-fluoro-1-hexyl, 6-chloro-1-hexyl, 6-bromo-1-hexyl, 6-iodo-1-hexyl, 6,6,6-trichloro-1-hexyl or dodecafluorohexyl;

cyano-$C_1$–$C_4$-alkyl: $CH_2CN$, 1-cyanoethyl, 2-cyanoethyl, 1-cyanoprop-1-yl, 2-cyanoprop-1-yl, 3-cyanoprop-1-yl, 1-cyanobut-1-yl, 2-cyanobut-1-yl, 3-cyanobut-1-yl, 4-cyanobut-1-yl, 1-cyanobut-2-yl, 2-cyanobut-2-yl, 3-cyanobut-2-yl, 4-cyanobut-2-yl, 1-($CH_2CN$)eth-1-yl, 1-($CH_2CN$)-1-($CH_3$)-eth-1-yl or 1-($CH_2CN$)prop-1-yl;

hydroxy-$C_1$–$C_4$-alkyl: $CH_2OH$, 1-hydroxyethyl, 2-hydroxyethyl, 1-hydroxyprop-1-yl, 2-hydroxyprop-1-yl, 3-hydroxyprop-1-yl, 1-hydroxybut-1-yl, 2-hydroxybut-1-yl, 3-hydroxybut-1-yl, 4-hydroxybut-1-yl, 1-hydroxybut-2-yl, 2-hydroxybut-2-yl, 3-hydroxybut-2-yl, 4-hydroxybut-2-yl, 1-($CH_2OH$)eth-1-yl, 1-($CH_2OH$)-1-($CH_3$)-eth-1-yl or 1-($CH_2OH$)prop-1-yl;

amino-$C_1$–$C_4$-alkyl: $CH_2NH_2$, 1-aminoethyl, 2-aminoethyl, 1-aminoprop-1-yl, 2-aminoprop-1-yl, 3-aminoprop-1-yl, 1-amino-but-1-yl, 2-aminobut-1-yl, 3-aminobut-1-yl, 4-aminobut-1-yl, 1-aminobut-2-yl, 2-aminobut-2-yl, 3-aminobut-2-yl, 4-amino-but-2-yl, 1-($CH_2NH_2$)eth-1-yl, 1-($CH_2NH_2$)-1-($CH_3$)-eth-1-yl or 1-($CH_2NH_2$)prop-1-yl;

hydroxycarbonyl-$C_1$–$C_4$-alkyl: $CH_2COOH$, 1-(COOH)ethyl, 2-(COOH)ethyl, 1-(COOH)prop-1-yl, 2-(COOH)prop-1-yl, 3-(COOH)prop-1-yl, 1-(COOH)but-1-yl, 2-(COOH)but-1-yl, 3-(COOH)but-1-yl, 4-(COOH)but-1-yl, 1-(COOH)but-2-yl, 2-(COOH)but-2-yl, 3-(COOH)but-2-yl, 4-(COOH)but-2-yl, 1-($CH_2COOH$)eth-1-yl, 1-($CH_2COOH$)-1-($CH_3$)eth-1-yl or 1-($CH_2COOH$)prop-1-yl;

aminocarbonyl-$C_1$–$C_4$-alkyl: $CH_2CONH_2$, 1-($CONH_2$)ethyl, 2-($CONH_2$)ethyl, 1-($CONH_2$)prop-1-yl, 2-($CONH_2$)prop-1-yl, 3-($CONH_2$)prop-1-yl, 1-($CONH_2$)but-1-yl, 2-($CONH_2$)but-1-yl, 3-($CONH_2$)but-1-yl, 4-($CONH_2$)but-1-yl, 1-($CONH_2$)but-2-yl, 2-($CONH_2$)but-2-yl, 3-($CONH_2$)but-2-yl, 4-($CONH_2$)but-2-yl, 1-($CH_2CONH_2$)eth-1-yl, 1-($CH_2CONH_2$)-1-($CH_3$)eth-1-yl or 1-($CH_2CONH_2$)prop-1-yl;

phenyl-$C_1$–$C_4$-alkyl: benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut-2-yl, 2-phenylbut-2-yl, 3-phenylbut-2-yl, 4-phenylbut-2-yl, 1-(benzyl)eth-1-yl, 1-(benzyl)-1-(methyl)eth-1-yl or 1-(benzyl)prop-1-yl, preferably benzyl or 2-phenylethyl;

heterocyclyl-$C_1$–$C_4$-alkyl: heterocyclylmethyl, 1-heterocyclylethyl, 2-heterocyclylethyl, 1-heterocyclylprop-1-yl, 2-heterocyclylprop-1-yl, 3-heterocyclylprop-1-yl, 1-heterocyclylbut-1-yl, 2-heterocyclylbut-1-yl, 3-heterocyclylbut-1-yl, 4-heterocyclylbut-1-yl, 1-heterocyclylbut-2-yl, 2-heterocyclylbut-2-yl, 3-heterocyclylbut-2-yl, 3-heterocyclylbut-2-yl, 4-heterocyclylbut-2-yl, 1-(heterocyclylmethyl)eth-1-yl, 1-(heterocyclylmethyl)-1-(methyl)eth-1-yl or 1-(heterocyclylmethyl)prop-1-yl, preferably heterocyclylmethyl or 2-heterocyclylethyl;

$C_1$–$C_4$-alkoxy: $OCH_3$, $OC_2H_5$, $OCH_2$—$C_2H_5$, $OCH(CH_3)_2$, n-butoxy, $OCH(CH_3)$—$C_2H_5$, $OCH_2$—$CH(CH_3)_2$ or $C(CH_3)_3$, preferably $OCH_3$, $OC_2H_5$ or $OCH(CH_3)_2$;

$C_1$–$C_4$-haloalkoxy: a $C_1$–$C_4$-alkoxy radical as mentioned above which is partially or fully substituted by fluorine, chlorine, bromine and/or iodine, i.e., for example, $OCH_2F$, $OCHF_2$, $OCF_3$, $OCH_2Cl$, $OCH(Cl)_2$, $OC(Cl)_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy, preferably $OCHF_2$, $OCF_3$, dichlorofluoromethoxy, chlorodifluoromethoxy or 2,2,2-trifluoroethoxy;

$C_1$–$C_4$-alkylthio: $SCH_3$, $SC_2H_5$, $SCH_2$—$C_2H_5$, $SCH(CH_3)_2$, n-butylthio, 1-methylpropylthio, $SCH_2$—$CH(CH_3)_2$ or $SC(CH_3)_3$, preferably $SCH_3$ or $SC_2H_5$;

$C_1$–$C_4$-haloalkylthio: a $C_1$–$C_4$-alkylthio radical as mentioned above which is partially or fully substituted by fluorine, chlorine, bromine and/or iodine, i.e., for example, $SCH_2F$, $SCHF_2$, $SCF_3$, $SCH_2Cl$, $SCH(Cl)_2$, $SC(Cl)_3$, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, $SC_2F_5$, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, $SCH_2$—$C_2F_5$, $SCF_2$—$C_2F_5$, 1-($CH_2F$)-2-fluoroethylthio, 1-($CH_2Cl$)-2-chloroethylthio, 1-($CH_2Br$)-2-bromoethylthio, 4-fluorobutylthio, 4-chlorobutylthio, 4-bromobutylthio or $SCF_2$—$CF_2$—$C_2F_5$, preferably $SCHF_2$, $SCF_3$, dichlorofluoromethylthio, chlorodifluoromethylthio or 2,2,2-trifluoroethylthio;

$C_1$–$C_4$-alkoxy-$C_1$–$C_4$-alkyl: $C_1$–$C_4$-alkyl which is substituted by $C_1$–$C_4$-alkoxy—as mentioned above—, i.e., for example, $CH_2$—$OCH_3$, $CH_2$—$OC_2H_5$, n-propoxymethyl, $CH_2$—$OCH(Ch_3)_2$, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl or 4-(1,1-dimethylethoxy)butyl, preferably $CH_2$—$OCH_3$, $CH_2$—$OC_2H_5$, 2-($OCH_3$)ethyl or 2-($OC_2H_5$)ethyl;

$C_1$–$C_4$-haloalkoxy-$C_1$–$C_4$-alkyl: $C_1$–$C_4$-alkyl which is substituted by $C_1$–$C_4$-haloalkoxy as mentioned above, i.e., for example, 2-($OCHF_2$)ethyl, 2-($OCF_3$)ethyl or 2-($OC_2F_5$)ethyl;

$C_1$–$C_4$-alkylthio-$C_1$–$C_4$-alkyl: $C_1$–$C_4$-alkyl which is substituted by $C_1$–$C_4$-alkylthio—as mentioned above, i.e.,—for example, $CH_2$—$SCH_3$, $CH_2$—$SC_2H_5$, n-propylthiomethyl, $CH_2$—$SCH(CH_3)_2$, n-butylthiomethyl, (1-methylpropylthio)methyl, (2-methylpropylthio)methyl, $CH_2$—$SC(CH_3)_3$, 2-((methylthio)ethyl, 2-(ethylthio)ethyl, 2-(n-propylthio)ethyl, 2-(1-methylethylthio)ethyl, 2-(n-butylthio)ethyl, 2-(1-methylpropylthio)ethyl, 2-(2-methylpropylthio)ethyl, 2-(1,1-dimethylethylthio)ethyl, 2-(methylthio)propyl, 2-(ethylthio)propyl, 2-(n-propylthio)propyl, 2-(1-methylethylthio )propyl, 2-(n-butylthio )propyl, 2-(1-methylpropylthio)propyl, 2-(2-methylpropylthio)propyl, 2-(1,1-dimethylethylthio)propyl, 3-(methylthio)propyl, 3-(ethylthio)propyl, 3-(n-propylthio)propyl, 3-(1-methylethylthio)propyl, 3-(n-butylthio)propyl, 3-(1-methylpropylthio)propyl, 3-(2-methylpropylthio)propyl, 3-(1,1-dimethylethylthio)propyl, 2-(methylthio)butyl, 2-2-(ethylthio)butyl, 2-(n-propylthio)butyl, 2-(1-methylethylthio)butyl, 2-(n-butylthio)butyl, 2-(1-methylpropylthio)butyl, 2-(2-methylpropylthio)butyl, 2-(1,1-dimethylethylthio)butyl, 3-(methylthio)butyl, 3-(ethylthio)butyl, 3-(n-propylthio)butyl, 3-(1-methylethylthio)butyl, 3-(n-butylthio)butyl, 3-(1-methylpropylthio)butyl, 3-(2-methylpropylthio)butyl, 3-(1,1-dimethylethylthio)butyl, 4-(methylthio)butyl, 4-(ethylthio)butyl, 4-(n-propylthio)butyl, 4-(1-methylethylthio)butyl, 4-(n-butylthio)butyl, 4-(1-methylpropylthio)butyl, 4-(2-methylpropylthio)butyl or 4-(1,1-dimethylethylthio)butyl, preferably $CH_2$—$SCH_3$, $CH_2$—$SC_2H_5$, 2-($SCH_3$)ethyl or 2-($SC_2H_5$)ethyl;

$C_1$–$C_4$-haloalkylthio-$C_1$–$C_4$-alkyl: $C_1$–$C_4$-alkyl which is substituted by $C_1$–$C_4$-haloalkylthio as mentioned above, i.e., for example, 2-($SCHF_2$)ethyl, 2-($SCF_3$)ethyl or 2-($SC_2F_5$)ethyl;

($C_1$–$C_4$-alkoxy)imino-$C_1$–$C_4$-alkyl: $C_1$–$C_4$-alkyl which is substituted by ($C_1$–$C_4$-alkoxy)imino such as=$N$—$CH_3$, =$N$—$C_2H_5$, =$NCH_2$—$C_2H_5$, =$N$—$CH(CH_3)_2$, =$NCH_2$—$CH_2$—$C_2H_5$, =$NCH(CH_3)$—$C_2H_5$, =$NCH_2$—$CH(CH_3)_2$ or =$N$—$C(CH_3)_3$, i.e., for example, $Ch$=$N$—$CH_3$, $CH$=$N$—$C_2H_5$, $CH_2$—$CH$=$N$—$CH_3$ or $CH_2$—$CH$=$N$—$C_2H_5$;

($C_1$–$C_4$-alkyl)carbonyl: $CO$—$CH_3$, $CO$—$C_2H_5$, $CO$—$CH_2$—$C_2H_5$, $CO$—$CH(CH_3)_2$, n-butylcarbonyl, $CO$—$CH(CH_3)$—$C_2H_5$, $CO$—$CH_2$—$CH(CH_3)_2$ or $CO$—$C(CH_3)_3$, preferably $CO$—$CH_3$ or $CO$—$C_2H_5$;

($C_1$–$C_4$-haloalkyl)carbonyl: a ($C_1$–$C_4$-alkyl)carbonyl radical—as mentioned above—which is partially or fully substituted by fluorine, chlorine, bromine and/or iodine, i.e., for example, $CO$—$CH_2F$, $CO$—$CHF_2$, $CO$—$CF_3$, $CO$—$CH_2Cl$, $CO$—$CH(C_1)_2$, $CO$—$C(Cl)_3$, chlorofluoromethylcarbonyl, dichlorofluoromethylcarbonyl, chlorodifluoromethylcarbonyl, 2-fluoroethylcarbonyl, 2-chloroethylcarbonyl, 2-bromoethylcarbonyl, 2-iodoethylcarbonyl, 2,2-difluoroethylcarbonyl, 2,2,2-trifluoroethylcarbonyl, 2-chloro-2-fluoroethylcarbonyl, 2-chloro-2,2-difluoroethylcarbonyl, 2,2-dichloro-2-fluoroethylcarbonyl, 2,2,2-trichloroethylcarbonyl, $CO$—$C_2F_5$, 2-fluoropropylcarbonyl, 3-fluoropropylcarbonyl, 2,2-difluoropropylcarbonyl, 2,3-difluoropropylcarbonyl, 2-chloropropylcarbonyl, 3-chloropropylcarbonyl, 2,3-dichloropropylcarbonyl, 2-bromopropylcarbonyl, 3-bromopropylcarbonyl, 3,3,3-trifluoropropylcarbonyl, 3,3,3-trichloropropylcarbonyl, $CO$—$CH_2$—$C_2F_5$, $CO$—$CF_2$—$C_2F_5$, 1-($CH_2F$)-2-fluoroethylcarbonyl, 1-($CH_2Cl$)-2-chloroethylcarbonyl, 1-($CH_2Br$)-2-bromoethylcarbonyl, 4-fluorobutylcarbonyl, 4-chlorobutylcarbonyl, 4-bromobutylcarbonyl or nonafluorobutylcarbonyl, preferably $CO$—$CF_3$ $CO$—$CH_2Cl$ or 2,2,2-trifluoroethylcarbonyl;

($C_1$–$C_4$-alkyl)carbonyloxy: $O$—$CO$—$CH_3$, $O$—$CO$—$C_2H_5$, $O$—$CO$—$CH_2$—$C_2H_5$, $O$—$CO$—$CH(CH_3)_2$, $O$—$CO$—$CH_2$—$CH_2$—$C_2H_5$, $O$—$CO$—$CH(CH_3)$—$C_2H_5$, $O$—$CO$—$CH_2$—$CH(CH_3)_2$ or $O$—$CO$—$C(CH_3)_3$, preferably $O$—$CO$—$CH_3$ or $O$—$CO$—$C_2H_5$;

($C_1$–$C_4$-haloalkyl)carbonyloxy: a ($C_1$–$C_4$-alkyl)carbonyl radical—as mentioned above—which is partially or fully substituted by fluorine, chlorine, bromine and/or iodine, i.e., for example, O—CO—$CH_2$F, O—CO—$CHF_2$, O—CO—$CF_3$, O—CO—$CH_2$Cl, O—CO—$CH(Cl)_2$, O—CO—$C(Cl)_3$, chlorofluoromethylcarbonyloxy, dichlorofluoromethylcarbonyloxy, chlorodifluoromethylcarbonyloxy, 2-fluoroethylcarbonyloxy, 2-chloroethylcarbonyloxy, 2-bromoethylcarbonyloxy, 2-iodoethylcarbonyloxy, 2,2-difluoroethylcarbonyloxy, 2,2,2-trifluoroethylcarbonyloxy, 2-chloro-2-fluoroethylcarbonyloxy, 2-chloro-2,2-difluoroethylcarbonyloxy, 2,2-dichloro-2-fluoroethylcarbonyloxy, 2,2,2-trichloroethylcarbonyloxy, O—CO—$C_2F_5$, 2-fluoropropylcarbonyloxy, 3-fluoropropylcarbonyloxy, 2,2-difluoropropylcarbonyloxy, 2,3-difluoropropylcarbonyloxy, 2-chloropropylcarbonyloxy, 3-chloropropylcarbonyloxy, 2,3-dichloropropylcarbonyloxy, 2-bromopropylcarbonyloxy, 3-bromopropylcarbonyloxy, 3,3,3-trifluoropropylcarbonyloxy, 3,3,3-trichloropropylcarbonyloxy, O—CO—$CH_2$—$C_2F_5$, O—CO—$CF_2$—$C_2F_5$, 1-($CH_2$F)-2-fluoroethylcarbonyloxy, 1-($CH_2$Cl)-2-chloroethylcarbonyloxy, 1-($CH_2$Br)-2-bromoethylcarbonyloxy, 4-fluorobutylcarbonyloxy, 4-chlorobutylcarbonyloxy, 4-bromobutylcarbonyloxy or nonafluorobutylcarbonyloxy, preferably O—CO—$CF_3$, O—CO—$CH_2$Cl or 2,2,2-trifluoroethylcarbonyloxy;

($C_1$–$C_4$-alkoxy)carbonyl: CO—$OCH_3$, CO—$OC_2H_5$, n-propoxycarbonyl, CO—$OCH(CH_3)_2$, n-butoxycarbonyl, CO—$OCH(CH_3)$—$C_2H_5$, CO—$OCH_2$—$CH(CH_3)_2$ or CO—$OC(CH_3)_3$, preferably CO—$OCH_3$ or CO—$OC_2H_5$;

($C_1$–$C_4$-alkoxy)carbonyl-$C_1$–$C_4$-alkyl: $C_1$–$C_4$-alkyl which is substituted by ($C_1$–$C_4$-alkoxy)carbonyl—as mentioned above—, i.e., for example, $CH_2$—CO—$OCH_3$, $CH_2$—CO—$OC_2H_5$, n-propoxycarbonyl-methyl, $CH_2$—CO—$OCH(CH_3)_2$, n-butoxycarbonylmethyl, $CH_2$—CO—$OCH(CH_3)$—$C_2H_5$, $CH_2$—CO—$OCH_2$—$CH(CH_3)_2$, $CH_2$—CO—$OC(CH_3)_3$, 1-(methoxycarbonyl)ethyl, 1-(ethoxycarbonyl)ethyl, 1-(n-propoxycarbonyl)ethyl, 1-(1-methylethoxycarbonyl)ethyl, 1-(n-butoxycarbonyl)ethyl, 2-(methoxycarbonyl)ethyl, 2-(ethoxycarbonyl)ethyl, 2-(n-propoxycarbonyl)ethyl, 2-(1-methylethoxycarbonyl)ethyl, 2-(n-butoxycarbonyl)ethyl, 2-(1-methylpropoxycarbonyl)ethyl, 2-(2-methylpropoxycarbonyl)-ethyl, 2-(1,1-dimethylethoxycarbonyl)ethyl, 2-(methoxycarbonyl)propyl, 2-(ethoxycarbonyl)propyl, 2-(n-propoxycarbonyl)propyl, 2-(1-methylethoxycarbonyl)propyl, 2-(n-butoxycarbonyl)propyl, 2-(1-methylpropoxycarbonyl)propyl, 2-(2-methylpropoxycarbonyl)propyl, 2-(1,1-dimethylethoxycarbonyl)propyl, 3-(methoxycarbonyl)propyl, 3-(ethoxycarbonyl)propyl, 3-(n-propoxycarbonyl)propyl, 3-(1-methylethoxycarbonyl)propyl, 3-(n-butoxycarbonyl)propyl, 3-(1-methylpropoxycarbonyl)propyl, 3-(2-methylpropoxycarbonyl)propyl, 3-(1,1-dimethylethoxycarbonyl)propyl, 2-(methoxycarbonyl)butyl, 2-(ethoxycarbonyl)butyl, 2-(n-propoxycarbonyl)butyl, 2-(1-methylethoxycarbonyl)butyl, 2-(n-butoxycarbonyl)butyl, 2-(1-methylpropoxycarbonyl)butyl, 2-(2-methylpropoxycarbonyl)-butyl, 2-(1,1-dimethylethoxycarbonyl)butyl, 3-(methoxycarbonyl)butyl, 3-(ethoxycarbonyl)butyl, 3-(n-propoxycarbonyl)butyl, 3-(1-methylethoxycarbonyl)butyl, 3-(n-butoxycarbonyl)butyl, 3-(1-methylpropoxycarbonyl)butyl, 3-(2-methylpropoxycarbonyl)butyl, 3-(1,1-dimethylethoxycarbonyl)butyl, 4-(methoxycarbonyl)butyl, 4-(ethoxycarbonyl)butyl, 4-(n-propoxycarbonyl)butyl, 4-(1-methylethoxycarbonyl)butyl, 4-(n-butoxycarbonyl)butyl, 4-(1-methylpropoxycarbonyl)butyl, 4-(2-methylpropoxycarbonyl)-butyl or 4-(1,1-dimethylethoxycarbonyl)butyl, preferably $CH_2$—CO—$OCH_3$, $CH_2$—CO—$OC_2H_5$, 1-(methoxycarbonyl)ethyl or 1-(ethoxycarbonyl)ethyl;

($C_1$–$C_4$-alkylthio)carbonyl: CO—$SCH_3$, CO—$SC_2H_5$, CO—$SCH_2$—$C_2H_5$, CO—$SCH(CH_3)_2$, CO—$SCH_2CH_2$—$C_2H_5$, CO—$SCH(CH_3)$—$C_2H_5$, CO—$SCH_2$—$CH(CH_3)_2$ or CO—$SC(CH_3)_3$, preferably CO—$SCH_3$ or CO—$SC_2H_5$;

($C_1$–$C_4$-alkylthio)carbonyl-$C_1$–$C_4$-alkyl: $C_1$–$C_4$-alkyl which is substituted by ($C_1$–$C_4$-alkylthio)carbonyl—as mentioned above—, i.e., for example, $CH_2$—CO—$SCH_3$, $CH_2$—CO—$SC_2H_5$, $CH_2$—CO—$SCH_5$—$H_5$, $CH_2$—CO—$SCH(CH_3)_2$, $CH_2$—CO—$SCH_2CH_2$—$C_2H_5$, $CH_2$—CO—$SCH(CH_3)$—$C_2H_5$, $CH_2$—CO—$SCH_2$—$CH(CH_3)_2$, $CH_2$—CO—$SC(CH_3)_3$, 1-(CO—$SCH_3$)ethyl, 1-(CO—$SC_2H_5$)ethyl, 1-(CO—$SCH_2$—$C_2H_5$)ethyl, 1-[CO—$SCH(CH_3)_2$]ethyl, 1-(CO—$SCH_2CH_2$—$C_2H_5$) ethyl, 1-[CO—$SCH(CH_3)$—$C_2H_5$]ethyl, 1-[CO—$SCH_2$—$CH(CH_3)_2$]ethyl, 1-[CO—SC $(CH_3)_3$]ethyl, 2-(CO—$SCH_3$)ethyl, 2-(CO—$SC_2H_5$)ethyl, 2-(CO—$SCH_2$—$C_2H_5$)ethyl, 2-[CO—$SCH(CH_3)_2$]ethyl, 2-(CO—$SCH_2CH_2$—$C_2H_5$)ethyl, 2-[CO—$SCH(CH_3)$—$C_2H_5$] ethyl, 2-[CO—$SCH_2$—$CH(CH_3)_2$]ethyl, 2-[CO—SC $(CH_3)_3$]ethyl, 2-(CO—$SCH_3$)-propyl, 2-(CO—$SC_2H_5$) propyl, 2-(CO—$SCH_2$—$C_2H_5$)propyl, 2-[CO—SCH $(CH_3)_2$]propyl, 2-(CO—$SCH_2CH_2$—$C_2H_5$)propyl, 2-[CO—$SCH(CH_3)$—$C_2H_5$]propyl, 2-[CO—$SCH_2$—CH $(CH_3)_2$]propyl, 2-[CO—$SC(CH_3)_3$]propyl, 3-(CO—$SCH_3$)propyl, 3-(CO—$SC_2H_5$)propyl, 3-(CO—$SCH_2$—$C_2H_5$)propyl, 3-[CO—$SCH(CH_3)_2$]propyl, 3-(CO—$SCH_2CH_2$—$C_2H_5$)propyl, 3-[CO—$SCH(CH_3)$—$C_2H_5$] propyl, 3-[CO—$SCH_2$—$CH(CH_3)_2$]propyl, 3-[CO—SC $(CH_3)_3$]propyl, 2-(CO—$SCH_3$)butyl, 2-(CO—$SC_2H_5$) butyl, 2-(CO—$SCH_2$—$C_2H_5$)butyl, 2-[CO—$SCH(CH_3)_2$]butyl, 2-(CO—$SCH_2CH_2$—$C_2H_5$)butyl, 2-[CO—SCH $(CH_3)$—$C_2H_5$]butyl, 2-[CO—$SCH_2$—$CH(CH_3)_2$]butyl, 2-[CO—$SC(CH_3)_3$]butyl, 3-(CO—$SCH_3$)butyl, 3-(CO—$SC_2H_5$)butyl, 3-(CO—$SCH_2$—$C_2H_5$)butyl, 3-[CO—SCH $(CH_3)_2$]butyl, 3-(CO—$SCH_2CH_2$—$C_2H_5$)butyl, 3-[CO—$SCH(CH_3)$—$C_2H_5$]butyl, 3-[CO—$SCH_2$—$CH(CH_3)_2$] butyl, 3-[CO—$SC(CH_3)_3$]butyl, 4-(CO—$SCH_3$)-butyl, 4-(CO—$SC_2H_5$)butyl, 4-(CO—$SCH_2$—$C_2H_5$)butyl, 4-[CO—$SCH(CH_3)_2$]butyl, 4-(CO—$SCH_2CH_2$—$C_2H_5$) butyl, 4-[CO—$SCH(CH_3)$—$C_2H_5$]butyl, 4-[CO—$SCH_2$—$CH(CH_3)_2$]butyl or 4-[CO—$SC(CH_3)_3$]butyl, preferably $CH_2$—CO—$SCH_3$, $CH_2$—CO—$SC_2H_5$, 1-(CO—$SCH_3$)ethyl or 1-(CO—$SC_2H_5$)ethyl;

$C_1$–$C_4$-alkylsulfinyl: SO—$CH_3$, SO—$C_2H_5$, SO—$CH_2$—$C_2H_5$, SO—$CH(CH_3)_2$, n-butylsulfinyl, SO—CH $(CH_3)$—$C_2H_5$, SO—$CH_2$—$CH(CH_3)_2$ or SO—$C(CH_3)_3$, preferably SO—$CH_3$ or SO—$C_2H_5$;

$C_1$–$C_4$-haloalkylsulfinyl: a $C_1$–$C_4$-alkylsulfinyl radical—as mentioned above—which is partially or fully substituted by fluorine, chlorine, bromine and/or iodine, i.e, for example, SO—$CH_2$F, SO—$CHF_2$, SO—$CF_3$, SO—$CH_2$Cl, SO—$CH(Cl)_2$, SO—$C(Cl)_3$, chlorofluoromethylsulfinyl, dichlorofluoromethylsulfinyl, chlorodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2-chloro-2-fluoroethylsulfinyl, 2-chloro-2,2-difluoroethylsulfinyl, 2,2-dichloro-2-fluoroethylsulfinyl, 2,2,2-trichloroethylsulfinyl, SO—$C_2F_5$, 2-fluoropropylsulfinyl, 3-fluoropropylsulfinyl, 2,2-difluoropropylsulfinyl, 2,3-difluoropropylsulfinyl, 2-chloropropylsulfinyl, 3-chloropropylsulfinyl, 2,3-dichloropropylsulfinyl, 2-bromopropylsulfinyl, 3-bromopropylsulfinyl, 3,3,3-trifluoropropylsulfinyl, 3,3,3-trichloropropylsulfinyl, SO—$CH_2$—$C_2F_5$, SO—$CF_2$—$C_2F_5$, 1-($CH_2F$)-2-fluoroethylsulfinyl, 1-($CH_2Cl$)-2-chloroethylsulfinyl, 1-($CH_2Br$)-2-bromoethylsulfinyl, 4-fluorobutylsulfinyl, 4-chlorobutylsulfinyl, 4-bromobutylsulfinyl or nonafluorobutylsulfinyl, preferably SO—$CF_3$, SO—$CH_2Cl$ or 2,2,2-trifluoroethylsulfinyl;

$C_1$–$C_4$-alkylsulfinyl-$C_1$–$C_4$-alkyl: $C_1$–$C_4$-alkyl which is subsituted by $C_1$–$C_4$-alkylsulfinyl as mentioned above, i.e., for example, $CH_2SOCH_3$, $CH_2SOC_2H_5$, n-propylsulfinylmethyl, $CH_2SOCH(CH_3)_2$, n-butylsulfinylmethyl, (1-methylpropylsulfinyl)methyl, (2-methylpropylsulfinyl)methyl, (1,1-dimethylethylsulfinyl)-methyl, 2-methylsulfinylethyl, 2-ethylsulfinylethyl, 2-(n-propylsulfinyl)ethyl, 2-(1-methylethylsulfinyl)ethyl, 2-(n-butylsulfinyl)ethyl, 2-(1-methylpropylsulfinyl)ethyl, 2-(2-methylpropylsulfinyl) ethyl, 2-(1,1-dimethylethylsulfinyl)ethyl, 2-($SOCH_3$) propyl, 3-($SOCH_3$)propyl, 2-($SOC_2H_5$)propyl, 3-($SOC_2H_5$)propyl, 3-(propylsulfinyl)propyl, 3-(butylsulfinyl)propyl, 4-($SOCH_3$)butyl, 4-($SOC_2H_5$) butyl, 4-(n-propylsulfinyl)butyl or 4-(n-butylsulfinyl) butyl, in particular 2-($SOCH_3$)ethyl;

$C_1$–$C_4$-haloalkylsulfinyl-$C_1$–$C_4$-alkyl: $C_1$–$C_4$-alkyl which is substituted by $C_1$–$C_4$-haloalkylsulfinyl as mentioned above, i.e, for example, 2-(2,2,2-trifluoroethylsulfinyl) ethyl;

$C_1$–$C_4$-alkylsulfonyl: $SO_2$—$CH_3$, $SO_2$—$C_2H_5$, $SO_2$—$CH_2$—$C_2H_5$, $SO_2$—$CH(CH_3)_2$, n-butylsulfonyl, $SO_2$—$CH(CH_3)$—$C_2H_5$, $SO_2$—$CH_2$—$CH(CH_3)_2$ or $SO_2$—$C(CH_3)_3$, preferably $SO_2$—$CH_3$ or $SO_2$—$C_2H_5$;

$C_1$–$C_4$-haloalkylsulfonyl: a $C_1$–$C_4$-alkylsulfonyl radical—as mentioned above—which is partially or fully substituted by fluorine, chlorine, bromine and/or iodine, i.e., for example, $SO_2$—$CH_2F$, $SO_2$—$CHF_2$, $SO_2$—$CF_3$, $SO_2$—$CH_2Cl$, $SO_2$—$CH(Cl)_2$, $SO_2$—$C(Cl)_3$, chlorofluoromethylsulfonyl, dichlorofluoromethylsulfonyl, chlorodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, $SO_2$—$C_2F_5$, 2-fluoropropylsulfonyl, 3-fluoropropylsulfonyl, 2,2-difluoropropylsulfonyl, 2,3-difluoropropylsulfonyl, 2-chloropropylsulfonyl, 3-chloropropylsulfonyl, 2,3-dichloropropylsulfonyl, 2-bromopropylsulfonyl, 3-bromopropylsulfonyl, 3,3,3-trifluoropropylsulfonyl, 3,3,3-trichloropropylsulfonyl, $SO_2$—$CH_2$—$C_2F_5$, $SO_2$—$CF_2$—$C_2F_5$, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl or nonafluorobutylsulfonyl, preferably $SO_2$—$CH_2Cl$, $SO_2$—$CF_3$ or 2,2,2-trifluoroethylsulfonyl;

$C_1$–$C_4$-alkylsulfonyl-$C_1$–$C_4$-alkyl: $C_1$–$C_4$-alkyl which is substituted by —$C_1$–$C_4$-alkylsulfonyl as mentioned above, i.e., for example, $CH_2SO_2$—$CH_3$, $CH_2SO_2$—$C_2H_5$, $CH_2SO_2$—$CH_2$—$C_2H_5$, $CH_2SO_2$—$CH(CH_3)_2$, $CH_2SO_2$—$CH_2CH_2$—$C_2H_5$, (1-methylpropylsulfonyl)methyl, (2-methylpropylsulfonyl)methyl, $CH_2SO_2$—$C(CH_3)_3$, $CH(CH_3)SO_2$—$CH_3$, $CH(CH_3)SO_2$—$C_2H_5$, $CH_2CH_2SO_2$—$CH_3$, $CH_2CH_2SO_2$—$C_2H_5$, $CH_2CH_2SO_2$—$CH_2$—$C_2H_5$, $CH_2CH_2SO_2$—$CH(CH_3)_2$, $CH_2CH_2SO_2$—$CH_2CH_2$—$C_2H_5$, 2-(1-methylpropylsulfonyl)ethyl, 2-(2-methylpropylsulfonyl) ethyl, $CH_2CH_2SO_2$—$C(CH_3)_3$, 2-($SO_2$—$CH_3$)propyl, 2-($SO_2$—$C_2H_5$)propyl, 2-($SO_2CH_2$—$C_2H_5$)propyl, 2-[$SO_2$—$CH(CH_3)_2$]propyl, 2-($SO_2$—$CH_2CH_2$—$C_2H_5$) propyl, 2-(1-methylpropylsulfonyl)propyl, 2-(2-methylpropylsulfonyl)propyl, 2-[$SO_2$—$C(CH_3)_3$]propyl, 3-($SO_2$—$CH_3$)propyl, 3-($SO_2$—$C_2H_5$)propyl, 3-($SO_2CH_2$—$C_2H_5$)propyl, 3-[$SO_2$—$CH(CH_3)_2$]propyl, 3-($SO_2$—$CH_2CH_2$—$C_2H_5$)propyl, 3-(1-methylpropylsulfonyl)propyl, 3-(2-methylpropylsulfonyl)propyl, 3-[$SO_2$—$C(CH_3)_3$]propyl, 2-($SO_2$—$CH_3$)butyl, 2-($SO_2$—$C_2H_5$)butyl, 2-($SO_2CH_2$—$C_2H_5$)butyl, 2-[$SO_2$—$CH(CH_3)_2$]butyl, 2-($SO_2$—$CH_2CH_2$—$C_2H_5$)butyl, 2-(1-methylpropylsulfonyl)butyl, 2-(2-methylpropylsulfonyl)butyl, 2-[$SO_2$—$C(CH_3)_3$] butyl, 3-($SO_2$—$CH_3$)butyl, 3-($SO_2$—$C_2H_5$)butyl, 3-($SO_2$—$CH_2$—$C_2H_5$) 3-[$SO_2$—$CH(CH_3)_2$]butyl, 3-($SO_2$—$CH_2CH_2$—$C_2H_5$)butyl, 3-(1-methylpropylsulfonyl)butyl, 3-(2-methylpropylsulfonyl) butyl, 3-[$SO_2$—$C(CH_3)_3$]butyl, 4-($SO_2$—$CH_3$)butyl, 4-($SO_2$—$C_2H_5$)butyl, 4-($SO_2$—$CH_2$—$C_2H_5$) 4-[$SO_2$—$CH(CH_3)_2$]butyl, 4-($SO_2$—$CH_2CH_2$—$C_2H_5$)butyl, 4-(1-methylpropylsulfonyl)butyl, 4-(2-methylpropylsulfonyl) butyl or 4-[$SO_2$—$C(CH_3)_3$]butyl, in particular $CH_2CH_2SO_2$—$CH_3$ or $CH_2CH_2SO_2$—$C_2H_5$;

$C_1$–$C_4$-haloalkylsulfonyl-$C_1$–$C_4$-alkyl: $C_1$–$C_4$-alkyl which is substituted by $C_1$–$C_4$-haloalkylsulfonyl as mentioned above, i.e., for example, 2-(2,2,2-trifluoroethylsulfonyl) ethyl;

$C_1$–$C_4$-alkylamino-$C_1$–$C_4$-alkyl: $C_1$–$C_4$-alkyl which is substituted by $C_1$–$C_4$-alkylamino such as —NH—$CH_3$, —NH—$C_2H_5$, —NH—$CH_2$—$C_2H_5$, —NH—$CH(CH_3)_2$, —NH—$CH_2CH_2$—$C_2H_5$, —NH—$CH(CH_3)$—$C_2H_5$, —NH—$CH_2$—$CH(CH_3)_2$ and —NH—$C(CH_3)_3$, preferably —NH—$CH_3$ or —NH—$C_2H_5$, i.e., for example, $CH_2CH_2$—NH—$CH_3$, $CH_2CH_2$—$N(CH_3)_2$, $CH_2CH_2$—NH—$C_2H_5$ or $CH_2CH_2$—$N(C_2H_5)_2$;

$C_1$–$C_4$-alkylaminocarbonyl: CO—NH—$CH_3$, CO—NH—$C_2H_5$, n-propylamino, CO—NH—$CH(CH_3)_2$, CO—NH—$CH_2CH_2$—$C_2H_5$, CO—NH—$CH(CH_3)$—$C_2H_5$, CO—NH—$CH_2$—$CH(CH_3)_2$ or CO—NH—$C(CH_3)_3$, preferably CO—NH—$CH_3$ or CO—NH—$C_2H_5$;

$C_1$–$C_4$-alkylaminocarbonyl-$C_1$–$C_4$-alkyl: $C_1$–$C_4$-alkyl which is substituted by $C_1$–$C_4$-alkylaminocarbonyl as mentioned above, preferably by CO—NH—$CH_3$ or CO—NH—$C_2H_5$, i.e., for example, $CH_2$—CO—NH—$CH_3$, $CH_2$—CO—NH—$C_2H_5$, $CH_2$—CO—NH—$CH_2$—$C_2H_5$, $CH_2$—CO—NH—$CH(CH_3)_2$, $CH_2$—CO—NH—$CH_2CH_2$—$C_2H_5$, $CH_2$—CO—NH—$CH(CH_3)$—$C_2H_5$, $CH_2$—CO—NH—$CH_2$—$CH(CH_3)_2$, $CH_2$—CO—NH—$C(CH_3)_3$, $CH(CH_3)$—CO—NH—$CH_3$, $CH(CH_3)$—CO—NH—$C_2H_5$, 2-(CO—NH—$CH_3$)ethyl, 2-(CO—NH—$C_2H_5$)ethyl, 2-(CO—NH—$CH_2$—$C_2H_5$)-ethyl, 2-[$CH_2$—CO—NH—$CH(CH_3)_2$]ethyl, 2-(CO—NH—$CH_2CH_2$—$C_2H_5$)ethy 2-[CO—NH—$CH(CH_3)$—$C_2H_5$] ethyl, 2-[CO—NH—$CH_2$—$CH(CH_3)_2$]ethyl, 2-[CO—NH—$C(CH_3)_3$]ethyl, 2-(CO—NH—$CH_3$)propyl, 2-(CO—NH—$C_2H_5$)propyl, 2-(CO—NH—$CH_2$—$C_2H_5$) propyl, 2-[$CH_2$—CO—NH—$CH(CH_3)_2$ ]propyl, 2-(CO—NH—CH₂CH₂—C₂H₅)propyl, 2-[CO—NH—CH(CH₃)—C₂H₅]propyl, 2-[CO—NH—CH₂—CH(CH₃)₂]propyl, 2-[CO—NH—C(CH₃)₃]propyl, 3-(CO—NH—CH₃)propyl, 3-(CO—NH—C₂H₅)propyl, 3-(CO—NH—CH₂—C₂H₅)propyl, 3-[CH₂—CO—NH—CH(CH₃)₂]propyl, 3-(CO—NH—CH₂CH₂—C₂H₅)propyl, 3-[CO—NH—CH(CH₃)—C₂H₅]propyl, 3-[CO—NH—CH₂—CH(CH₃)₂]propyl, 3-[CO—NH—C(CH₃)₃]propyl, 2-(CO—NH—CH₃)butyl, 2-(CO—NH—C₂H₅)-butyl, 2-(CO—NH—CH₂—C₂H₅)butyl, 2-[CH₂—CO—NH—CH(CH₃)₂]butyl, 2-(CO—NH—CH₂CH₂—C₂H₅)butyl, 2-[CO—NH—CH(CH₃)—C₂H₅]butyl, 2-[CO—NH—CH₂—CH(CH₃)₂]butyl, 2-[CO—NH—C(CH₃)₃]butyl, 3-(CO—NH—CH₃)butyl, 3-(CO—NH—C₂H₅)butyl, 3-(CO—NH—CH₂—C₂H₅)-butyl, 3-[CH₂—CO—NH—CH(CH₃)₂]butyl, 3-(CO—NH—CH₂CH₂—C₂H₅)butyl 3-[CO—NH—CH(CH₃)—C₂H₅]butyl, 3-[CO—NH—CH₂—CH(CH₃)₂]butyl, 3-[CO—NH—C(CH₃)₃]butyl, 4-(CO—NH—CH₃)butyl, 4-(CO—NH—C₂H₅)butyl, 4-(CO—NH—CH₂—C₂H₅)butyl, 4-[CH₂—CO—NH—CH(CH₃)₂]butyl, 4-(CO—NH—CH₂CH₂—C₂H₅)butyl, 4-[CO—NH—CH(CH₃)—C₂H₅]butyl, 4-[CO—NH—CH₂—CH(CH₃)₂]butyl or 4-[CO—NH—C(CH₃)₃]butyl, preferably CH₂—CO—NH—CH₃, CH₂—CO—NH—C₂H₅, CH(CH₃)—CO—NH—CH₃ or CH(CH₃)—CO—NH—C₂H₅;

di(C₁–C₄-alkyl)amino: N(CH₃)₂, N(C₂H₅)₂, N,N-dipropylamino, N[CH(CH₃)₂]₂, N(n-C₄H₉)₂, N,N-Di-(1-methylpropyl)amino, N,N-di-(2-methylpropyl)amino, N[C(CH₃)₃]₂, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methypropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethyl-ethyl)-N-(2-methylpropyl)amino, preferably N(CH₃)₂ or N(C₂H₅)₂;

di(C₁–C₄-alkyl)amino-C₁–C₄-alkyl: C₁–C₄-alkyl which is substituted by di(C₁–C₄-alkyl)amino as mentioned above, i.e., for example, CH₂N(CH₃)₂, CH₂N(C₂H₅)₂, N,N-dipropylaminomethyl, N,N-di[CH(CH₃)₂]aminomethyl, N,N-dibutylaminomethyl, N,N-di(1-methylpropyl)aminomethyl, N,N-di(2-methylpropyl)aminomethyl, N,N-di[C(CH₃)₃]aminomethyl, N-ethyl-N-methylaminomethyl, N-methyl-N-propylaminomethyl, N-methyl-N-[CH(CH₃)₂]aminomethyl, N-butyl-N-methylaminomethyl, N-methyl-N-(1-methylpropyl)aminomethyl, N-methyl-N-(2-methylpropyl)aminomethyl, N—[C(CH₃)₃]—N-methylaminomethyl, N-ethyl-N-propylaminomethyl, N-ethyl-N—[CH(CH₃)₂]aminomethyl, N-butyl-N-ethylaminomethyl, N-ethyl-N-(1-methylpropyl)aminomethyl, N-ethyl-N-(2-methylpropyl)aminomethyl, N-ethyl-N—[C(CH₃)₃]-aminomethyl, N—[CH(CH₃)₂]—N-propylaminomethyl, N-butyl-N-propylaminomethyl, N-(1-methylpropyl)-N-propylaminomethyl, N-(2-methylpropyl)-N-propylaminomethyl, N—[C(CH₃)₃]—N-propylaminomethyl, N-butyl-N-(1-methylethyl)aminomethyl, N—[CH(CH₃)₂]—N-(1-methylpropyl)aminomethyl, N—[CH(CH₃)₂]—N-(2-methylpropyl)aminomethyl, N—[C(CH₃)₃]—N—[CH(CH₃)₂]aminomethyl, N-butyl-N-(1-methylpropyl)aminomethyl, N-butyl-N-(2-methylpropyl)aminomethyl, N-butyl-N—[C(CH₃)₃]-aminomethyl, N-(1-methylpropyl)-N-(2-methylpropyl)aminomethyl, N—[C(CH₃)₃]—N-(1-methylpropyl)aminomethyl, N—[C(CH₃)₃]—N-(2-methylpropyl)aminomethyl, N,N-dimethylaminoethyl, N,N-diethylaminoethyl, N,N-di(n-propyl)aminoethyl, N,N-di[CH(CH₃)₂]aminoethyl, N,N-dibutylaminoethyl, N,N-di(1-methylpropyl)aminoethyl, N,N-di(2-methylpropyl)aminoethyl, N,N-di[C(CH₃)₃]aminoethyl, N-ethyl-N-methylaminoethyl, N-methyl-N-propylaminoethyl, N-methyl-N—[CH(CH₃)₂]aminoethyl, N-butyl-N-methylaminoethyl, N-methyl-N-(1-methylpropyl)aminoethyl, N-methyl-N-(2-methylpropyl)aminoethyl, N—[C(CH₃)₃]—N-methylaminoethyl, N-ethyl-N-propylaminoethyl, N-ethyl-N—[CH(CH₃)₂]aminoethyl, N-butyl-N-ethylaminoethyl, N-ethyl-N-(1-methylpropyl)aminoethyl, N-ethyl-N-(2-methylpropyl)aminoethyl, N-ethyl-N—[C(CH₃)₃]aminoethyl, N—[CH(CH₃)₂]—N-propylaminoethyl, N-butyl-N-propylaminoethyl, N-(1-methylpropyl)-N-propylaminoethyl, N-(2-methylpropyl)-N-propylaminoethyl, N—[C(CH₃)₃]—N-propylaminoethyl, N-butyl-N—[CH(CH₃)₂]aminoethyl, N—[CH(CH₃)₂]—N-(1-methylpropyl)aminoethyl, N—[CH(CH₃)₂]—N-(2-methylpropyl)aminoethyl, N—[C(CH₃)₃]—N—[CH(CH₃)₂]aminoethyl, N-butyl-N-(1-methylpropyl)aminoethyl, N-butyl-N-(2-methylpropyl)aminoethyl, N-butyl-N—[C(CH₃)₃]aminoethyl, N-(1-methylpropyl)-N-(2-methylpropyl)aminoethyl, N—[C(CH₃)₃]—N-(1-methylpropyl)aminoethyl or N—[C(CH₃)₃]—N-(2-methylpropyl)aminoethyl, in particular N,N-dimethylaminoethyl or N,N-diethylaminoethyl;

di(C₁–C₄-alkyl)aminocarbonyl: CO—N(CH₃)₂, CO—N(C₂H₅), CO—N(CH₂—C₂H₅)₂, CO—N[CH(CH₃)₂]₂, CO—N(n-C₄H₉)₂, CO—N[CH(CH₃)—C₂H₅]₂, CO—N[CH₂—CH(CH₃)₂]₂, CO—N[C(CH₃)₃]₂, N-ethyl-N-methylaminocarbonyl, N-methyl-N-propylaminocarbonyl, N-methyl-N—[CH(CH₃)₂]aminocarbonyl, N-butyl-N-methylaminocarbonyl, N-methyl-N-(1-methylpropyl)aminocarbonyl, N-methyl-N-(2-methylpropyl)aminocarbonyl, N—[C(CH₃)₃]—N-methylaminocarbonyl, N-ethyl-N-propylaminocarbonyl, N-ethyl-N—[CH(CH₃)₂]-aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N—[C(CH₃)₃]aminocarbonyl, N—[CH(CH₃)₂]—N-propylaminocarbonyl, N-butyl-N-propylaminocarbonyl, N-(1-methylpropyl)-N-propylaminocarbonyl, N-(2-methylpropyl)-N-propylaminocarbonyl, N—[C(CH₃)₃]—N-propylaminocarbonyl, N-butyl-N—[CH(CH₃)₂]aminocarbonyl, N—[CH(CH₃)₂]—N-(1-methylpropyl)aminocarbonyl, N—[CH(CH₃)₂]—N-(2-methylpropyl)aminocarbonyl, N—[C(CH₃)₃]—N—[CH(CH₃)₂]aminocarbonyl, N-butyl-N-(1-methylpropyl)aminocarbonyl, N-butyl-N-(2-methylpropyl)aminocarbonyl, N-butyl-N—[C(CH₃)₃]aminocarbonyl, N-(1-methylpropyl)-N-(2-methylpropyl)aminocarbonyl, N—[C(CH$_3$)$_3$]—N-(1-methylpropyl)aminocarbonyl or N—[C(CH$_3$)$_3$]—N-(2-methylpropyl)aminocarbonyl, preferably CO—N(CH$_3$)$_2$ or CO—N(C$_2$H$_5$)$_2$;

di(C$_1$–C$_4$-alkyl)aminocarbonyl-C$_1$–C$_4$-alkyl: C$_1$–C$_4$-alkyl which is substituted by di(C$_1$–C$_4$-alkyl)aminocarbonyl as mentioned above, preferably by CO—N(CH$_3$)$_2$ or CO—N(C$_2$H$_5$)$_2$, i.e., for example, CH$_2$—CO—N(CH$_3$)$_2$, CH$_2$—CO—N(C$_2$H$_5$)$_2$, CH(CH$_3$)—CO—N(CH$_3$)$_2$ oder CH(CH$_3$)—CO—N(C$_2$H$_5$)$_2$, preferably CH$_2$—CO—N(CH$_3$)$_2$ or CH(CH$_3$)—CO—N(CH$_3$)$_2$;

di(C$_1$–C$_4$-alkyl)phosphonyl: —PO(OCH$_3$)$_2$, —PO(OC$_2$H$_5$)$_2$, N,N-dipropylphosphonyl, N,N-di-(1-methylethyl)phosphonyl, N,N-dibutylphosphonyl, N,N-Di-(1-methylpropyl)phosphonyl, N,N-di-(2-methylpropyl)phosphonyl, N,N-di-(1,1-dimethylethyl)phosphonyl, N-ethyl-N-methylphosphonyl, N-methyl-N-propylphosphonyl, N-methyl-N-(1-methylethyl)phosphonyl, N-butyl-N-methylphosphonyl, N-methyl-N-(1-methylpropyl)phosphonyl, N-methyl-N-(2-methylpropyl)phosphonyl, N-(1,1-dimethylethyl)-N-methylphosphonyl, N-ethyl-N-propylphosphonyl, N-ethyl-N-(1-methylethyl)phosphonyl, N-butyl-N-ethylphosphonyl, N-ethyl-N-(1-methylpropyl)phosphonyl, N-ethyl-N-(2-methylpropyl)phosphonyl, N-ethyl-N-(1,1-dimethylethyl)phosphonyl, N-(1-methylethyl)-N-propylphosphonyl, N-butyl-N-propylphosphonyl, N-(1-methylpropyl)-N-propylphosphonyl, N-(2-methylpropyl)-N-propylphosphonyl, N-(1,1-dimethylethyl)-N-propylphosphonyl, N-butyl-N-(1-methylethyl)phosphonyl, N-(1-methylethyl)-N-(1-methylpropyl)phosphonyl, N-(1-methylethyl)-N-(2-methylpropyl)phosphonyl, N-(1,1-dimethylethyl)-N-(1-methylethyl)phosphonyl, N-butyl-N-(1-methylpropyl)phosphonyl, N-butyl-N-(2-methylpropyl)phosphonyl, N-butyl-N-(1,1-dimethylethyl)phosphonyl, N-(1-methylpropyl)-N-(2-methylpropyl)phosphonyl, N-(1,1-dimethylethyl)-N-(1-methylpropyl)phosphonyl or N-(1-dimethylethyl)-N-(2-methylpropyl)phosphonyl, preferably —PO(OCH$_3$)$_2$ or —PO(OC$_2$H$_5$)$_2$;

di(C$_1$–C$_4$-alkyl)phosphonyl-C$_1$–C$_4$-alkyl: C$_1$–C$_4$-alkyl which is substituted by di(C$_1$–C$_4$-alkyl)phosphonyl as mentioned above, preferably by —PO(OCH$_3$)$_2$ or —PO(OC$_2$H$_5$)$_2$, i.e., for example, CH$_2$—PO(OCH$_3$)$_2$, CH$_2$—PO(OC$_2$H$_5$)$_2$, CH(CH$_3$)—PO(OCH$_3$)$_2$ or CH(CH$_3$)—PO(OC$_2$H$_5$)$_2$;

C$_3$–C$_6$-alkenyl: prop-1-en-1-yl, allyl, 1-methylethenyl, 1-buten-1-yl, 1-buten-2-yl, 1-buten-3-yl, 2-buten-1-yl, 1-methylprop-1-en-1-yl, 2-methylprop-1-en-1-yl, 1-methylprop-2-en-1-yl, 2-methylprop-2-en-1-yl, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex -5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl or 1-ethyl-2-methylprop-2-en-1-yl;

C$_3$–C$_6$-haloalkenyl: C$_3$–C$_6$-alkenyl as mentioned above which is partially or fully substituted by fluorine, chlorine, bromine and/or iodine, i.e., for example, 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl or 2,3-dibromobut-2-enyl;

cyano-C$_3$–C$_6$-alkenyl: for example 2-cyanoallyl, 3-cyanoallyl, 4-cyanobut-2-enyl, 4-cyanobut-3-enyl or 5-cyanopent-4-enyl;

C$_3$–C$_6$-alkynyl: prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl and 4-methylpent-2-yn-5-yl, preferably prop-2-yn-1-yl;

C$_3$–C$_6$-haloalkynyl: C$_3$–C$_6$-alkynyl as mentioned above which is partially or fully substituted by fluorine, chlorine, bromine and/or iodine, i.e., for example, 1,1-difluoroprop-2-yn-1-yl, 4-fluorobut-2-yn-1-yl, 4-chlorobut-2-yn-1-yl, 1,1-difluorobut -2-yn-1-yl, 5-fluoropent-3-yn-1-yl or 6-fluorohex-4-yn-1-yl;

cyano-C$_3$–C$_6$-alkynyl: for example 3-cyanopropargyl, 4-cyanobut-2-yn-1-yl, 5-cyanopent-3-yn-1-yl and 6-cyanohex-4-yn-1-yl;

C$_3$–C$_4$-alkenyloxy-C$_1$–C$_4$-alkyl: C$_1$–C$_4$-alkyl which is substituted by C$_3$–C$_4$-alkenyloxy such as allyloxy, but-1-en-3-yloxy, but-1-en-4-yloxy, but-2-en-1-yloxy, 1-methylprop-2-enyloxy or 2-methylprop-2-enyloxy, i.e., for example, allyloxymethyl, 2-allyloxyethyl or but-1-en-4-yloxymethyl, in particular 2-allyloxyethyl:

C$_3$–C$_4$-alkynyloxy-C$_1$–C$_4$-alkyl: C$_1$–C$_4$-alkyl which is substituted by C$_3$–C$_4$-alkynyloxy such as propargyloxy, but-1-yn-3-yloxy, but-1-yn-4-yloxy, but-2-yn-1-yloxy, 1-methylprop-2-ynyloxy or 2-methylprop-2-ynyloxy, preferably by propargyloxy, i.e., for example, propargyloxymethyl or 2-propargyloxymethyl, in particular 2-propargyloxymethyl;

(C$_3$–C$_4$-alkenyloxy)imino-C$_1$–C$_4$-alkyl: C$_1$–C$_4$-alkyl which is substituted by (C$_3$–C$_4$-alkenyloxy)imino such as allyloxyimino, but-1-en-3-yloxyimino, but-1-en-4-yloxyimino, but-2-en-1-yloxyimino, 1-methylprop-2-enyloxyimino or 2-methylprop-2-enyloxyimino, i.e., for example, allyloxy-N=CH—CH$_2$ or but-1-en-4-yloxy-N=CH, in particular allyloxy-N=CH—CH$_2$;

C$_3$–C$_4$-alkenylthio-C$_1$–C$_4$-alkyl: C$_1$–C$_4$-alkyl which is substituted by C$_3$–C$_4$-alkenylthio such as allylthio, but-1-en- 3-ylthio, but-1-en-4-ylthio, but-2-en-1-ylthio, 1-methylprop-2-enylthio or 2-methylprop-2-enylthio, i.e., for example, allylthiomethyl, 2-allylthioethyl or but-1-en-4-ylthiomethyl, in particular 2-(allylthio)ethyl;

$C_3$–$C_4$-alkynylthio-$C_1$–$C_4$-alkyl: $C_1$–$C_4$-alkyl which is substituted by $C_3$–$C_4$-alkynylthio such as propargylthio, but-1-yn-3-ylthio, but-1-yn-4-ylthio, but-2-yn-1-ylthio, 1-methylprop-2-ynylthio or 2-methylprop-2-ynylthio, preferably by propargylthio, i.e., for example, propargylthiomethyl or 2-propargylthioethyl, in particular 2-(propargylthio)ethyl;

$C_3$–$C_4$-alkenylsulfinyl-$C_1$–$C_4$-alkyl: $C_1$–$C_4$-alkyl which is substituted by $C_3$–$C_4$-alkenylsulfinyl such as allylsulfinyl, but-1-en-3-ylsulfinyl, but-1-en-4-ylsulfinyl, but-2-en-1-ylsulfinyl, 1-methylprop-2-enylsulfinyl or 2-methylprop-2-enylsulfinyl, i.e., for example, allylsulfinylmethyl, 2-allylsulfinylethyl or but-1-en-4-ylsulfinylmethyl, in particular 2-(allylsulfinyl)ethyl;

$C_3$–$C_4$-alkynylsulfinyl-$C_1$–$C_4$-alkyl: $C_1$–$C_4$-alkyl which is substituted by $C_3$–$C_4$-alkynylsulfinyl such as propargylsulfinyl, but-1-yn-3-ylsulfinyl, but-1-yn-4-ylsulfinyl, but-2-yn-1-ylsulfinyl, 1-methylprop-2-ynylsulfinyl or 2-methylprop-2-ynylsulfinyl, preferably propargylsulfinyl, i.e., for example, propargylsulfinylmethyl or 2-propargylsulfinylethyl, in particular 2-(propargylsulfinyl)ethyl;

$C_3$–$C_4$-alkenylsulfonyl-$C_1$–$C_4$-alkyl: $C_1$–$C_4$-alkyl which is substituted by $C_3$–$C_4$-alkenylsulfonyl such as allylsulfonyl, but-1-en-3-ylsulfonyl, but-1-en-4-ylsulfonyl, but-2-en-1-ylsulfonyl, 1-methylprop-2-enylsulfonyl or 2-methylprop-2-enylsulfonyl, i.e., for example, allylsulfonylmethyl, 2-allylsulfonylethyl or but-1-en-4-ylsulfonylmethyl, in particular 2-(allylsulfonyl)ethyl;

$C_3$–$C_4$-alkynylsulfonyl-$C_1$–$C_4$-alkyl; $C_1$–$C_4$-alkyl which is substituted by $C_3$–$C_4$-alkynylsulfonyl such as propargylsulfonyl, but-1-yn-3-ylsulfonyl, but-1-yn-4-ylsulfonyl, but-2-yn-1-ylsulfonyl, 1-methylprop-2-ynylsulfonyl or 2-methylprop-2-ynylsulfonyl, preferably by propargylsulfonyl, i.e., for example, propargylsulfonylmethyl or 2-propargylsulfonylethyl, in particular 2-(propargylsulfonyl)ethyl;

$C_3$–$C_8$-cycloalkyl: cyclopropyl, cyclobutyl, cyclopentyl, cyclohexyl, cycloheptyl or cyclooctyl;

$C_3$–$C_8$-cycloalkyl-$C_1$–$C_6$-alkyl: for example cyclopropylmethyl, cyclobutylmethyl, cyclopentylmethyl, cyclohexylmethyl, cycloheptylmethyl, cyclooctylmethyl, 2-(cyclopropyl)ethyl, 2-(cyclobutyl)ethyl, 2-(cyclopentyl)ethyl, 2-(cyclohexyl)ethyl, 2-(cycloheptyl)ethyl, 2-(cyclooctyl)ethyl, 3-(cyclopropyl)propyl, 3-(cyclobutyl)propyl, 3-(cyclopentyl)propyl, 3-(cyclohexyl)propyl, 3-(cycloheptyl)propyl, 3-(cyclooctyl)propyl, 4-(cyclopropyl)butyl, 4-(cyclobutyl)butyl, 4-(cyclopentyl)butyl, 4-(cyclohexyl)butyl, 4-(cycloheptyl)butyl, 4-(cyclooctyl)butyl, 5-(cyclopropyl)pentyl, 5-(cyclobutyl)pentyl, 5-(cyclopentyl)pentyl, 5-(cyclohexyl)pentyl, 5-(cycloheptyl)pentyl, 5-(cyclooctyl)pentyl, 6-(cyclopropyl)hexyl, 6-(cyclobutyl)hexyl, 6-(cyclopentyl)hexyl, 6-(cyclohexyl)hexyl, 6-(cycloheptyl)hexyl or 6-(cyclooctyl)hexyl;

$C_3$–$C_8$-cycloalkyl, which contains a carbonyl or thiocarbonyl ring member: for example cyclobutanon-2-yl, cyclobutanon-3-yl, cyclopentanon-2-yl, cyclopentanon-3-yl, cyclohexanon-2-yl, cyclohexanon-4-yl, cycloheptanon-2-yl, cyclooctanon-2-yl, cyclobutanethion-2-yl, cyclobutanethion-3-yl, cyclopentanethion-2-yl, cyclopentanethion-3-yl, cyclohexanethion-2-yl, cyclohexanethion-4-yl, cycloheptanethion-2-yl or cyclooctanethion-2-yl, preferably cyclopentanon-2-yl or cyclohexanon-2-yl;

$C_3$–$C_8$-cycloalkyl-$C_1$–$C_4$-alkyl, which contains a carbonyl or thiocarbonyl ring member: for example cyclobutanon-2-ylmethyl, cyclobutanon-3-ylmethyl, cyclopentanon-2-ylmethyl, cyclopentanon-3-ylmethyl, cyclohexanon-2-ylmethyl, cyclohexanon-4-ylmethyl, cycloheptanon-2-ylmethyl, cyclooctanon-2-ylmethyl, cyclobutanethion-2-ylmethyl, cyclobutanethion-3-ylmethyl, cyclopentanethion-2-ylmethyl, cyclopentanethion-3-ylmethyl, cyclohexanethion-2-ylmethyl, cyclohexanethion-4-ylmethyl, cycloheptanethion-2-ylmethyl, cyclooctanethion-2-ylmethyl, 1-(cyclobutanon-2-yl)ethyl, 1-(cyclobutanon-3-yl)ethyl, 1-(cyclopentanon-2-yl)ethyl, 1-(cyclopentanon-3-yl)ethyl, 1-(cyclohexanon-2-yl)ethyl, 1-(cyclohexanon-4-yl)ethyl, 1-(cycloheptanon-2-yl)ethyl, 1-(cyclooctanon-2-yl)ethyl, 1-(cyclobutanethion-2-yl)ethyl, 1-(cyclobutanethion-3-yl)ethyl, 1-(cyclopentanethion-2-yl)ethyl, 1-(cyclopentanethion-3-yl)ethyl, 1-(cyclohexanethion-2-yl)ethyl, 1-(cyclohexanethion-4-yl)ethyl, 1-(cycloheptanethion-2-yl)ethyl, 1-(cyclooctanethion-2-yl)ethyl, 2-(cyclobutanon-2-yl)ethyl, 2-(cyclobutanon-3-yl)ethyl, 2-(cyclopentanon-2-yl)ethyl, 2-(cyclopentanon-3-yl)ethyl, 2-(cyclohexanon-2-yl)ethyl, 2-(cyclohexanon-4-yl)ethyl, 2-(cycloheptanon-2-yl)ethyl, 2-(cyclooctanon-2-yl)ethyl, 2-(cyclobutanethion-2-yl)ethyl, 2-(cyclobutanethion-3-yl)ethyl, 2-(cyclopentanethion-2-yl)ethyl, 2-(cyclopentanethion-3-yl)ethyl, 2-(cyclohexanethion-2-yl)ethyl, 2-(cyclohexanethion-4-yl)ethyl, 2-(cycloheptanethion-2-yl)ethyl, 2-(cyclooctanethion-2-yl)ethyl, 3-(cyclobutanon-2-yl)propyl, 3-(cyclobutanon-3-yl)propyl, 3-(cyclopentanon-2-yl)propyl, 3-(cyclopentanon-3-yl)propyl, 3-(cyclohexanon-2-yl)propyl, 3-(cyclohexanon-4-yl)propyl, 3-(cycloheptanon-2-yl)propyl, 3-(cyclooctanon-2-yl)propyl, 3-(cyclobutanethion-2-yl)propyl, 3-(cyclobutanethion-3-yl)propyl, 3-(cyclopentanethion-2-yl)propyl, 3-(cyclopentanethion-3-yl)propyl, 3-(cyclohexanethion-2-yl)propyl, 3-(cyclohexanethion-4-yl)propyl, 3-(cycloheptanethion-2-yl)propyl, 3-(cyclooctanethion-2-yl)propyl, 4-(cyclobutanon-2-yl)butyl, 4-(cyclobutanon-3-yl)butyl, 4-(cyclopentanon-2-yl)butyl, 4-(cyclopentanon-3-yl)butyl, 4-(cyclohexanon-2-yl)butyl, 4-(cyclohexanon-4-yl)butyl, 4-(cycloheptanon-2-yl)butyl, 4-(cyclooctanon-2-yl)butyl, 4-(cyclobutanethion-2-yl)butyl, 4-(cyclobutanethion-3-yl )butyl, 4-(cyclopentanethione-2-yl)butyl, 4-(cyclopentanethion-3-yl)butyl, 4-(cyclohexanethion-2-yl)butyl, 4-(cyclohexanethion-4-yl)butyl, 4-(cycloheptanethion-2-yl)butyl or 4-(cyclooctanethion-2-yl)butyl;

$C_3$–$C_8$-cycloalkyloxy-$C_1$–$C_4$-alkyl: cyclopropyloxymethyl, 1-cyclopropyloxyethyl, 2-cyclopropyloxyethyl, 1-cyclopropyloxyprop-1-yl, 2-cyclopropyloxyprop-1-yl, 3-cyclopropyloxyprop-1-yl, 1-cyclopropyloxybut-1-yl, 2-cyclopropyloxybut-1-yl, 3-cyclopropyloxybut-1-yl, 4-cyclopropyloxybut-1-yl, 1-cyclopropyloxybut-2-yl, 2-cyclopropyloxybut-2-yl, 3-cyclopropyloxybut-2-yl, 3-cyclopropyloxybut-2-yl, 4-cyclopropyloxybut-2-yl, 1-(cyclopropyloxymethyl)eth-1-yl, 1-(cyclopropyloxymethyl)-1-($cH_3$)-eth-1-yl, 1-(cyclopropylmethyloxy)prop-1-yl, cyclobutyloxymethyl, 1-cyclobutyloxyethyl, 2-cyclobutyloxyethyl, 1-cyclobutyloxyprop-1-yl, 2-cyclobutyloxyprop1-yl, 3-cyclobutyloxyprop-1-yl, 1-cyclobutyloxybut-1-yl, 2-cyclobutyloxybut-1-yl, 3-cyclobutyloxybut-1-yl, 4-cyclobutyloxybut-1-yl, 1-cyclobutyloxybut-2-yl, 2-cyclobutyloxybut-2-yl, 3-cyclobutyloxybut-2-yl, 3-cyclobutyloxybut-2-yl, 4-cyclobutyloxybut-2-yl, 1-(cyclobutyloxymethyl)eth-1-yl, 1-(cyclobutyloxymethyl)-1-($CH_3$)-eth-1-yl, 1-(cyclobutyloxymethyl)prop-1-yl, cyclopentyloxymethyl, 1-cyclopentyloxyethyl, 2-cyclopentyloxyethyl, 1-cyclopentyloxyprop-1-yl, 2-cyclopentyloxyprop-1-yl, 3-cyclopentyloxyprop-1-yl, 1-cyclopentyloxybut-1-yl, 2-cyclopentyloxybut-1-yl, 3-cyclopentyloxybut-1-yl, 4-cyclopentyloxybut-1-yl, 1-cyclopentyloxybut-2-yl, 2-cyclopentyloxybut-2-yl, 3-cyclopentyloxybut-2-yl, 3-cyclopentyloxybut-2-yl, 4-cyclopentyloxybut-2-yl, 1-(cyclopentyloxymethyl)eth-1-yl, 1-(cyclopentyloxymethyl)-1-($CH_3$)-eth-1-yl, 1-(cyclopentyloxymethyl)prop-1-yl, cyclohexyloxymethyl, 1-cyclohexyloxyethyl, 2-cyclohexyloxyethyl, 1-cyclohexyloxyprop-1-yl, 2-cyclohexyloxyprop-1-yl, 3-cyclohexyloxyprop-1-yl, 1-cyclohexyloxybut-1-yl, 2-cyclohexyloxybut-1-yl, 3-cyclohexyloxybut-1-yl, 4-cyclohexyloxybut-1-yl, 1-cyclohexyloxybut-2-yl, 2-cyclohexyloxybut-2-yl, 3-cyclohexyloxybut-2-yl, 3-cyclohexyloxybut-2-yl, 4-cyclohexyloxybut-2-yl, 1-(cyclohexyloxymethyl)eth-1-yl, 1-(cyclohexyloxymethyl)-1-($CH_3$)-eth-1-yl, 1-(cyclohexyloxymethyl)prop-1-yl, cycloheptyloxymethyl, 1-cycloheptyloxyethyl, 2-cycloheptyloxyethyl, 1-cycloheptyloxyprop-1-yl, 2-cycloheptyloxyprop-1-yl, 3-cycloheptyloxyprop-1-yl, 1-cycloheptyloxybut-1-yl, 2-cycloheptyloxybut-1-yl, 3-cycloheptyloxybut-1-yl, 4-cycloheptyloxybut-1-yl, 1-cycloheptyloxybut-2-yl, 2-cycloheptyloxybut-2-yl, 3-cycloheptyloxybut-2-yl, 3-cycloheptyloxybut-2-yl, 4-cycloheptyloxybut-2-yl, 1-(cycloheptyloxymethyl)eth-1-yl, 1-(cycloheptyloxymethyl)-1-($CH_3$)-eth-1-yl, 1-(cycloheptyloxymethyl)prop-1-yl, cyclooctyloxymethyl, 1-cyclooctyloxyethyl, 2-cyclooctyloxyethyl, 1-cyclooctyloxyprop-1-yl, 2-cyclooctyloxyprop-1-yl, 3-cyclooctyloxyprop-1-yl, 1-cyclooctyloxybut-1-yl, 2-cyclooctyloxybut-1-yl, 3-cyclooctyloxybut-1-yl, 4-cyclooctyloxybut-1-yl, 1-cyclooctyloxybut-2-yl, 2-cyclooctyloxybut-2-yl, 3-cyclooctyloxybut-2-yl, 3-cyclooctyloxybut-2-yl, 4-cyclooctyloxybut-2-yl, 1-(cyclooctyloxymethyl)-eth-1-yl, 1-(cyclooctyloxymethyl)-1-($CH_3$)-eth-1-yl or 1-(cyclooctyloxymethyl)prop-1-yl, in particular $C_3$–$C_6$-cycloalkoxymethyl or 2-($C_3$–$C_6$-cycloalkoxy)ethyl.

3- to 7-membered heterocyclyl is a saturated, partially or fully unsaturated or aromatic heterocycle having from one to three heteroatoms selected from a group consisting of
one to three nitrogen atoms,
one or two oxygen and
one or two sulfur atoms.

Examples of saturated heterocycles which may contain a carbonyl or thiocarbonyl ring member are:
oxiranyl, thiiranyl, aziridin-1-yl, aziridin-2-yl, diaziridin-1-yl, diaziridin-3-yl, oxetan-2-yl, oxetan-3-yl, thietan-2-yl, thietan-3-yl, azetidin-1-yl, azetidin-2-yl, azetidin-3-yl, tetrahydrofuran-2-yl, tetrahydrofuran-3-yl, tetrahydrothiophen-2-yl, tetrahydrothiophen-3-yl, pyrrolidin-1-yl, pyrrolidin-2-yl, pyrrolidin-3-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-oxazolidin-2-yl, 1,3-oxazolidin-3-yl, 1,3-oxazolidin-4-yl, 1,3-oxazolidin-5-yl, 1,2-oxazolidin-2-yl, 1,2-oxazolidin-3-yl, 1,2-oxazolidin-4-yl, 1,2-oxazolidin-5-yl, 1,3-dithiolan-2-yl, 1,3-dithiolan-4-yl, pyrrolidin-1-yl, pyrrolidin-2-yl, pyrrolidin-5-yl, tetrahydropyrazol-1-yl, tetrahydropyrazol-3-yl, tetrahydropyrazol-4-yl, tetrahydropyran-2-yl, tetrahydropyran-3-yl, tetrahydropyran-4-yl, tetrahydrothiopyran-2-yl, tetrahydrothiopyran-3-yl, tetrahydropyran-4-yl, piperidin-1-yl, piperidin-2-yl, piperidin-3-yl, piperidin-4-yl, 1,3-dioxan-2-yl, 1,3-dioxan-4-yl, 1,3-dioxan-5-yl, 1,4-dioxan-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, morpholin-2-yl, morpholin-3-yl, morpholin-4-yl, hexahydropyridazin-1-yl, hexahydropyridazin-3-yl, hexahydropyridazin-4-yl, hexahydropyrimidin-1-yl, hexahydropyrimidin-2-yl, hexahydropyrimidin-4-yl, hexahydropyrimidin-5-yl, piperazin-1-yl, piperazin-2-yl, piperazin-3-yl, hexahydro-1,3,5-triazin-1-yl, hexahydro-1,3,5-triazin-2-yl, oxepan-2-yl, oxepan-3-yl, oxepan-4-yl, thiepan-2-yl, thiepan-3-yl, thiepan-4-yl, 1,3-dioxepan-2-yl, 1,3-dioxepan-4-yl, 1,3-dioxepan-5-yl, 1,3-dioxepan-6-yl, 1,3-dithiepan-2-yl, 1,3-dithiepan-2-yl, 1,3-dithiepan-2-yl, 1,3-dithiepan-2-yl, 1,4-dioxepan-2-yl, 1,4-dioxepan-7-yl, hexahydroazepin-1-yl, hexahydroazepin-2-yl, hexahydroazepin-3-yl, hexahydroazepin-4-yl, hexahydro-1,3-diazepin-1-yl, hexahydro-1,3-diazepin-2-yl, hexahydro-1,3-diazepin-4-yl, hexahydro-1,4-diazepin-1-yl und hexahydro-1,4-diazepin-2-yl.

Examples of unsaturated heterocycles which may contain a carbonyl or thiocarbonyl ring member are:
dihydrofuran-2-yl, 1,2-oxazolin-3-yl, 1,2-oxazolin-5-yl, 1,3-oxazolin-2-yl.

Preferred heteroaromatics are the 5-and 6-membered heteroaromatics, i.e., for example,
furyl, such as 2-furyl and 3-furyl, thienyl, such as 2-thienyl and 3-thienyl, pyrrolyl, such as 2-pyrrolyl and 3-pyrrolyl, isoxazolyl, such as 3-isoxazolyl, 4-isoxazolyl and 5-isoxazolyl, isothiazolyl, such as 3-isothiazolyl, 4-isothiazolyl and 5-isothiazolyl, pyrazolyl, such as 3-pyrazolyl, 4-pyrazolyl and 5-pyrazolyl, oxazolyl, such as 2-oxazolyl, 4-oxazolyl and 5-oxazolyl, thiazolyl, such as 2-thiazolyl, 4-thiazolyl and 5-thiazolyl, imidazolyl, such as 2-imidazolyl and 4-imidazolyl, oxadiazolyl, such as 1,2,4-oxadiazol-3-yl, 1,2,4-oxadiazol-5-yl and 1,3,4-oxadiazol-2-yl, thiadiazolyl, such as 1,2,4-thiadiazol-3-yl, 1,2,4-thiadiazol-5-yl and 1,3,4-thiadiazol-2-yl, triazolyl, such as 1,2,4-triazol-1-yl, 1,2,4-triazol-3-yl and 1,2,4-triazol-4-yl, pyridinyl, such as 2-pyridinyl, 3-pyridinyl and 4-pyridinyl, pyridazinyl, such as 3-pyridazinyl and 4-pyridazinyl, pyrimidinyl, such as 2-pyrimidinyl, 4-pyrimidinyl and 5-pyrimidinyl, furthermore 2-pyrazinyl, 1,3,5-triazin-2-yl and 1,2,4-triazin-3-yl, in particular pyridyl, pyrimidyl, furanyl and thienyl.

All phenyl, carboxylic and heterocyclic rings are preferably unsubstituted or carry one substituent.

Preferred with a view to the use of the substituted (4-bromopyrazol-3-yl)benzazoles I as herbicides or desiccants/defoliants are those compounds I where the variables have the following meanings, in each case either on their own or in combination:

$R^1$ is $C_1$–$C_4$-alkyl, in particular methyl;

$R^2$ is $C_1$–$C_4$-haloalkyl, $C_1$–$C_4$-haloalkoxy or $C_1$–$C_4$-alkylsulfonyl, in particular $C_1$–$C_4$-haloalkoxy or $C_1$–$C_4$-alkylsulfonyl, particularly preferably difluoromethoxy;

$R^4$ is hydrogen, fluorine or chlorine, in particular fluorine or chlorine;

$R^5$ is cyano, halogen or trifluoromethyl, in particular halogen, particularly preferably chlorine;

A is a group —N=C($XR^6$)—O— or —N=C($XR^6$)—S— which is attached to α via oxygen and sulfur, respectively, in particular —N=C($XR^6$)—O— which is attached to α via the oxygen;

X is a chemical bond, oxygen, sulfur, —NH— or —N($R^7$)—;

$R^6$, $R^7$ independently of one another are each $C_1$–$C_6$-alkyl, $C_1$–$C_6$-haloalkyl, cyano-$C_1$–$C_4$-alkyl, hydroxy-$C_1$–$C_4$-alkyl, $C_3$–$C_6$-alkenyl, $C_3$–$C_6$-alkynyl, $C_1$–$C_4$-alkoxy-$C_1$–$C_4$-alkyl, $C_1$–$C_4$-alkylthio-$C_1$–$C_4$-alkyl, $C_1$–$C_4$-alkylsulfonyl-$C_1$–$C_4$-alkyl, ($C_1$–$C_4$-alkoxy)carbonyl-$C_1$–$C_4$-alkyl, di($C_1$–$C_4$-alkyl)aminocarbonyl-$C_1$–$C_4$-alkyl, $C_3$–$C_8$-cycloalkyl, $C_3$–$C_8$-cycloalkyl-$C_1$–$C_4$-alkyl, phenyl or phenyl-$C_1$–$C_4$-alkyl; if X is a chemical bond, oxygen, sulfur, —NH— or —N($R^7$)—, $R^6$ may also be ($C_1$–$C_4$-alkyl)carbonyl or $C_1$–$C_4$-alkylsulfonyl; if X is a chemical bond, $R^6$ may furthermore be hydrogen, cyano, amino, halogen or —CH=CH—$R^8$;

$R^6$, $R^7$ are in each case in particular $C_1$–$C_6$-alkyl, hydroxy-$C_1$–$C_4$-alkyl, $C_3$–$C_6$-alkenyl, $C_3$–$C_6$-alkynyl or ($C_1$–$C_4$-alkoxy)carbonyl-$C_1$–$C_4$-alkyl; if X is a chemical bond, $R^6$ may furthermore be in particular hydrogen or —CH=CH—$R^8$;

$R^8$ is ($C_1$–$C_4$-alkoxy)carbonyl.

Very particular preference is given to the substituted (4-bromopyrazol-3-yl)benzazoles of the formula Ia (=I where $R^1$=methyl, $R^2$=difluoromethoxy, $R^4$=hydrogen, $R^5$=chlorine, Z=—N=C($XR^6$)—S— which is attached to α via the sulfur), in particular to the compounds listed in Table 1 below:

TABLE 1

| No. | -$XR^6$ |
|---|---|
| Ia.001 | —H |
| Ia.002 | —$CH_3$ |
| Ia.003 | —$C_2H_5$ |
| Ia.004 | -(n-$C_3H_7$) |
| Ia.005 | —CH($CH_3$)$_2$ |
| Ia.006 | -(n-$C_4H_9$) |
| Ia.007 | —$CH_2$—CH($CH_3$)$_2$ |
| Ia.008 | —CH($CH_3$)—$C_2H_5$ |
| Ia.009 | —C($CH_3$)$_3$ |
| Ia.010 | —$CH_2$—CH=$CH_2$ |
| Ia.011 | —$CH_2$—CH=CH—$CH_3$ |
| Ia.012 | —$CH_2$—$CH_2$—CH=$CH_2$ |
| Ia.013 | —$CH_2$—C≡CH |
| Ia.014 | —$CH_2$—$OCH_3$ |
| Ia.015 | —$CH_2$—$CH_2$—$OCH_3$ |
| Ia.016 | —$CH_2$—CN |
| Ia.017 | —$CH_2$—$CH_2$F |
| Ia.018 | —$CH_2$—$CF_3$ |
| Ia.019 | —$CH_2$—$CH_2$Cl |
| Ia.020 | —$CH_2$—CO—$OCH_3$ |
| Ia.021 | —$CH_2$—CO—$OC_2H_5$ |
| Ia.022 | —$CH_2$—CO—N($CH_3$)$_2$ |
| Ia.023 | —$CH_2$—CH(=N—$OCH_3$) |
| Ia.024 | —$CH_2$—CH(=N—$OC_2H_5$) |
| Ia.025 | —$CH_2$—CH[=N—O(n-$C_3H_7$)] |
| Ia.026 | —$CH_2$—CH[=N—OCH($CH_3$)$_2$] |
| Ia.027 | —$CH_2$—CH[=N—O(n-$C_4H_9$)] |
| Ia.028 | —$CH_2$—CH(=N—$OCH_2$—CH=$CH_2$) |
| Ia.029 | —cyclobutyl |
| Ia.030 | —cyclopentyl |
| Ia.031 | —cyclohexyl |
| Ia.032 | —phenyl |
| Ia.033 | —$CH_2$—cyclobutyl |
| Ia.034 | —$CH_2$—cyclopentyl |
| Ia.035 | —$CH_2$—cyclohexyl |
| Ia.036 | —$CH_2$—phenyl |
| Ia.037 | —$NO_2$ |
| Ia.038 | —CN |
| Ia.039 | —F |
| Ia.040 | —Cl |
| Ia.041 | —Br |
| Ia.042 | —$OCH_3$ |
| Ia.043 | —$OC_2H_5$ |
| Ia.044 | —O(n-$C_3H_7$) |
| Ia.045 | —OCH($CH_3$)$_2$ |
| Ia.046 | —O(n-$C_4H_9$) |
| Ia.047 | —$OCH_2$—CH($CH_3$)$_2$ |
| Ia.048 | —OCH($CH_3$)—$C_2H_5$ |
| Ia.049 | —OC($CH_3$)$_3$ |
| Ia.050 | —$OCH_2$—CH=$CH_2$ |
| Ia.051 | —$OCH_2$—CH=CH—$CH_3$ |
| Ia.052 | —$CH_2$—$CH_2$—CH=$CH_2$ |
| Ia.053 | —OCH($CH_3$)—CH=$CH_2$ |
| Ia.054 | —$OCH_2$—C≡CH |
| Ia.055 | —OCH($CH_3$)—C≡CH |
| Ia.056 | —$OCH_2$—$OCH_3$ |
| Ia.057 | —$OCH_2$—$CH_2$—$OCH_3$ |
| Ia.058 | —$OCH_2$—CN |
| Ia.059 | —$OCH_2$—$CH_2$F |
| Ia.060 | —$OCH_2$—$CF_3$ |
| Ia.061 | —$OCH_2$—CO—$OCH_3$ |
| Ia.062 | —$OCH_2$—CO—$OC_2H_5$ |
| Ia.063 | —$OCH_2$—CO—N($CH_3$)$_2$ |
| Ia.064 | —$OCH_2$—CH(=N—$OCH_3$) |
| Ia.065 | —$OCH_2$—CH(=N—$OC_2H_5$) |
| Ia.066 | —$OCH_2$—CH[=N—O(n-$C_3H_7$)] |
| Ia.067 | —$OCH_2$—CH[=N—OCH($CH_3$)$_2$] |
| Ia.068 | —$OCH_2$—CH[=N—O(n-$C_4H_9$)] |
| Ia.069 | —$OCH_2$—CH(=N—$OCH_2$—CH=$CH_2$) |
| Ia.070 | —O—cyclobutyl |
| Ia.071 | —O—cyclopentyl |
| Ia.072 | —O—cyclohexyl |
| Ia.073 | —O—phenyl |
| Ia.074 | —$OCH_2$—cyclobutyl |
| Ia.075 | —$OCH_2$—cyclopentyl |
| Ia.076 | —$OCH_2$—cyclohexyl |
| Ia.077 | —$OCH_2$—phenyl |
| Ia.078 | —$CH_2$—OH |
| Ia.079 | —$CH_2$—$OCH_3$ |
| Ia.080 | —$NH_2$ |
| Ia.081 | —NH—$CH_3$ |
| Ia.082 | —N($CH_3$)$_2$ |
| Ia.083 | —NH—$C_2H_5$ |
| Ia.084 | —N($C_2H_5$)$_2$ |
| Ia.085 | —NH-(n-$C_3H_7$) |
| Ia.086 | —N(n-$C_3H_7$)$_2$ |
| Ia.087 | —NH-(n-$C_4H_9$) |
| Ia.088 | —N(n-$C_4H_9$)$_2$ |
| Ia.089 | —NH—CH($CH_3$)$_2$ |
| Ia.090 | —N[CH($CH_3$)$_2$]$_2$ |
| Ia.091 | —NH—$CH_2$—CH($CH_3$)$_2$ |
| Ia.092 | —N[$CH_2$—CH($CH_3$)$_2$]$_2$ |
| Ia.093 | —NH—$CH_2$—CH=$CH_2$ |
| Ia.094 | —N($CH_2$—CH=$CH_2$)$_2$ |
| Ia.095 | —NH—$CH_2$—C≡CH |
| Ia.096 | —N($CH_2$—C≡CH)$_2$ |
| Ia.097 | —$CH_2$—N($CH_3$)$_2$ |
| Ia.098 | —SH |
| Ia.099 | —$SCH_3$ |
| Ia.100 | —$SC_2H_5$ |

TABLE 1-continued

| | |
|---|---|
| Ia.101 | —S(n-C$_3$H$_7$) |
| Ia.102 | —S(n-C$_4$H$_9$) |
| Ia.103 | —SCH(CH$_3$)$_2$ |
| Ia.104 | —SCH$_2$—CH(CH$_3$)$_2$ |
| Ia.105 | —SCH(CH$_3$)—C$_2$H$_5$ |
| Ia.106 | —SC(CH$_3$)$_3$ |
| Ia.107 | —SCH$_2$—CH=CH$_2$ |
| Ia.108 | —SCH$_2$—CH=CH—CH$_3$ |
| Ia.109 | —SCH$_2$—CH$_2$—CH=CH$_2$ |
| Ia.110 | —SCH(CH$_3$)—CH=CH$_2$ |
| Ia.111 | —SCH$_2$—C≡CH |
| Ia.112 | —SCH(CH$_3$)—C≡CH |
| Ia.113 | —SCH$_2$—OCH$_3$ |
| Ia.114 | —SCH$_2$—CH$_2$—OCH$_3$ |
| Ia.115 | —SCH$_2$—CN |
| Ia.116 | —SCH$_2$—CH$_2$F |
| Ia.117 | —SCH$_2$—CF$_3$ |
| Ia.118 | —SCH$_2$—CH$_2$Cl |
| Ia.119 | —SCH$_2$—CO—OCH$_3$ |
| Ia.120 | —SCH$_2$—CO—OC$_2$H$_5$ |
| Ia.121 | —SCH$_2$—CO—N(CH$_3$)$_2$ |
| Ia.122 | —SCH$_2$—CH(=N—OCH$_3$) |
| Ia.123 | —SCH$_2$—CH(=N—OC$_2$H$_5$) |
| Ia.124 | —SCH$_2$—CH[=N—O(n-C$_3$H$_7$)] |
| Ia.125 | —SCH$_2$—CH[=N—OCH(CH$_3$)$_2$] |
| Ia.126 | —SCH$_2$—CH[=N—O(n-C$_4$H$_9$)] |
| Ia.127 | —SCH$_2$—CH(=N—OCH$_2$—CH=CH$_2$) |
| Ia.128 | —S—cyclobutyl |
| Ia.129 | —S—cyclopentyl |
| Ia.130 | —S—cyclohexyl |
| Ia.131 | —S—phenyl |
| Ia.132 | —SCH$_2$—cyclobutyl |
| Ia.133 | —SCH$_2$—cyclopentyl |
| Ia.134 | —SCH$_2$—cyclohexyl |
| Ia.135 | —SCH$_2$—phenyl |
| Ia.136 | —CH$_2$—SCH$_3$ |
| Ia.137 | —SO—CH$_3$ |
| Ia.138 | —SO—C$_2$H$_5$ |
| Ia.139 | —SO-(n-C$_3$H$_7$) |
| Ia.140 | —SO-(n-C$_4$H$_9$) |
| Ia.141 | —SO—CH(CH$_3$)$_2$ |
| Ia.142 | —SO—CH$_2$—CH(CH$_3$)$_2$ |
| Ia.143 | —SO—CH(CH$_3$)—C$_2$H$_5$ |
| Ia.144 | —SO—C(CH$_3$)$_3$ |
| Ia.145 | —SO—CH$_2$—CH=CH$_2$ |
| Ia.146 | —SO—CH$_2$—CH=CH—CH$_3$ |
| Ia.147 | —SO—CH$_2$—CH$_2$—CH=CH$_2$ |
| Ia.148 | —SO—CH(CH$_3$)—CH=CH$_2$ |
| Ia.149 | —SO—CH$_2$—C≡CH |
| Ia.150 | —SO—CH(CH$_3$)—C≡CH |
| Ia.151 | —SO—CH$_2$—OCH$_3$ |
| Ia.152 | —SO—CH$_2$—CH$_2$—OCH$_3$ |
| Ia.153 | —SO—CH$_2$—CN |
| Ia.154 | —SO—CH$_2$—CH$_2$F |
| Ia.155 | —SO—CH$_2$—CF$_3$ |
| Ia.156 | —SO—CH$_2$—CH$_2$Cl |
| Ia.157 | —SO—CH$_2$—CO—OCH$_3$ |
| Ia.158 | —SO—CH$_2$—CO—OC$_2$H$_5$ |
| Ia.159 | —SO—CH$_2$—CO—N(CH$_3$)$_2$ |
| Ia.160 | —SO—CH$_2$—CH(=N—OCH$_3$) |
| Ia.161 | —SO—CH$_2$—CH(=N—OC$_2$H$_5$) |
| Ia.162 | —SO—CH$_2$—CH[=N—O(n-C$_3$H$_7$)] |
| Ia.163 | —SO—CH$_2$—CH[=N—OCH(CH$_3$)$_2$] |
| Ia.164 | —SO—CH$_2$—CH[=N—O(n-C$_4$H$_9$)] |
| Ia.165 | —SO—CH$_2$—CH(=N—OCH$_2$—CH=CH$_2$) |
| Ia.166 | —SO—cyclobutyl |
| Ia.167 | —SO—cyclopentyl |
| Ia.168 | —SO—cyclohexyl |
| Ia.169 | —SO—phenyl |
| Ia.170 | —SO—CH$_2$—cyclobutyl |
| Ia.171 | —SO—CH$_2$—cyclopentyl |
| Ia.172 | —SO—CH$_2$—cyclohexyl |
| Ia.173 | —SO—CH$_2$—phenyl |
| Ia.174 | —CH$_2$—SO—CH$_3$ |
| Ia.175 | —SO$_2$—CH$_3$ |
| Ia.176 | —SO$_2$—C$_2$H$_5$ |
| Ia.177 | —SO$_2$-(n-C$_3$H$_7$) |
| Ia.178 | —SO$_2$-(n-C$_4$H$_9$) |
| Ia.179 | —SO$_2$—CH(CH$_3$)$_2$ |
| Ia.180 | —SO$_2$—CH$_2$—CH(CH$_3$)$_2$ |
| Ia.181 | —SO$_2$—CH(CH$_3$)—C$_2$H$_5$ |
| Ia.182 | —SO$_2$—C(CH$_3$)$_3$ |
| Ia.183 | —SO$_2$—CH$_2$—CH=CH$_2$ |
| Ia.184 | —SO$_2$—CH$_2$—CH=CH—CH$_3$ |
| Ia.185 | —SO$_2$—CH$_2$—CH$_2$—CH=CH$_2$ |
| Ia.186 | —SO$_2$—CH(CH$_3$)—CH=CH$_2$ |
| Ia.187 | —SO$_2$—CH$_2$—C≡CH |
| Ia.188 | —SO$_2$—CH(CH$_3$)—C≡CH |
| Ia.189 | —SO$_2$—CH$_2$—OCH$_3$ |
| Ia.190 | —SO$_2$—CH$_2$—CH$_2$—OCH$_3$ |
| Ia.191 | —SO$_2$—CH$_2$—CN |
| Ia.192 | —SO$_2$—CH$_2$—CH$_2$F |
| Ia.193 | —SO$_2$—CH$_2$—CF$_3$ |
| Ia.194 | —SO$_2$—CH$_2$—CH$_2$Cl |
| Ia.195 | —SO$_2$—CH$_2$—CO—OCH$_3$ |
| Ia.196 | —SO$_2$—CH$_2$—CO—OC$_2$H$_5$ |
| Ia.197 | —SO$_2$—CH$_2$—CO—N(CH$_3$)$_2$ |
| Ia.198 | —SO$_2$—CH$_2$—CH(=N—OCH$_3$) |
| Ia.199 | —SO$_2$—CH$_2$—CH(=N—OC$_2$H$_5$) |
| Ia.200 | —SO$_2$—CH$_2$—CH[=N—O(n-C$_3$H$_7$)] |
| Ia.201 | —SO$_2$—CH$_2$—CH[=N—OCH(CH$_3$)$_2$] |
| Ia.202 | —SO$_2$—CH$_2$—CH[=N—O(n-C$_4$H$_9$)] |
| Ia.203 | —SO$_2$—CH$_2$—CH(=N—OCH$_2$—CH=CH$_2$) |
| Ia.204 | —SO$_2$—cyclobutyl |
| Ia.205 | —SO$_2$—cyclopentyl |
| Ia.206 | —SO$_2$—cyclohexyl |
| Ia.207 | —SO$_2$—phenyl |
| Ia.208 | —SO$_2$—CH$_2$—cyclobutyl |
| Ia.209 | —SO$_2$—CH$_2$—cyclopentyl |
| Ia.210 | —SO$_2$—CH$_2$—cyclohexyl |
| Ia.211 | —SO$_2$—CH$_2$—phenyl |
| Ia.212 | —CH$_2$—SO$_2$—CH$_3$ |
| Ia.213 | —CH$_2$—CH(Cl)—CO—OH |
| Ia.214 | —CH$_2$—CH(Cl)—CO—OCH$_3$ |
| Ia.215 | —CH$_2$—CH(Cl)—CO—OC$_2$H$_5$ |
| Ia.216 | —CH$_2$—CH(Cl)—CO—O(n-C$_3$H$_7$) |
| Ia.217 | —CH$_2$—CH(Cl)—CO—O(n-C$_4$H$_9$) |
| Ia.218 | —CH$_2$—CH(Cl)—CO—OCH(CH$_3$)$_2$ |
| Ia.219 | —CH$_2$—CH(Cl)—CO—OCH$_2$—CH(CH$_3$)$_2$ |
| Ia.220 | —CH$_2$—CH(Cl)—CO—OCH(CH$_3$)—C$_2$H$_5$ |
| Ia.221 | —CH$_2$—CH(Cl)—CO—OC(CH$_3$)$_3$ |
| Ia.222 | —CH$_2$—CH(Br)—CO—OH |
| Ia.223 | —CH$_2$—CH(Br)—CO—OCH$_3$ |
| Ia.224 | —CH$_2$—CH(Br)—CO—OC$_2$H$_5$ |
| Ia.225 | —CH$_2$—CH(Br)—CO—O(n-C$_3$H$_7$) |
| Ia.226 | —CH$_2$—CH(Br)—CO—O(n-C$_4$H$_9$) |
| Ia.227 | —CH$_2$—CH(Br)—CO—OCH(CH$_3$)$_2$ |
| Ia.228 | —CH$_2$—CH(Br)—CO—OCH$_2$—CH(CH$_3$)$_2$ |
| Ia.229 | —CH$_2$—CH(Br)—CO—OCH(CH$_3$)—C$_2$H$_5$ |
| Ia.230 | —CH$_2$—CH(Br)—CO—OC(CH$_3$)$_3$ |
| Ia.231 | —CH=CH—CO—OH |
| Ia.232 | —CH=CH—CO—OCH$_3$ |
| Ia.233 | —CH=CH—CO—OC$_2$H$_5$ |
| Ia.234 | —CH=CH—CO—O(n-C$_3$H$_7$) |
| Ia.235 | —CH=CH—CO—O(n-C$_4$H$_9$) |
| Ia.236 | —CH=CH—CO—OCH(CH$_3$)$_2$ |
| Ia.237 | —CH=CH—CO—OCH$_2$—CH(CH$_3$)$_2$ |
| Ia.238 | —CH=CH—CO—OCH(CH$_3$)—C$_2$H$_5$ |
| Ia.239 | —CH=CH—CO—OC(CH$_3$)$_3$ |
| Ia.240 | —CH=C(Cl)—CO—OH |
| Ia.241 | —CH=C(Cl)—CO—OCH$_3$ |
| Ia.242 | —CH=C(Cl)—CO—OC$_2$H$_5$ |
| Ia.243 | —CH=C(Cl)—CO—O(n-C$_3$H$_7$) |
| Ia.244 | —CH=C(Cl)—CO—O(n-C$_4$H$_9$) |
| Ia.245 | —CH=C(Cl)—CO—OCH(CH$_3$)$_2$ |
| Ia.246 | —CH=C(Cl)—CO—OCH$_2$—CH(CH$_3$)$_2$ |
| Ia.247 | —CH=C(Cl)—CO—OCH(CH$_3$)—C$_2$H$_5$ |
| Ia.248 | —CH=C(Cl)—CO—OC(CH$_3$)$_3$ |
| Ia.249 | —CH=C(Br)—CO—OH |
| Ia.250 | —CH=C(Br)—CO—OCH$_3$ |
| Ia.251 | —CH=C(Br)—CO—OC$_2$H$_5$ |
| Ia.252 | —CH=C(Br)—CO—O(n-C$_3$H$_7$) |
| Ia.253 | —CH=C(Br)—CO—O(n-C$_4$H$_9$) |
| Ia.254 | —CH=C(Br)—CO—OCH(CH$_3$)$_2$ |
| Ia.255 | —CH=C(Br)—CO—OCH$_2$—CH(CH$_3$)$_2$ |
| Ia.256 | —CH=C(Br)—CO—OCH(CH$_3$)—C$_2$H$_5$ |
| Ia.257 | —CH=C(Br)—CO—OC(CH$_3$)$_3$ |
| Ia.258 | —CH$_2$—CH(Cl)—CO—NH$_2$ |

TABLE 1-continued

| | |
|---|---|
| Ia.259 | —CH$_2$—CH(Cl)—CO—NH—CH$_3$ |
| Ia.260 | —CH$_2$—CH(Cl)—CO—N(CH$_3$)$_2$ |
| Ia.261 | —CH$_2$—CH(Cl)—CO—NH—C$_2$H$_5$ |
| Ia.262 | —CH$_2$—CH(Cl)—CO—N(C$_2$H$_5$)$_2$ |
| Ia.263 | —CH$_2$—CH(Cl)—CO—NH-(n-C$_3$H$_7$) |
| Ia.264 | —CH$_2$—CH(Cl)—CO—N(n-C$_3$H$_7$)$_2$ |
| Ia.265 | —CH$_2$—CH(Cl)—CO—NH-(n-C$_4$H$_9$) |
| Ia.266 | —CH$_2$—CH(Cl)—CO—N(n-C$_4$H$_9$)$_2$ |
| Ia.267 | —CH$_2$—CH(Br)—CO—NH$_2$ |
| Ia.268 | —CH$_2$—CH(Br)—CO—NH—CH$_3$ |
| Ia.269 | —CH$_2$—CH(Br)—CO—N(CH$_3$)$_2$ |
| Ia.270 | —CH$_2$—CH(Br)—CO—NH—C$_2$H$_5$ |
| Ia.271 | —CH$_2$—CH(Br)—CO—N(C$_2$H$_5$)$_2$ |
| Ia.272 | —CH$_2$—CH(Br)—CO—NH-(n-C$_3$H$_7$) |
| Ia.273 | —CH$_2$—CH(Br)—CO—N(n-C$_3$H$_7$)$_2$ |
| Ia.274 | —CH$_2$—CH(Br)—CO—NH-(n-C$_4$H$_9$) |
| Ia.275 | —CH$_2$—CH(Br)—CO—N(n-C$_4$H$_9$)$_2$ |
| Ia.276 | —CH=CH—CO—NH$_2$ |
| Ia.277 | —CH=CH—CO—NH—CH$_3$ |
| Ia.278 | —CH=CH—CO—N(CH$_3$)$_2$ |
| Ia.279 | —CH=CH—CO—NH—C$_2$H$_5$ |
| Ia.280 | —CH=CH—CO—N(C$_2$H$_5$)$_2$ |
| Ia.281 | —CH=CH—CO—NH-(n-C$_3$H$_7$) |
| Ia.282 | —CH=CH—CO—N(n-C$_3$H$_7$)$_2$ |
| Ia.283 | —CH=CH—CO—NH-(n-C$_4$H$_9$) |
| Ia.284 | —CH=CH—CO—N(n-C$_4$H$_9$)$_2$ |
| Ia.285 | —CH=C(Cl)—CO—NH$_2$ |
| Ia.286 | —CH=C(Cl)—CO—NH—CH$_3$ |
| Ia.287 | —CH=C(Cl)—CO—N(CH$_3$)$_2$ |
| Ia.288 | —CH=C(Cl)—CO—NH—C$_2$H$_5$ |
| Ia.289 | —CH=C(Cl)—CO—N(C$_2$H$_5$)$_2$ |
| Ia.290 | —CH=C(Cl)—CO—NH-(n-C$_3$H$_7$) |
| Ia.291 | —CH=C(Cl)—CO—N(n-C$_3$H$_7$)$_2$ |
| Ia.292 | —CH=C(Cl)—CO—NH-(n-C$_4$H$_9$) |
| Ia.293 | —CH=C(Cl)—CO—N(n-C$_4$H$_9$)$_2$ |
| Ia.294 | —CH=C(Br)—CO—NH$_2$ |
| Ia.295 | —CH=C(Br)—CO—NH—CH$_3$ |
| Ia.296 | —CH=C(Br)—CO—NH(CH$_3$)$_2$ |
| Ia.297 | —CH=C(Br)—CO—NH—C$_2$H$_5$ |
| Ia.298 | —CH=C(Br)—CO—N(C$_2$H$_5$)$_2$ |
| Ia.299 | —CH=C(Br)—CO—NH-(n-C$_3$H$_7$) |
| Ia.300 | —CH=C(Br)—CO—N(n-C$_3$H$_7$)$_2$ |
| Ia.301 | —CH=C(Br)—CO—NH-(n-C$_4$H$_9$) |
| Ia.302 | —CH=C(Br)—CO—N(n-C$_4$H$_9$)$_2$ |
| Ia.303 | —CH(CH$_3$)—OCH$_3$ |
| Ia.304 | —CH$_2$Cl |
| Ia.305 | —CF$_3$ |
| Ia.306 | —CH$_2$OH |
| Ia.307 | —CH(CH$_3$)OH |
| Ia.308 | —CH$_2$—CH$_2$OH |
| Ia.309 | —O—phenyl |
| Ia.310 | —OCH$_2$—phenyl |
| Ia.311 | —OCH$_2$—CO—O(n-C$_3$H$_7$) |
| Ia.312 | —OCH$_2$—CO—OCH(CH$_3$)$_2$ |
| Ia.313 | —OCH$_2$—CO—O(n-C$_4$H$_9$) |
| Ia.314 | —OCH$_2$—CO—OCH$_2$—CH(CH$_3$)$_2$ |
| Ia.315 | —OCH$_2$—CO—OCH(CH$_3$)—C$_2$H$_5$ |
| Ia.316 | —OCH$_2$—CO—OC(CH$_3$)$_3$ |
| Ia.317 | —O—CO—CH$_3$ |
| Ia.318 | —O—CO—C$_2$H$_5$ |
| Ia.319 | —O—CO-(n-C$_3$H$_7$) |
| Ia.320 | —O—CO-(n-C$_4$H$_9$) |
| Ia.321 | —OCH(CH$_3$)—CO—OCH$_3$ |
| Ia.322 | —OCH(CH$_3$)—CO—OC$_2$H$_5$ |
| Ia.323 | —OCH(CH$_3$)—CO—O(n-C$_3$H$_7$) |
| Ia.324 | —OCH(CH$_3$)—CO—OCH(CH$_3$)$_2$ |
| Ia.325 | —OCH(CH$_3$)—CO—O(n-C$_4$H$_9$) |
| Ia.326 | —OCH(CH$_3$)—CO—OCH$_2$—CH(CH$_3$)$_2$ |
| Ia.327 | —OCH(CH$_3$)—CO—OCH(CH$_3$)—C$_2$H$_5$ |
| Ia.328 | —OCH(CH$_3$)—CO—OC(CH$_3$)$_3$ |
| Ia.329 | —NH—CH$_2$—CH$_2$—CN |
| Ia.330 | —N(CH$_2$—CH$_2$—CN)$_2$ |
| Ia.331 | —NH—CH$_2$—CO—OCH$_3$ |
| Ia.332 | —N(CH$_2$—CO—OCH$_3$)$_2$ |
| Ia.333 | —NH—CH$_2$—CO—OC$_2$H$_5$ |
| Ia.334 | —N(CH$_2$—CO—OC$_2$H$_5$)$_2$ |
| Ia.335 | —N(CH$_3$)—C$_2$H$_5$ |
| Ia.336 | —N(CH$_3$)-(n-C$_3$H$_7$) |
| Ia.337 | —N(CH$_3$)-(n-C$_4$H$_9$) |
| Ia.338 | —N(CH$_3$)—CH(CH$_3$)$_2$ |
| Ia.339 | —N(CH$_3$)—CH$_2$—CH(CH$_3$)$_2$ |
| Ia.340 | —N(CH$_3$)—CH$_2$—CH=CH$_2$ |
| Ia.341 | —N(CH$_3$)—CH$_2$—C≡CH |
| Ia.342 | —N(CH$_3$)—CH$_2$—CH$_2$—CN |
| Ia.343 | —N(CH$_3$)—CH$_2$—CO—OCH$_3$ |
| Ia.344 | —N(CH$_3$)—CH$_2$—CO—OC$_2$H$_5$ |
| Ia.345 | —NH—CO—CH$_3$ |
| Ia.346 | —NH—CO—C$_2$H$_5$ |
| Ia.347 | —NH—CO-(n-C$_3$H$_7$) |
| Ia.348 | —NH—CO-(n-C$_4$H$_9$) |
| Ia.349 | —NH—SO$_2$—CH$_3$ |
| Ia.350 | —NH—SO$_2$—C$_2$H$_5$ |
| Ia.351 | —NH—SO$_2$-(n-C$_3$H$_7$) |
| Ia.352 | —NH—SO$_2$-(n-C$_4$H$_9$) |
| Ia.353 | —S—phenyl |
| Ia.354 | —SCH$_2$—phenyl |
| Ia.355 | —SCH$_2$—CO—O(n-C$_3$H$_7$) |
| Ia.356 | —SCH$_2$—CO—OCH(CH$_3$)$_2$ |
| Ia.357 | —SCH$_2$—CO—O(n-C$_4$H$_9$) |
| Ia.358 | —SCH$_2$—CO—OCH$_2$—CH(CH$_3$)$_2$ |
| Ia.359 | —SCH$_2$—CO—OCH(CH$_3$)—C$_2$H$_5$ |
| Ia.360 | —SCH$_2$—CO—OC(CH$_3$)$_3$ |
| Ia.361 | —S—CO—CH$_3$ |
| Ia.362 | —SCH(CH$_3$)—CO—OCH$_3$ |
| Ia.363 | —SCH(CH$_3$)—CO—OC$_2$H$_5$ |
| Ia.364 | —SCH(CH$_3$)—CO—O(n-C$_3$H$_7$) |
| Ia.365 | —SCH(CH$_3$)—CO—O(n-C$_4$H$_9$) |
| Ia.366 | —CH$_2$—PO(OCH$_3$)$_2$ |
| Ia.367 | —CH$_2$—PO(OC$_2$H$_5$)$_2$ |
| Ia.368 | —OCH$_2$—PO(OCH$_3$)$_2$ |
| Ia.369 | —OCH$_2$—PO(OC$_2$H$_5$)$_2$ |
| Ia.370 | —SCH$_2$—PO(OCH$_3$)$_2$ |
| Ia.371 | —SCH$_2$—PO(OC$_2$H$_5$)$_2$ |
| Ia.372 | —CH$_2$—CH(Cl)—PO(OCH$_3$)$_2$ |
| Ia.373 | —CH$_2$—CH(Cl)—PO(OC$_2$H$_5$)$_2$ |
| Ia.374 | —CH$_2$—CH(Br)—PO(OCH$_3$)$_2$ |
| Ia.375 | —CH$_2$—CH(Br)—PO(OC$_2$H$_5$)$_2$ |
| Ia.376 | —CH=CH—PO(OCH$_3$)$_2$ |
| Ia.377 | —CH=CH—PO(OC$_2$H$_5$)$_2$ |
| Ia.378 | —CH(CO—OCH$_3$)$_2$ |
| Ia.379 | —CH(CO—OC$_2$H$_5$)$_2$ |
| Ia.380 | —CH(CO—OCH$_3$)[CO—OC(CH$_3$)$_3$] |
| Ia.381 | —CH(CO—OC$_2$H$_5$)[CO—OC(CH$_3$)$_3$] |
| Ia.382 | —CH(CN)—CO—OCH$_3$ |
| Ia.383 | —CH(CN)—CO—OC$_2$H$_5$ |
| Ia.384 | —CH(CN)—CO—OC(CH$_3$)$_3$ |
| Ia.385 | —cyclopropyl |
| Ia.386 | —oxiranyl |
| Ia.387 | —tetrahydrofuran-2-yl |
| Ia.388 | —tetrahydrofuran-3-yl |
| Ia.389 | —tetrahydro—2H—pyran-2-yl |
| Ia.390 | —tetrahydro—2H—pyran-3-yl |
| Ia.391 | —tetrahydro—2H—pyran-4-yl |
| Ia.392 | —CH$_2$—CH$_2$—CO—OCH$_3$ |
| Ia.393 | —CH$_2$—CH$_2$—CO—OC$_2$H$_5$ |

Furthermore, particular preference is given to the substituted (4-bromopyrazol-3-yl)benzazoles of the formulae Ib to It and IA to IT, in particular to the compounds Ib.001 to Ib.393, which differ from the corresponding compounds Ia.001 to Ia.393 only in that $R^4$ is chlorine:

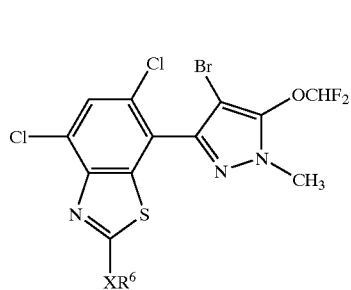

Ib the compounds Ic.001 to Ic.393, which differ from the corresponding compounds Ia.001 to Ia.393 only in that $R^4$ is fluorine:

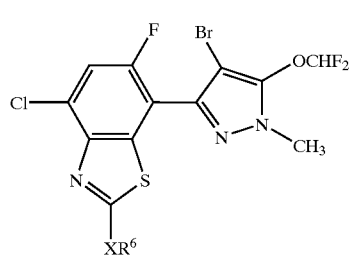

Ic the compounds Id.001 to Id.393, which differ from the corresponding compounds Ia.001 to Ia.393 only in that $R^2$ is trifluoromethyl:

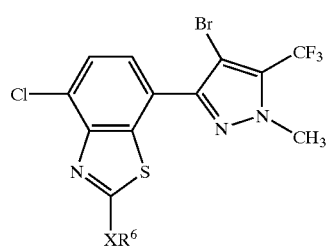

Id the compounds Ie.001 to Ie.393, which differ from the corresponding compounds Ia.001 to Ia.393 only in that $R^2$ is trifluoromethyl and $R^4$ is chlorine:

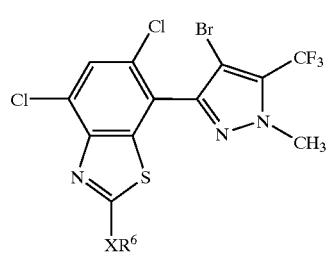

Ie the compounds If.001 to If.393, which differ from the corresponding compounds Ia.001 to Ia.393 only in that $R^2$ is trifluoromethyl and $R^4$ is fluorine:

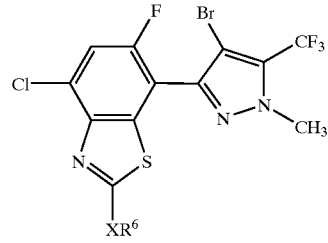

If the compounds Ig.001 to Ig.393, which differ from the corresponding compounds Ia.001 to Ia.393 only in that $R^2$ is methylsulfonyl:

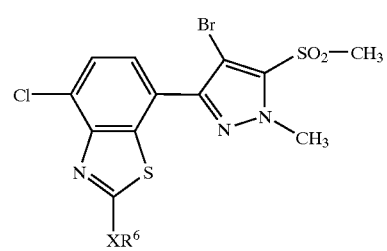

Ig the compounds Ih.001 to Ih.393, which differ from the corresponding compounds Ia.001 to Ia.393 only in that $R^2$ is methylsulfonyl and $R^4$ is chlorine:

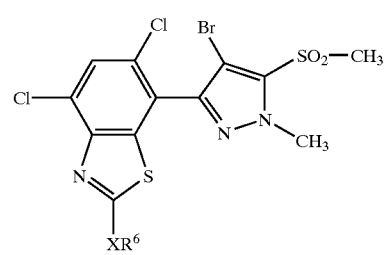

Ih the compounds Ij.001 to Ij.393, which differ from the corresponding compounds Ia.001 to Ia.393 only in that $R^2$ is methylsulfonyl and $R^4$ is fluorine:

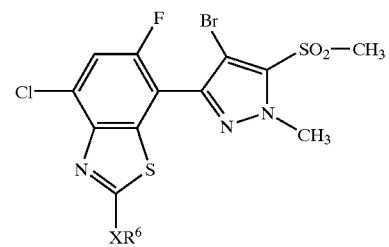

Ij the compounds Ik.001 to Ik.393, which differ from the corresponding compounds Ia.001 to Ia.393 in that Z is a group —N=C(XR⁶)—O— which is attached to α via the oxygen:

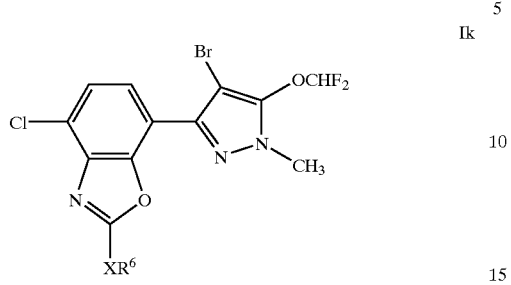

Ik the compounds Im.001 to Im.393, which differ from the corresponding compounds Ia.001 to Ia.393 in that R⁴ is chlorine and Z is a group —N=C(XR⁶)—O— which is attached to α via the oxygen:

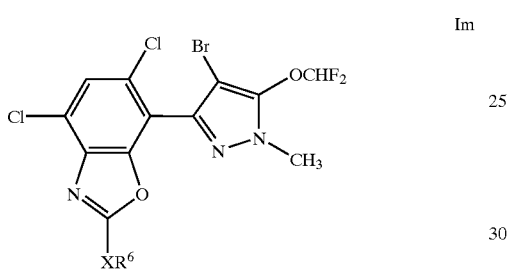

Im the compounds In.001 to In.393, which differ from the corresponding compounds Ia.001 to Ia.393 in that R⁴ is fluorine and Z is a group —N=C(XR⁶)—O— which is attached to α via the oxygen:

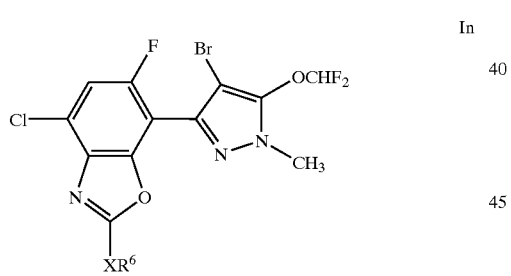

In the compounds Io.001 to Io.393, which differ from the corresponding compounds Ia.001 to Ia.393 in that R² is trifluoromethyl and Z is a group —N=C(XR⁶)—O— which is attached to α via the oxygen:

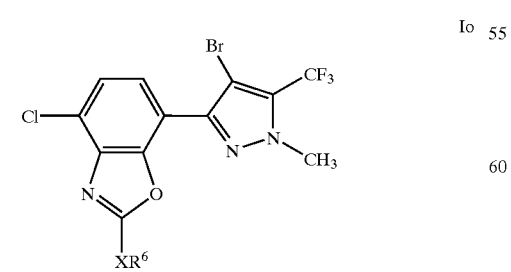

Io the compounds Ip.001 to Ip.393, which differ from the corresponding compounds Ia.001 to Ia.393 in that R² is trifluoromethyl and R⁴ is chlorine and Z is a group —N=C(XR⁶)—O— which is attached to α via the oxygen:

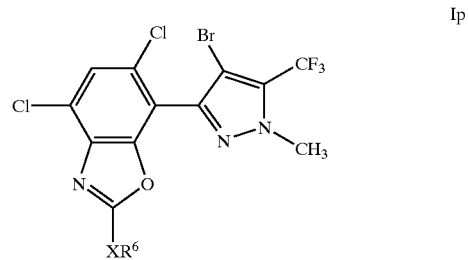

Ip the compounds Iq.001 to Iq.393, which differ from the corresponding compounds Ia.001 to Ia.393 in that R² is trifluoromethyl and R⁴ is fluorine and Z is a group —N=C(XR⁶)—O— which is attached to α via the oxygen:

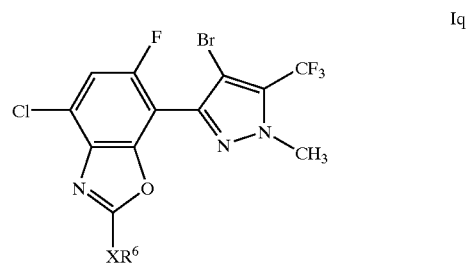

Iq the compounds Ir.001 to Ir.393, which differ from the corresponding compounds Ia.001 to Ia.393 in that R² is methylsulfonyl and Z is a group —N=C(XR⁶)—O— which is attached to α via the oxygen:

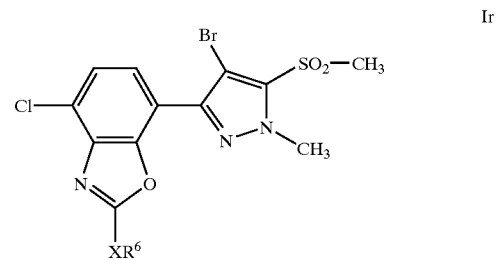

Ir the compounds Is.001 to Is.393, which differ from the corresponding compounds Ia.001 to Ia.393 in that R² is methylsulfonyl and R⁴ is chlorine and Z is a group —N=C(XR⁶)—O— which is attached to α via the oxygen:

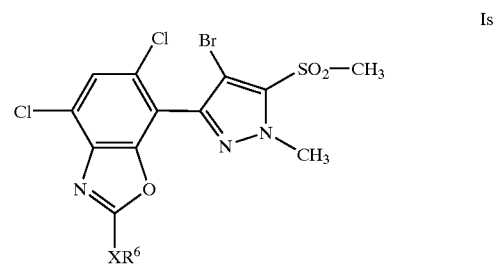

Is the compounds It.001 to It.393, which differ from the corresponding compounds Ia.001 to Ia.393 in that R² is methylsulfonyl and R$^4$ is fluorine and Z is a group —N=C(XR$^6$)—O— which is attached to α via the oxygen:

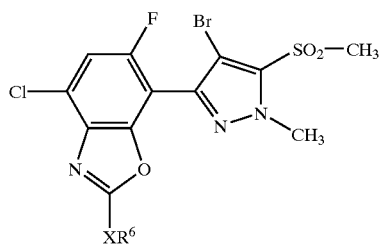

It the compounds IA.001 to IA.393, which differ from the corresponding compounds Ia.001 to Ia.393 only in that the group —N=C(XR$^6$)—S— is attached to α via the nitrogen:

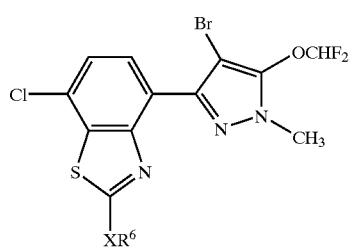

IA the compounds IB.001 to IB.393, which differ from the corresponding compounds Ia.001 to Ia.393 only in that R$^4$ is chlorine and the group —N=C(XR$^6$)—S— is attached to α via the nitrogen:

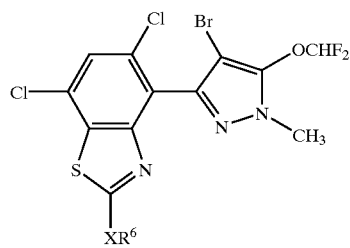

IB the compounds IC.001 to IC.393, which differ from the corresponding compounds Ia.001 to Ia.393 only in that R$^4$ is fluorine and the group —N=C(XR$^6$)—S— is attached to α via the nitrogen:

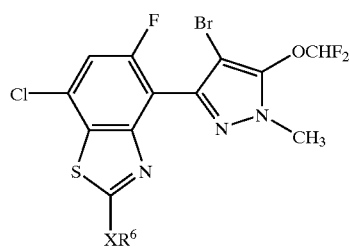

IC the compounds ID.001 to ID.393, which differ from the corresponding compounds Ia.001 to Ia.393 only in that R$^2$ is trifluoromethyl and the group —N=C(XR$^6$)—S— is attached to α via the nitrogen:

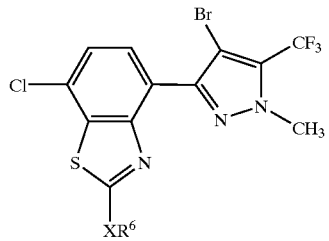

ID the compounds IE.001 to IE.393, which differ from the corresponding compounds Ia.001 to Ia.393 only in that R$^2$ is trifluoromethyl and R$^4$ is chlorine and the group —N=C(XR$^6$)—S— is attached to α via the nitrogen:

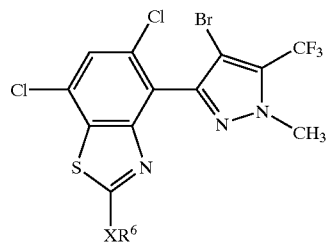

IE the compounds IF.001 to IF.393, which differ from the corresponding compounds Ia.001 to Ia.393 only in that R$^2$ is trifluoromethyl and R$^4$ is fluorine and the group —N=C(XR$^6$)—S— is attached to α via the nitrogen:

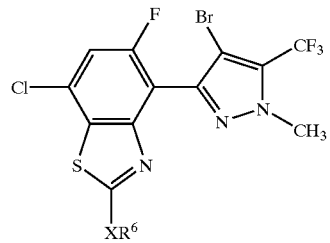

IF the compounds IG.001 to IG.393, which differ from the corresponding compounds Ia.001 to Ia.393 only in that R$^2$ is methylsulfonyl and the group —N=C(XR$^6$)—S— is attached to α via the nitrogen:

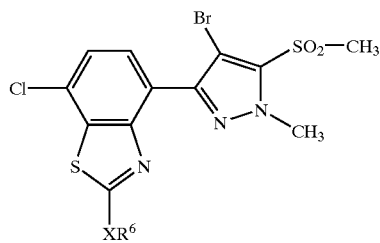

IG the compounds IH.001 to IH.393, which differ from the corresponding compounds Ia.001 to Ia.393 only in that $R^2$ is methylsulfonyl and $R^4$ is chlorine and the group —N=C(XR$^6$)—S— is attached to α via the nitrogen:

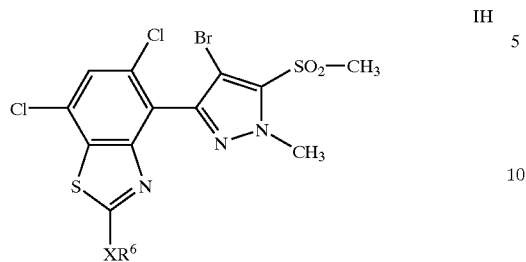

IH the compounds IJ.001 to IJ.393, which differ from the corresponding compounds Ia.001 to Ia.393 only in that $R^2$ is methylsulfonyl and $R^4$ is fluorine and the group —N=C(XR$^6$)—S— is attached to α via the nitrogen:

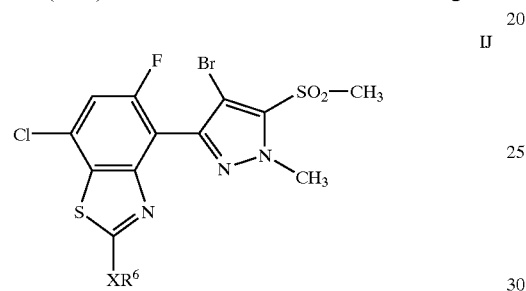

IJ the compounds IK.001 to IK.393, which differ from the corresponding compounds Ia.001 to Ia.393 only in that Z is a group —N=C(XR$^6$)—O— which is attached to α via the nitrogen:

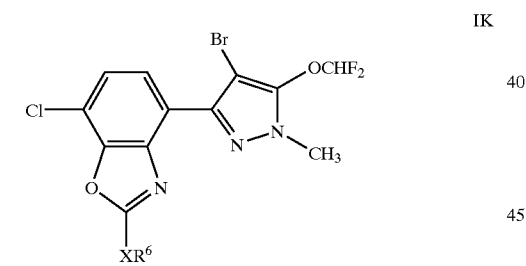

IK the compounds IM.001 to IM.393, which differ from the corresponding compounds Ia.001 to Ia.393 in that $R^4$ is chlorine and Z is a group —N=C(XR$^6$)—O— which is attached to α via the nitrogen:

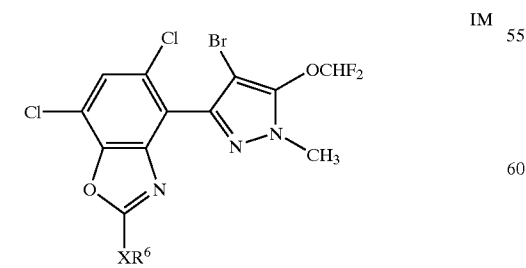

IM the compounds IN.001 to IN.393, which differ from the corresponding compounds Ia.001 to Ia.393 in that $R^4$ is fluorine and Z is a group —N=C(XR$^6$)—O— which is attached to α via the nitrogen:

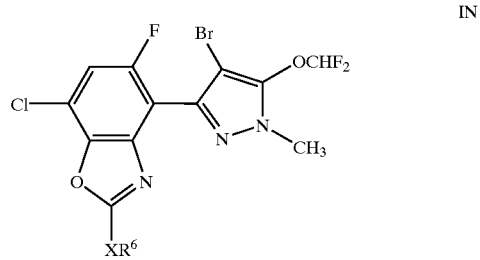

IN the compounds IO.001 to IO.393, which differ from the corresponding compounds Ia.001 to Ia.393 in that $R^2$ is trifluoromethyl and Z is a group —N=C(XR$^6$)—O— which is attached to α via the nitrogen:

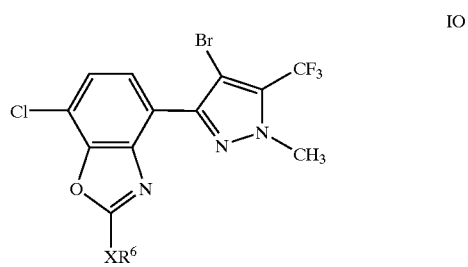

IO the compounds IP.001 to IP.393, which differ from the corresponding compounds Ia.001 to Ia.393 in that $R^2$ is trifluoromethyl and $R^4$ is chlorine and Z is a group —N=C(XR$^6$)—O— which is attached to α via the nitrogen:

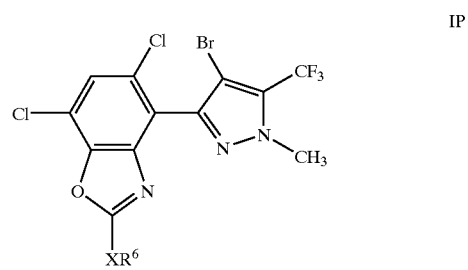

IP the compounds IQ.001 to IQ.393, which differ from the corresponding compounds Ia.001 to Ia.393 in that $R^2$ is trifluoromethyl and $R^4$ is fluorine and Z is a group —N=C(XR$^6$)—O— which is attached to α via the nitrogen:

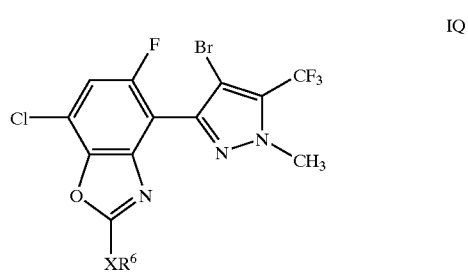

IQ the compounds IR.001 to IR.393, which differ from the corresponding compounds Ia.001 to Ia.393 in that $R^2$ is methylsulfonyl and Z is a group —N=C(XR⁶)—O— which is attached to α via the nitrogen:

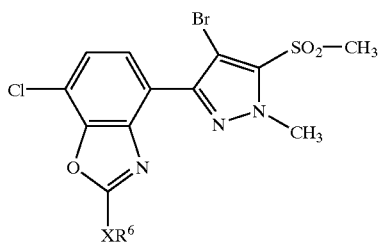

IR the compounds IS.001 to IS.393, which differ from the corresponding compounds Ia.001 to Ia.393 in that R² is methylsulfonyl and R⁴ is chlorine and Z is a group —N=C(XR⁶)—O— which is attached to α via the nitrogen:

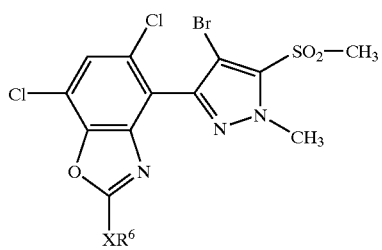

IS the compounds IT.001 to IT.393, which differ from the corresponding compounds Ia.001 to Ia.393 in that R² is methylsulfonyl and R⁴ is fluorine and Z is a group —N=C(XR⁶)—O— which is attached to α via the nitrogen:

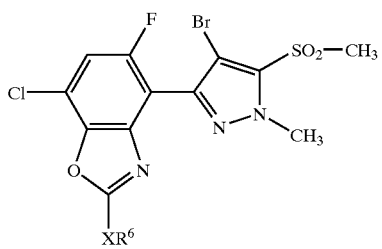

IT

The substituted (4-bromopyrazol-3-yl)benzazoles of the formula I can be obtained by various routes, in particular by one of the processes below:

A) Reaction of an aminophenylpyrazole of the formula IIIa or IIIb with a halogen and ammonium thiocyanate or with an alkali metal thiocyanate or alkaline earth metal thiocyanate:

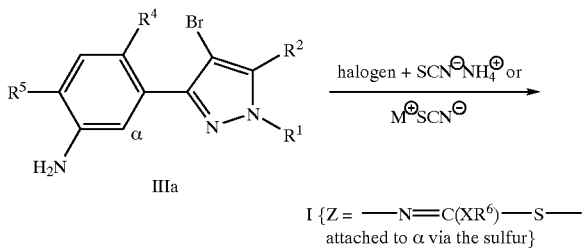

I {Z = —N=C(XR⁶)—S— attached to α via the sulfur}

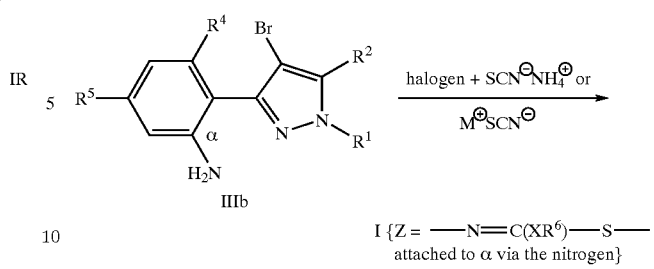

I {Z = —N=C(XR⁶)—S— attached to α via the nitrogen}

M⊕=alkali metal ion or 1/2 alkaline earth metal ion

The preferred halogen is chlorine or bromine; among the alkali metals/alkaline earth metal thiocyanates, preference is given to sodium thiocyanate.

In general, the reaction is carried out in an inert solvent/diluent, for example in a hydrocarbon, such as toluene and hexane, in a halogenated hydrocarbon, such as dichloromethane, in an ether, such as tetrahydrofuran, in an alcohol, such as ethanol, in a carboxylic acid, such as acetic acid, or in an aprotic solvent, such as dimethylformamide, acetonitrile and dimethyl sulfoxide.

The reaction temperature is usually between the melting point and the boiling point of the reaction mixture, preferably at from 0 to 150° C.

To achieve as high a yield of the product of value as possible, halogen and ammonium thiocyanate or alkali metal/alkaline earth metal thiocyanate are employed in approximately equimolar amounts or in excess, up to about 5 times the molar amount, based on the amount of IIIa or IIIb.

A variant of the process entails reacting the aminophenylpyrazole IIIa or IIIb initially with ammonium thiocyanate or an alkali metal thiocyanate or alkaline earth metal thiocyanate to give a thiourea IVa or IVb

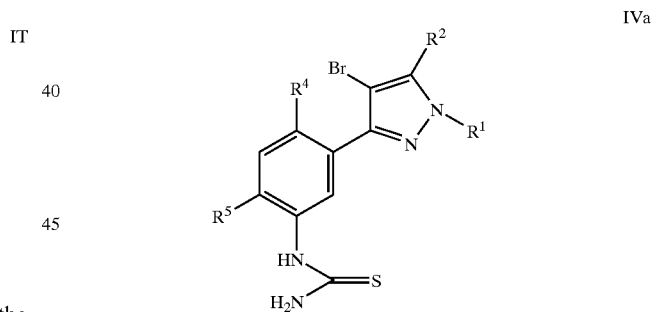

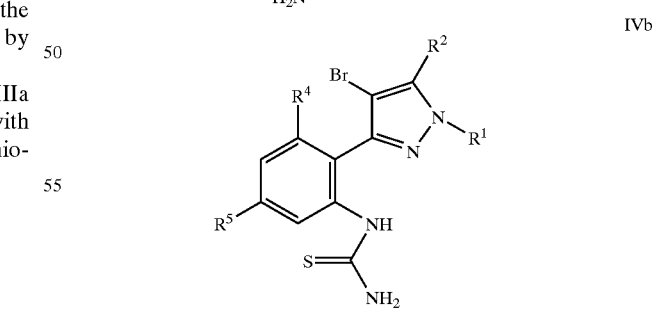

and converting IVa or IVb subsequently into I where Z=—N=C(XR⁶)—S— by treatment with halogen.

B) Diazotization of an aminophenylpyrazole of the formula IIIa or IIIb, conversion of the respective diazonium salt into an azidophenylpyrazole of the formula Va or Vb and its reaction either B.1) with a carboxylic acid or B.2) initially with a sulfonic acid (to give VIa or VIb), hydrolysis of the sulfonate formed to give aminophenol VIIa or VIIb, and its conversion into I:

B.1)

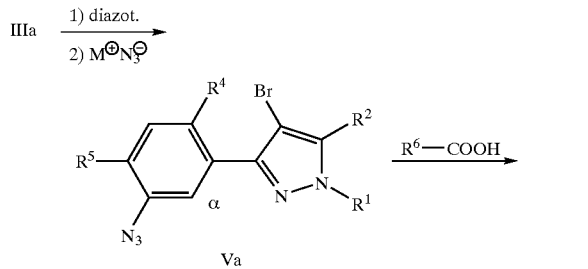

M⊕=alkali metal ion or 1/2 alkaline earth metal ion.

B.2)

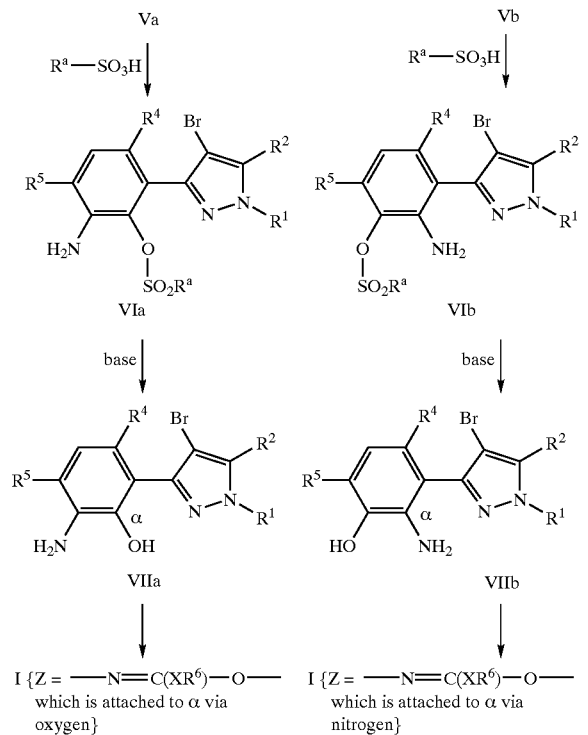

For carrying out the diazotization, the details given for process C) apply. The conversion into the aryl azides Va/Vb is preferably carried out by reacting IIIa/IIIb with an alkali metal azide or alkaline earth metal azide such as sodium azide, or by reaction with trimethylsilyl azide.

The reaction with a carboxylic acid mentioned under B.1) is either carried out in an inert solvent, for example in an ether, such as tetrahydrofuran and dioxane, an aprotic solvent, such as dimethylformamide and acetonitrile, a hydrocarbon, such as toluene and hexane, a halogenated hydrocarbon, such as dichloromethane, or in the absence of a solvent in an excess of carboxylic acid $R^6$—COOH. In the latter case, the addition of a mineral acid, such as phosphoric acid, may be advantageous. The reaction is preferably carried out at elevated temperature, for example at the boiling point of the reaction mixture. For the reaction of Va/Vb with a sulfonic acid $R^a$—$SO_3H$ (where $R^a$ is $C_1$–$C_4$-alkyl or $C_1$–$C_4$-haloalkyl, preferably methyl or trifluoromethyl) mentioned first under B.2), the details given above for the reaction of Va/Vb with $R^6$—COOH apply. The subsequent hydrolysis of the sulfonates VIa/VIb is preferably carried out by reaction with an aqueous base, such as sodium hydroxide solution and potassium hydroxide solution, it being possible to add, if desired, a solvent, for example an ether, such as dioxane and tetrahydrofuran, or an alcohol, such as methanol and ethanol. The concluding reaction to give I is known per se and can be carried out in an extremely multifarious manner. In this context, reference is made to the details given in Houben-Weyl, Methoden der Organischen Chemie, Georg Thieme Verlag Stuttgart, Vol. E8a 1993, p. 1032 ff.

The azidophenylpyrazoles of the formulae Va and Vb are new. Particularly preferred compounds of the formula Va are the compounds Va.1–Va.9 mentioned in Table 2 below:

| No. | $R^1$ | $R^2$ | $R^4$ | $R^5$ |
|---|---|---|---|---|
| Va. 1 | $CH_3$ | $OCHF_2$ | H | Cl |
| Va. 2 | $CH_3$ | $OCHF_2$ | Cl | Cl |
| Va. 3 | $CH_3$ | $OCHF_2$ | F | Cl |
| Va. 4 | $CH_3$ | $CF_3$ | H | Cl |
| Va. 5 | $CH_3$ | $CF_3$ | Cl | Cl |
| Va. 6 | $CH_3$ | $CF_3$ | F | Cl |
| Va. 7 | $CH_3$ | $SO_2$—$CH_3$ | H | Cl |
| Va. 8 | $CH_3$ | $SO_2$—$CH_3$ | Cl | Cl |
| Va. 9 | $CH_3$ | $SO_2$—$CH_3$ | F | Cl |

C) Diazotization of substituted (4-bromopyrazol-3-yl) benzazoles of the formula I in which $XR^6$ is amino, and subsequent conversion of the diazonium salt into compounds I where —$XR^6$=cyano or halogen {for the Sandmeyer reaction, cf., for example, Houben-Weyl, Methoden der Organischen Chemie, Georg Thieme Verlag Stuttgart, Vol. 5/4, 4th edition 1960, p. 438ff.}, —X—=sulfur {cf., for example, Houben-Weyl, Methoden der Organischen Chemie, Georg Thieme Verlag Stuttgart, Vol.E11 1984, p. 43 and 176}, —$XR^6$=for example —$CH_2$—CH(halogen)-$R^8$, —CH=CH—$R^8$, —CH=C(halogen)-$R^8$ {in general, these are products of a Meerwein arylation; cf., for example, C. S. Rondestredt, Org. React. 11, (1960), 189 and H. P. Doyle et al., J. Org. Chem. 42, (1977) 2431}:

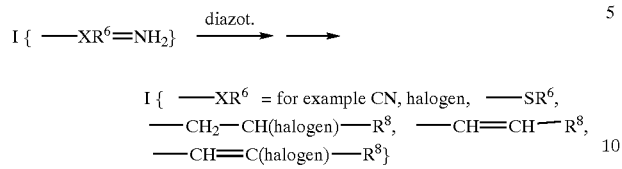

In general, the diazonium salt is obtained in a manner known per se by reacting I where —$XR^6$=amino in an aqueous solution of an acid, for example in hydrochloric acid, hydrobromic acid or sulfuric acid, with a nitrite, such as sodium nitrite and potassium nitrite.

However, it is also possible to carry out the reaction in the absence of water, for example in hydrogen chloride-containing glacial acetic acid, in absolute alcohol, in dioxane or tetrahydrofuran, in acetonitrile or in acetone and to treat the starting material (I where —$XR^6$=$NH_2$) with a nitrous acid ester, such as tert-butyl nitrite and isopentyl nitrite.

The conversion of the diazonium salt obtained in this manner into the corresponding compound I where —$XR^6$=cyano, chlorine, bromine or iodine is particularly preferably carried out by treatment with a solution or suspension of a copper(I) salt, such as copper(I) cyanide, copper(I) chloride, copper(I) bromide and copper(I) iodide, or with a solution of an alkali metal salt.

Compounds I where —X—=sulfur are usually obtained by reacting the diazonium salt with a dialkyl disulfide, such as dimethyl disulfide and diethyl disulfide, or by using, for example, diallyl disulfide or dibenzyl disulfide.

The Meerwein arylation usually comprises the reaction of the diazonium salts with alkenes (here: $H_2C$=CH—$R^8$) or alkynes (here: HC≡—C—$R^8$). Here, preference is given to employing an excess of the alkene or alkyne of up to about 3000 mol %, based on the amount of the diazonium salt.

The above-described reactions of the diazonium salt can be carried out, for example, in water, in aqueous hydrochloric acid or hydrobromic acid, in a ketone, such as acetone, diethyl ketone and methyl ethyl ketone, in a nitrile, such as acetonitrile, in an ether, such as dioxane and tetrahydrofuran, or in an alcohol, such as methanol and ethanol.

Unless stated otherwise for the individual reactions, the reaction temperatures are usually at from (−30) to +50° C.

Preference is given to using all the reaction participants in approximately stoichiometric amounts; however, an excess of one the other component of up to about 3000 mol % may be advantageous.

D) Oxidation of a substituted (4-bromopyrazol-3-yl) benzazole I, in which X is sulfur to give I where X=—SO— in a manner known per se (cf., for example, Houben-Weyl, Methoden der Organischen Chemie, Georg Thieme Verlag Stuttgart, Vol. E 11/1, 1985, p. 702 ff., Vol. IX, 4th edition, 1955, p. 211):

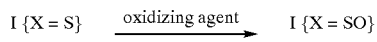

Suitable oxidizing agents are, for example, hydrogen peroxide, organic peroxides, such as peracetic acid, trifluoroperacetic acid, m-chloroperbenzoic acid, tert-butyl hydroperoxide and tert-butyl hypochlorite, and also inorganic compounds, such as sodium metaiodate, chromic acid and nitric acid.

Depending on the oxidizing agent, the reaction is usually carried out in an organic acid, such as acetic acid and trichloroacetic acid, in a chlorinated hydrocarbon, such as methylene chloride, chloroform and 1,2-dichloroethane, in an aromatic hydrocarbon, such as benzene, chlorobenzene and toluene, or in a protic solvent, such as methanol and ethanol. Mixtures of the abovementioned solvents are also suitable.

The reaction temperature is generally at from (−30)° C. to the boiling point of the reaction mixture in question, and preference is usually given to the lower temperature range. Advantageously, starting material and oxidizing agent are employed in an approximately stoichiometric ratio; however, it is also possible to employ an excess of one or the other component.

E) Oxidation of a substituted (4-bromopyrazol-3-yl) benzazole I, where X is sulfur or —SO—, to give I where X=—$SO_2$— in a manner known per se (cf., for example, Houben-Weyl, Methoden der Organischen Chemie, Georg Thieme Verlag Stuttgart, Vol. E 11/2, 1985, p. 1132 ff. and Vol. IX, 4th edition, 1955, p. 222 ff.):

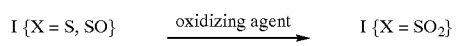

Suitable oxidizing agents are, for example, hydrogen peroxide, organic peroxides, such as peracetic acid, trifluoroperacetic acid and m-chloroperbenzoic acid, furthermore inorganic oxidizing agents, such as potassium permanganate. The presence of a catalyst, for example tungstate, can have advantageous effects on the course of the reaction.

In general, the reaction is carried out in an inert solvent; suitable solvents being, depending on the oxidizing agent, for example organic acids, such as acetic acid and propionic acid, chlorinated hydrocarbons, such as methylene chloride, chloroform and 1,2-dichloroethane, aromatic hydrocarbons or halogenated hydrocarbons, such as benzene, chlorobenzene and toluene, or water. It is also possible to use mixtures of the abovementioned solvents.

Usually, the reaction is carried out at from (−30)° C. to the boiling point of the reaction mixture in question, preferably at from 10° C. to the boiling point.

Advantageously, the starting material I where X=sulfur or SO and the oxidizing agent are employed in approximately stoichiometric amounts. However, to optimize the conversion of the starting material, it may be advisable to employ an excess of oxidizing agent.

F) Reaction of a substituted (4-bromopyrazol-3-yl) benzazole I where the grouping —$XR^6$ is chlorine, bromine, alkylsulfonyl or haloalkylsulfonyl in the pres ence of a base with an alcohol, mercaptan, amine or a CH-acidic compound (VIII):

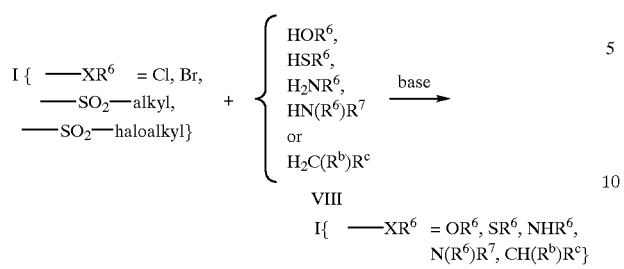

$R^b$ and $R^c$ independently of one another are each cyano or ($C_1$–$C_4$-alkoxy)carbonyl.

Advantageously, the reaction is carried out in an inert solvent, for example in an ether, such as diethyl ether, methyl tert-butyl ether, dimethoxy ethane, diethylene glycol dimethyl ether, tetrahydrofuran and dioxane, a ketone, such as acetone, diethyl ketone, ethyl methyl ketone and cyclohexanone, a dioplar aprotic solvent, such as acetonitrile, dimethylformamide, N-methylpyrrolidone and dimethyl sulfoxide, a protic solvent such as methanol and ethanol, an aromatic, if desired halogenated, hydrocarbon, such as benzene, chlorobenzene and 1,2-dichlorobenzene, a heteroaromatic solvent, such as pyridine and quinoline, or in a mixture of such solvents. Tetrahydrofuran, acetone, diethyl ketone and dimethylformamide are preferred.

Suitable bases are, for example, the hydroxides, hydrides, alkoxides, carbonates or bicarbonates of alkali metal and alkaline earth metal cations, tertiary aliphatic amines, such as triethylamine, N-methylmorpholine and N-ethyl-N,N-diisopropylamine, bi- and tricyclic amines, such as diazabicycloundecane (DBU) and diazabicyclooctane (DABCO), or aromatic nitrogen bases, such as pyridine, 4-dimethylaminopyridine and quinoline. Combinations of different bases are also suitable. Preferred bases are sodium hydride, sodium hydroxide, sodium carbonate, potassium carbonate, sodium methoxide, sodium ethoxide and potassium tert-butoxide.

The amines $H_2NR^6$ or $HN(R^6)R^7$ may serve as reaction participants and simultaneously as bases, in which case the amine should be present in at least a two-fold excess, based on the amount of the starting material I. It is, of course, also possible to employ a greater excess of amine, up to approximately 10 times the molar amount, based on the amount of I where —$XR^6$=Cl, Br, —$SO_2$-alkyl or —$SO_2$-haloalkyl.

The starting materials are generally employed in approximately stoichiometric amounts; however, an excess of one or the other components may be advantageous with a view to the practice of the process or to obtain as complete a conversion of the starting material I {—$XR^6$≈Cl, Br, —$SO_2$-alkyl, —$SO_2$-haloalkyl} as possible.

The molar ratio of alcohol, mercaptan, amine or CH-acidic compound (VIII) to base is generally from 1:1 to 1:3.

The concentration of the starting materials in the solvent is usually at from 0.1 to 5.0 mol/l.

The reaction can be carried out at temperatures of from 0° C. to the reflux temperature of the reaction mixture in question.

G) Reaction of a substituted (4-bromopyrazol-3-yl) benzazole I in which —$XR^6$ is halogen with a ($C_1$–$C_6$-alkyl)-Grignard reagent:

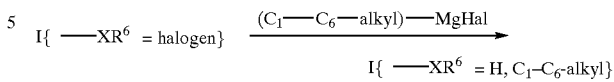

Here, Hal is chloride or bromide.

In general, the reaction is carried out in an inert solvent/diluent, for example a hydrocarbon, such as hexane or toluene, or an ether, such as diethyl ether, tetrahydrofuran and dioxane.

If desired, it is possible to add a transition metal catalyst in amounts of from 0.0001 to 10 mol %. Suitable transition metal catalysts are, for example, nickel and palladium catalysts, such as nickel dichloride, bis(triphenylphosphine)nickel dichloride, [bis(1,2-diphenylphosphino)ethane]nickel dichloride, [bis(1,3-diphenylphosphino)propane]nickel dichloride, palladium dichloride, tetrakis(triphenylphosphine)-palladium, bis(triphenylphosphine)palladium dichloroide, [bis(1,2-diphenylphosphino)ethane] palladium dichloride, [bis(1,3-diphenylphosphino) propane]palladium dichloride and [bis(diphenylphosphino)ferrocene]palladium dichloride, but also mixtures of palladium dichloride or nickel dichloride and phosphines, such as triphenylphosphine, bis-1,2-(diphenylphosphino)ethane and bis-1,3-(diphenylphosphino)propane. Depending on the practice of the reaction, this gives rise to compounds I where —$XR^6$=hydrogen or $C_1$–$C_6$-alkyl or to corresponding compounds of alkylated and non-alkylated compound I which can, however, be separated in a customary manner.

In general, the reaction is carried out at from (−100)° C. to the boiling point of the reaction mixture.

The amount of Grignard reagent is not critical; usually, ($C_1$–$C_6$-alkyl)-MgHal is employed in an approximately equimolar amount or in excess, up to about 10 times the molar amount, based on the amount of I where —$XR^6$=halogen.

Unless stated otherwise, all the processes described above are advantageously carried out under atmospheric pressure or under the autogenous pressure of the reaction mixture in question.

The work-up of the reaction mixtures is usually carried out in a conventional manner. Unless stated otherwise in the processes described above, the products of value are obtained, for example, after the dilution of the reaction solution with water by filtration, crystallization or solvent extraction, or by removing the solvent, partitioning the residue in a mixture of water and a suitable organic solvent and work-up of the organic phase to afford the product.

The substituted (4-bromopyrazol-3-yl)benzazoles I can be obtained as isomer mixtures in the preparation; however, if desired, these can be separated into largely pure isomers using customary methods such as crystallization or chromatography, including chromatography over an optically active adsorbate. Pure optically active isomers can be prepared advantageously from suitable optically active starting materials.

Agriculturally useful salts of the compounds I can be formed by reaction with a base of the corresponding cation, preferably an alkali metal hydroxide or hydride, or by reaction with an acid of the corresponding anion, preferably of hydrochloric acid, hydrobromic acid, sulfuric acid, phosphoric acid or nitric acid.

Salts of I where the metal ion is not an alkali metal ion can be prepared by cation exchange of the corresponding alkali metal salt in a conventional manner, similarly ammonium, phosphonium, sulfonium and sulfoxonium salts by means of ammonia, phosphonium, sulfonium or sulfoxonium hydroxides.

The compounds I and their agriculturally useful salts are suitable, both in the form of isomer mixtures and in the form of the pure isomers, as herbicides. The herbicidal compositions comprising I control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

Taking into account the universality of the application methods, the compounds I, or herbicidal compositions comprising them, can additionally be employed in a further number of crop plants for eliminating undesirable plants. Examples of suitable crops are the following:

Allium cepa, Ananas comosus, Arachis hypogaea, Asparagus officinalis, Beta vulgaris spec. altissima, Beta vulgaris spec. rapa, Brassica napus var. napus, Brassica napus var. napobrassica, Brassica rapa var. silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spec., Manihot esculenta, Medicago sativa, Musa spec., Nicotiana tabacum (N.rustica), Olea europaea, Oryza sativa, Phaseolus lunatus, Phaseolus vulgaris, Picea abies, Pinus spec., Pisum sativum, Prunus avium, Prunus persica, Pyrus communis, Ribes sylvestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera and Zea mays.

In addition, the compounds I may also be used in crops which tolerate the action of herbicides owing to breeding, including genetic engineering methods.

Moreover, the substituted (4-bromopyrazol-3-yl) benzazoles I are also suitable for the desiccation and/or defoliation of plants.

As desiccants, they are suitable, in particular, for desiccating the aerial parts of crop plants such as potatoes, oilseed rape, sunflowers and soybeans. This allows completely mechanical harvesting of these important crop plants.

It is also of economic interest to facilitate harvesting, which is made possible by concentrating, over a period of time, dehiscence, or reducing the adherence to the tree, in citrus fruit, olives or other species and varieties of pomaceous fruit, stone fruit and nuts. The same mechanism, i.e. promotion of the formation of abscission tissue between fruit or leaf and shoot of the plants, is also important for readily controllable defoliation of useful plants, in particular cotton.

Moreover, shortening the period within which the individual cotton plants mature results in improved fiber quality after harvesting.

The compounds I, or the compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for spreading, or granules, by means of spraying, atomizing, dusting, spreading or pouring. The use forms depend on the intended aims; in any case, they should guarantee the finest possible distribution of the active compounds according to the invention.

Suitable inert auxiliaries are essentially: mineral oil fractions of medium to high boiling point, such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the substances, either as such or dissolved in an oil or solvent, can be homogenized in water by means of a wetting agent, tackifier, dispersant or emulsifier. Alternatively, it is possible to prepare concentrates comprising active compound, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene, or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or grinding the active compounds together with a solid carrier.

Granules, e.g. coated granules, impregnated granules and homogeneous granules, can be prepared by binding the active compounds to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin, such as cereal meal, tree bark meal, wood meal and nutshell meal, cellulose powders, or other solid carriers.

The concentrations of the active compounds I in the ready-to-use preparations can be varied within wide ranges. In general, the formulations comprise approximately from 0.001 to 98% by weight, preferably 0.01 to 95% by weight of at least one active compound. The active compounds I are employed in a purity of from 90% to 100%, preferably 95% to 100% (according to NMR spectrum).

The formulation examples which follow illustrate the preparation of such products:

I. 20 parts by weight of the compound No. In.003 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

II. 20 parts by weight of the compound No. Im.003 are dissolved in a mixture composed of 40 parts by weight of cyclohexanone, 30 parts by weight of isobutanol, 20 parts by weight of the adduct of 7 mol of ethylene oxide to I mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

III. 20 parts by weight of the active compound No. Ik.003 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to I mol of castor oil. Pouring the solution into 100,000 parts by weight of water and finely distributing it therein gives an aqueous dispersion which comprises 0.02% by weight of the active compound.

IV. 20 parts by weight of the active compound No. It.003 are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound.

V. 3 parts by weight of the active compound No. In.003 are mixed with 97 parts by weight of finely divided kaolin. This gives a dust which comprises 3% by weight of active compound.

VI. 20 parts by weight of the active compound No. Im.003 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound No. Ik.003 is dissolved in a mixture composed of 70 parts by weight of cyclohexanone, 20 parts by weight of ethoxylated isooctylphenol and 10 parts by weight of ethoxylated castor oil. The mixture can then be diluted with water to the desired concentration of active compound. This gives a stable emulsion concentrate.

VIII. 1 part by weight of the compound No. It.003 is dissolved in a mixture composed of 80 parts by weight of cyclohexanone and 20 parts by weight of Wettol® EM 31 (=nonionic emulsifier based on ethoxylated castor oil from BASF). The mixture can then be diluted with water to the desired concentration of active compound. This gives a stable emulsion concentrate.

The active compounds I or the herbicidal compositions can be applied pre- or post-emergence. If the active compounds are less well tolerated by certain crop plants, application techniques may be used in which the herbicidal compositions are sprayed, with the aid of the spraying equipment, in such a way that they come into as little contact as possible, if any, with the leaves of the sensitive crop plants, while the active compounds reach the leaves of undesirable plants growing underneath, or the bare soil surface (post-directed, lay-by).

The rates of application of active compound I are from 0.001 to 3.0, preferably 0.01 to 1.0, kg/ha of active substance (a.s.), depending on the control target, the season, the target plants and the growth stage.

To widen the spectrum of action and to achieve synergistic effects, the substituted (4-bromopyrazol-3-yl)benzazoles I may be mixed with a large number of representatives of other herbicidal or growth-regulating active compounds and then applied concomitantly. Suitable components for mixtures are, for example, 1,2,4-thiadiazoles, 1,3,4-thiadiazoles, amides, aminophosphoric acid and its derivatives, aminotriazoles, anilides, aryl/hetaryl-oxyalkanoic acids and their derivatives, benzoic acid and its derivatives, benzothiadiazinones, 2-(hetaroyl/aroyl)-1,3-cyclohexanediones, hetaryl aryl ketones, benzyl-isoxazolidinones, meta-CF$_3$-phenyl derivatives, carbamates, quinolinecarboxylic acid and its derivates, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds I, alone or in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

PREPARATION EXAMPLES

Example 1

7-(4-Bromo-5-difluoromethoxy-1-methyl-1H-pyrazol-3-yl)-4-chloro-2-ethyl-6-fluorobenzoxazole (Compound No. In.003)

A solution of 12.9 g (33 mmol) of 5-(4-bromo-5-difluoromethoxy-1-methyl-1H-pyrazol-3-yl)-2-chloro-4-fluorophenyl azide in 300 ml of propionic acid was refluxed for 4 h. The mixture was subsequently concentrated. The residue was dissolved in ethyl acetate and the organic phase was then washed with dilute aqueous sodium bicarbonate solution, then dried over magnesium sulfate and finally concentrated. The crude product was purified by silica gel chromatography (mobile phase: hexane/ethyl acetate=9:1). Yield: 3.3 g. MS [m/z]: 423 [M$^+$]. $^1$H-NMR (400 MHz, in CDCl$_3$): δ[ppm]=1.45 (t, 3H), 2.98 (q, 2H), 3.92 (s, 3H), 6.74 (t, 1H), 7.24 (d, 1H).

Intermediate 1.1
4-Bromo-3-(4-chloro-2-fluoro-5-nitrophenyl)-5-difluoromethoxy-1-methyl-1H-pyrazole At (−30)° C., 15.5 g (0.16 mol) of conc. sulfuric acid were added to 16.6 g (0.26 mol) of conc. nitric acid. After cooling to (−40)° C., the mixture was admixed dropwise with a solution of 18.7 g (53 mmol) of 4-bromo-3-(4-chloro-2-fluorophenyl)-5-difluoro-methoxy-1-methyl-1H-pyrazole in 100 ml of dichloromethane. The reaction mixture was subsequently stirred for 4 h and then poured into ice-water. The organic phase was separated off, washed with dilute aqueous sodium bicarbonate solution and water, dried over magnesium sulfate and finally concentrated. Yield: 15.6 g. $^1$H-NMR (270 MHz, in CDCl$_3$): δ[ppm]=3.88 (s, 3H), 6.72 (t, 1H), 7.41 (d, 1H), 8.24 (d, 1H).

Intermediate 1.2
5-(4-Bromo-5-difluoromethoxy-1-methyl-1H-pyrazol-3-yl)-2-chloro-4-fluoroaniline 5 g of Raney nickel were added to a solution of 15.6 g (39 mmol) of 4-bromo-3-(4-chloro-2-fluoro-5-nitrophenyl)-5-difluoromethoxy-1-methyl-1H-pyrazole in 150 ml of tetrahydrofuran, and the mixture was then hydrogenated under a slightly superatmospheric hydrogen pressure until the calculated amount of hydrogen had been taken up. The catalyst was subsequently filtered off through a bed of kieselguhr. The filtrate was concentrated. Yield: quantitative. $^1$H-NMR (400 MHz, in CDCl$_3$): δ[ppm]=3.85 (s, 3H), 3.97 (s, 2H), 6.70 (t, 1H), 6.89 (d, 1H), 7.12 (d, 1H).

Precursor 1.3
5-(4-Bromo-5-difluoromethoxy-1-methyl-1H-pyrazol-3-yl)-2-chloro-4-fluorophenyl azide (No. Va.3)

At 10–15° C., initially 6.0 g (59 mmol) of t-butyl nitrite and then, a little at a time, 3.8 g (59 mmol) of sodium azide were added to a solution of 14.4 g (39 mmol) of 5-(4-bromo-5-difluoromethoxy-1-methyl-1H-pyrazol-3-yl)-2-chloro-4-fluoroaniline in 60 ml of trifluoroacetic acid. The mixture was subsequently stirred at approximately 20° C. for one hour, and the reaction solution was then poured onto ice. The product was extracted from the aqueous phase using methyl t-butyl ether.

The organic phase was then washed with 10% strength aqueous sodium hydroxide solution, dried over magnesium sulfate and finally concentrated taking care not to heat the concentrated solutions or the pure substance over 40° C. Yield: 12.9 g. MS [m/z]: 395 [M$^+$]. $^1$H-NMR (270 MHz, in CDCl$_3$): δ[ppm]=3.88 (s, 3H), 6.71 (t, 1H), 7.25 (d, 1H), 7.33 (d, 1H).

Example 2
7-(4-Bromo-5-difluoromethoxy-1-methyl-1H-pyrazol-3-yl)-4,6-dichloro-2-ethylbenzoxazole (Compound No. Im.003)

This compound was prepared by the method of Example 1. $^1$H-NMR (270 MHz, in CDCl$_3$): δ[ppm]=1.43 (t, 3H), 2.97 (q, 2H), 3.92 (s, 3H), 6.75 (t, 1H), 7.49 (s, 1H).

Intermediate 2.1
4-Bromo-3-(2,4-dichloro-5-nitrophenyl)-5-difluoromethoxy-1-methyl-1H-pyrazole This compound was prepared similarly to Intermediate 1.1. $^1$H-NMR (270 MHz, in CDCl$_3$): δ[ppm]=3.88 (s, 3H), 6.72 (t, 1H), 7.71 (s, 1H), 8.04 (s, 1H).

Intermediate 2.2
5-(4-Bromo-5-difluoromethoxy-1-methyl-1H-pyrazol-3-yl)-2,4-dichloroaniline This compound was prepared similarly to Intermediate 1.2. $^1$H-NMR (270 MHz, in CDCl$_3$): δ[ppm]=3.84 (s, 3H), 4.12 (s, 2H), 6.72 (t, 1H), 6.79 (s, 1H), 7.38 (s, 1H).

Intermediate 2.3
5-(4-Bromo-5-difluoromethoxy-1-methyl-1H-pyrazol-3-yl)-2,4-dichlorophenyl azide (No. Va.2)

This compound was prepared similarly to Intermediate 1.3. MS [m/z]: 411 [M$^+$]. $^1$H-NMR (270 MHz, in CDCl$_3$): δ[ppm]=3.87 (s, 3H), 6.72 (t, 1H), 7.21 (s, 1H), 7.52 (s, 1H).

Example 3
7-(4-Bromo-5-difluoromethoxy-1-methyl-1H-pyrazol-3-yl)-4-chloro-2-ethylbenzoxazole (Compound No. Ik.003)

This compound was prepared by the method of Example 1. $^1$H-NMR (270 MHz, in CDCl$_3$): δ[ppm]=1.48 (t, 3H), 3.03 (q, 2H), 3.92 (s, 3H), 6.74 (t, 1H), 7.40 (d, 1H), 7.55 (d, 1H).

Intermediate 3.1
4-Bromo-3-(4-chlorophenyl)-5-difluoromethoxy-1-methyl-1H-pyrazole 7.9 g (43 mmol) of bromine were added to a solution of 10.1 g (39 mmol) of 3-(4-chlorophenyl)-5-difluoromethoxy-1-methyl-1H-pyrazole in 100 ml of carbon tetrachloride, and the mixture was then stirred for 16 h. The solution was then washed with sat. aqueous sodium bicarbonate solution, dried over magnesium sulfate and finally concentrated. Yield: 12.9 g. $^1$H-NMR (270 MHz, in CDCl$_3$): δ[ppm]=3.84 (s, 3H), 6.69 (t, 1H), 7.40 (d, 2H), 7.81 (d, 2H).

Intermediate 3.2
4-Bromo-3-(4-chloro-3-nitrophenyl)-5-difluoromethoxy-1-methyl-1H-pyrazole This compound was prepared similarly to Intermediate 1.1. $^1$H-NMR (270 MHz, in CDCl$_3$): δ[ppm]=3.86 (s, 3H), 6.70 (t, 1H), 7.40 (d, 1H), 8.08 (dd, 1H), 8.46 (d, 1H).

Intermediate 3.3
5-(4-Bromo-5-difluoromethoxy-1-methyl-1H-pyrazol-3-yl)-2-chloroaniline A little at a time, 11.7 g (35 mmol) of 4-bromo-3-(chloro-3-nitrophenyl)-5-difluoromethoxy-1-methyl-1H-pyrazole were added to a suspension of 10.2 g (0.18 mol) of iron powder in 30 ml of acetic acid and 50 ml of ethanol which had been heated to 70–75° C. The mixture was subsequently refluxed for 2 h. After cooling, ethyl acetate was added, and the solution was then filtered through a bed of kieselguhr. The filtrate was washed with saturated aqueous bicarbonate solution and water, then dried over magnesium sulfate and finally concentrated. Yield: quantitative. $^1$H-NMR (400 MHz, in CDCl$_3$): δ[ppm]=3.81 (s, 3H), 4.12 (s, 2H), 6.68 (t, 1H), 7.19 (dd, 1H), 7.26 (d, 1H), 7.29 (d, 1H).

Intermediate 3.4
5-(4-Bromo-5-difluoromethoxy-1-methyl-1H-pyrazol-3-yl)-2-chlorophenyl azide (No. Va.1)

This compound was prepared similarly to Intermediate 1.3.

Example 4
7-(4-Bromo-1-methyl-5-methylsulfonyl-1H-pyrazol-3-yl)-4-chloro-2-ethyl-6-fluorobenzoxazole (No. It.003)

This compound was prepared by the method of Example 1. $^1$H-NMR (400 MHz, in CDCl$_3$): δ[ppm]=1.45 (t, 3H), 2.98 (q, 2H), 3.36 (s, 3H), 4.32 (s, 3H), 7.27 (d, 1H).

Intermediate 4.1
4-Bromo-3-(4-chloro-2-fluorophenyl)-1-methyl-5-methylthio-1H-pyrazole 13.7 g (86 mmol) of bromine were added dropwise to a solution of 20 g (78 mmol) of 3-(4-chloro-2-fluorophenyl)-1-methyl-5-methylthio-1H-pyrazole in 400 ml of carbon tetrachloride, and the mixture was then stirred for 3 days. The reaction solution was subsequently washed with saturated aqueous sodium bicarbonate solution and water, dried over magnesium sulfate and finally concentrated. The crude product was purified by silica gel chromatography (mobile phase: hexane/ethyl acetate =9:1). Yield: 22.4 g. $^1$H-NMR (270 MHz, in CDCl$_3$): δ[ppm]=2.40 (s, 3H), 4.06 (s, 3H), 7.15–7.25 (m, 2H), 7.48 (t, 1H).

Intermediate 4.2
4-Bromo-3-(4-chloro-2-fluorophenyl)-1-methyl-5-methylsulfonyl-1H-pyrazole With ice-cooling, 31.1 g (0.18 mol) of m-chloroperbenzoic acid were added a little at a time to a solution of 22.4 g (67 mmol) of 4-bromo-3-(4-chloro-2-fluorophenyl)-1-methyl-5-methylthio-1H-pyrazole in 300 ml of dichloromethane, and the mixture was then stirred at approximately 20° C. for 16 h. The reaction solution was subsequently washed with saturated aqueous sodium bicarbonate solution, aqueous Na$_2$S$_2$O$_3$ solution and water, dried over magnesium sulfate and finally concentrated. Yield: 17.7 g. $^1$H-NMR (270 MHz, in CDCl$_3$): δ[ppm]=3.32 (s, 3H), 4.27 (s, 3H), 7.20–7.28 (m, 2H), 7.41 (t, 1H).

Intermediate 4.3
4-Bromo-3-(4-chloro-2-fluoro-5-nitrophenyl)-1-methyl-5-methyl-sulfonyl-1H-pyrazole This compound was prepared similarly to Intermediate 1.1. $^1$H-NMR (270 MHz, in CDCl$_3$): δ[ppm]=3.33 (s, 3H), 4.29 (s, 3H), 7.44 (d, 1H), 8.20 (d, 1H).

Intermediate 4.4
5-(4-Bromo-1-methyl-5-methylsulfonyl-1H-pyrazol-3-yl)-2-chloro-4-fluoroaniline This compound was prepared similarly to Intermediate 1.2. $^1$H-NMR {270 MHz, in (CD$_3$)$_2$SO}: δ[ppm]=3.47 (s, 3H), 4.17 (s, 3H), 5.43 (s, 2H), 6.88 (d, 1H), 7.34 (d, 1H).

Intermediate 4.5
5-(4-Bromo-1-methyl-5-methylsulfonyl-1H-pyrazol-3-yl)-2-chloro-4-fluorophenyl azide (No. Va.9)

This compound was prepared similarly to Intermediate 1.3. MS [m/z]: 407 [M$^+$]. $^1$H-NMR (400 MHz, in CDCl$_3$): δ[ppm]=3.32 (s, 3H), 4.28 (s, 3H), 7.28 (m, 2H).

Example 5
2-Amino-7-(4-bromo-5-difluoromethoxy-1-methyl-1H-pyrazol-3-yl)-4-chloro-6-fluorobenzothiazole (Compound No. Ic.080)

4.1 g (50 mmol) of sodium thiocyanate were added to a solution of 4.7 g (13 mmol) of 5-(4-bromo-5-difluoromethoxy-1-methyl-1H-pyrazol-3-yl)-2-chloro-4-fluoroaniline in 100 ml of acetic acid. The mixture was stirred for 10 minutes, and 4 g (25 mmol) of bromine were then added dropwise, and the mixture was subsequently stirred for 16 h. The reaction mixture was then poured into water. The resulting solid product of value was subsequently filtered off and dried. Yield: quantitative. $^1$H-NMR (270 MHz, in CDCl$_3$): δ[ppm]=3.87 (s, 3H), 6.20 (s, 2H), 6.74 (t, 1H), 7.24 (d, 1H).

Example 6
7-(4-Bromo-5-difluoromethoxy-1-methyl-1H-pyrazol-3-yl)-4-chloro-6-fluoro-2-(methylthio)benzothiazole (Compound No. Ic.099)

A solution of 1.5 g (3.5 mmol) of 2-amino-7-(4-bromo-5-difluoromethoxy-1-methyl-1H-pyrazol-3-yl)-4-chloro-6-fluoro-benzothiazole in 50 ml of dichloromethane was admixed dropwise with 0.98 g (10.5 mmol) of dimethyl disulfide and 1.08 g (7 mmol) of t-butyl nitrite. After 16 h, the solution was concentrated and the residue was purified by silica gel chromatography. Yield 0.4 g. $^1$H-NMR (270 MHz, in CDCl$_3$): δ[ppm]=2.80 (s, 3H), 3.90 (s, 3H), 6.74 (t, 1H), 7.34 (d, 1H).

Example 7
2-Bromo-7-(4-bromo-5-difluoromethoxy-1-methyl-1H-pyrazol-3-yl)-4-chloro-6-fluorobenzothiazole (Compound No. Ic.041)

A solution of 1.5 g (3.5 mmol) of 2-amino-7-(4-bromo-5-difluoro-methoxy-1-methyl-1H-pyrazol-3-yl)-4-chloro-6-fluorobenzothiazole in 50 ml of acetonitrile was admixed with 1.8 g (17.5 mmol) of sodium bromide, 1 g (7 mmol) of copper(I) bromide and 0.47 g (4.6 mmol) of t-butyl nitrite. After 16 h, the mixture was admixed with 50 ml of dil. hydrochloric acid, filtered off from the precipitate and washed with ethyl acetate. The phases of the filtrate were separated, the aqueous phase was extracted twice with ethyl acetate and the combined organic phases were dried over MgSO$_4$, filtered and concentrated. The crude product was purified by silica gel chromatography. Yield 0.4 g. MS [m/z]: 489 [M$^+$].

Example 8
7-(4-Bromo-5-difluoromethoxy-1-methyl-1H-pyrazol-3-yl)-4-chloro-6-fluoro-2-methoxybenzothiazole (Compound No. Ic.042)

60 mg (2.7 mmol) of sodium hydride were dissolved in 20 ml of methanol and then admixed with 0.4 g (1 mmol) of 2-bromo-7-(4-bromo-5-difluoromethoxy-1-methyl-1H-pyrazol-3-yl)-4-chloro-6-fluorobenzothiazole. After 1 h, the mixture was concentrated and the crude product was purified by silica gel chromatography (mobile phase cyclohexane/ethyl acetate 4:1). Yield 0.4 g. $^1$H-NMR (270 MHz, in CDCl$_3$): δ[ppm]=3.88 (s, 3 H), 4.13 (s, 3 H), 6.74 (t, 1 H), 7.29 (d, 1 H).

Use Examples (Herbicidal Activity)

The herbicidal activity of the substituted pyrazol-3-ylbenzazoles [sic] I was demonstrated by the following greenhouse experiments:

The culture containers used were plastic flowerpots with loamy sand containing approximately 3.0% of humous as substrate. The seeds of the test plants were sown separately for each species.

For the pre-emergence treatment, the active compounds, which had been suspended or emulsified in water, were applied directly after seeding using finely distributing nozzles. The containers were irrigated gently to promote germination and growth and subsequently covered with translucent plastic hoods until the plants had taken roots. This cover causes uniform germination of the test plants unless this was adversely affected by the active compounds.

For the post-emergence treatment, the test plants were initially grown to a height of 3–15 cm, depending on the habit, and only then treated with the active compounds which had been suspended or emulsified in water. To this end, the test plants were either sown directly and cultivated in the same vessels, or they were initially cultivated separately as seedlings and transplanted into the test containers a few days prior to the treatment.

The plants were kept at temperatures of 10–25° C. and 20–35° C., depending on the species. The test period extended over 2–4 weeks. During this time, the plants were tended, and their reaction to the individual treatments was evaluated.

Evaluation was carried out using a scale from 0 to 100. 100 means no emergence of the plants, or complete destruction of at least the above-ground parts, and 0 means no damage or normal course of growth.

Use Examples (Desiccant/Defoliant Activity)

The test plants used were young cotton plants having 4 leaves (without cotyledon) which were grown under greenhouse conditions (rel. atmospheric humidity 50–70%; temperature by day/by night 27/20° C.).

The leaves of the young cotton plants were treated to runoff point with aqueous preparations of the active compounds (with addition of 0.15% by weight of the fatty alcohol alkoxylate Plurafac® LF 700[1], based on the spray liquor). The amount of water applied was 1000 1/ha (converted). After 13 days, the number of leaves which had been shed and the degree of defoliation in % were determined.

[1] a low-foam nonionic surfactant from BASF AG

In the untreated control plants, no defoliation was observed.

We claim:

1. A compound of formula I

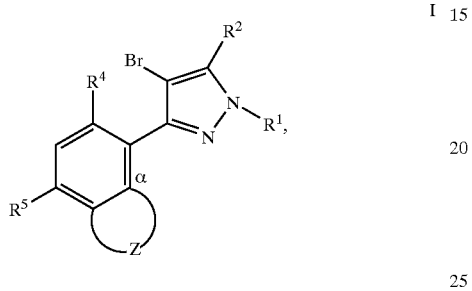

wherein $R^1$ is hydrogen, $C_1$–$C_4$-alkyl or $C_1$–$C_4$-haloalkyl;

$R^2$ is cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfinyl, $C_1$–$C_4$-haloalkylsulfinyl, $C_1$–$C_4$-alkylsulfonyl or $C_1$–$C_4$-haloalkylsulfonyl;

$R^4$ is hydrogen or halogen;

$R^5$ is hydrogen, halogen, cyano, $C_1$–$C_4$-alkyl, $C_1$–$C_4$-haloalkyl, $C_1$–$C_4$-alkoxy or $C_1$–$C_4$-haloalkoxy;

Z is a group —N=C(XR$^6$)—O— or —N=C(XR$^6$)—S— which may be attached to α via the nitrogen, oxygen or sulfur;

X is a chemical bond, oxygen, sulfur, —S(O)—, —SO$_2$—, —NH— or —N(R$^7$)—;

$R^6$, $R^7$ independently of one another are each $C_1$–$C_6$-alkyl, $C_1$–$C_6$-haloalkyl, cyano-$C_1$–$C_4$-alkyl, hydroxy-$C_1$–$C_4$-alkyl, $C_3$–$C_6$-alkenyl, cyano-$C_3$–$C_6$-alkenyl, $C_3$–$C_6$-haloalkenyl, $C_3$–$C_6$-alkynyl, cyano-$C_3$–$C_6$-alkynyl, $C_3$–$C_6$-haloalkynyl, $C_1$–$C_4$-alkoxy-$C_1$–$C_4$-alkyl, $C_1$–$C_4$-haloalkoxy-$C_1$–$C_4$-alkyl, $C_3$–$C_4$-alkenyloxy-$C_1$–$C_4$-alkyl, $C_3$–$C_4$-alkynyloxy-$C_1$–$C_4$-alkyl, $C_3$–$C_8$-cycloalkyloxy-$C_1$–$C_4$-alkyl, amino-$C_1$–$C_4$-alkyl, $C_1$–$C_4$-alkylamino-$C_1$–$C_4$-alkyl, di($C_1$–$C_4$-alkyl)amino-$C_1$–$C_4$-alkyl, $C_1$–$C_4$-alkylthio-$C_1$–$C_4$-alkyl, $C_1$–$C_4$-haloalkylthio-$C_1$–$C_4$-alkyl, $C_3$–$C_4$-alkenylthio-$C_1$–$C_4$-alkyl, $C_3$–$C_4$-alkynylthio-$C_1$–$C_4$-alkyl, $C_1$–$C_4$-alkylsulfinyl-$C_1$–$C_4$-alkyl, $C_1$–$C_4$-haloalkylsulfinyl-$C_1$–$C_4$-alkyl, $C_3$–$C_4$-alkenylsulfinyl-$C_1$–$C_4$-alkyl, $C_3$–$C_4$-alkynylsulfinyl-$C_1$–$C_4$-alkyl, $C_1$–$C_4$-alkylsulfonyl-$C_1$–$C_4$-alkyl, $C_1$–$C_4$-haloalkylsulfonyl-$C_1$–$C_4$-alkyl, $C_3$–$C_4$-alkenylsulfonyl-$C_1$–$C_4$-alkyl, $C_3$–$C_4$-alkynylsulfonyl-$C_1$–$C_4$-alkyl, hydroxycarbonyl-$C_1$–$C_4$-alkyl, ($C_1$–$C_4$-alkoxy)carbonyl-$C_1$–$C_4$-alkyl, which may carry a cyano or ($C_1$–$C_4$-alkoxy)carbonyl group, ($C_1$–$C_4$-alkylthio)carbonyl-$C_1$–$C_4$-alkyl, aminocarbonyl-$C_1$–$C_4$-alkyl, $C_1$–$C_4$-alkylaminocarbonyl-$C_1$–$C_4$-alkyl, di($C_1$–$C_4$-alkyl)aminocarbonyl-$C_1$–$C_4$-alkyl, di($C_1$–$C_4$-alkyl)phosphonyl-$C_1$–$C_4$-alkyl, ($C_1$–$C_4$-alkoxy)imino-$C_1$–$C_4$-alkyl, ($C_3$–$C_4$-alkenyloxy)imino-$C_1$–$C_4$-alkyl, $C_3$–$C_8$-cycloalkyl, $C_3$–$C_8$-cycloalkyl-$C_1$–$C_4$-alkyl, phenyl, phenyl-$C_1$–$C_4$-alkyl, 3- to 7-membered heterocyclyl or heterocyclyl-$C_1$–$C_4$-alkyl, where each cycloalkyl and each heterocyclyl ring may contain a carbonyl or thiocarbonyl ring member, and where each cycloalkyl, phenyl and heterocyclyl ring may be unsubstituted or may carry from one to four substituents, in each case selected from the group consisting of cyano, nitro, amino, hydroxyl, carboxyl, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl, ($C_1$–$C_4$-alkoxy)carbonyl, ($C_1$–$C_4$-alkyl)carbonyl, ($C_1$–$C_4$-haloalkyl)carbonyl, ($C_1$–$C_4$-alkyl)carbonyloxy, ($C_1$–$C_4$-haloalkyl)carbonyloxy and di($C_1$–$C_4$-alkyl)amino;

if X is a chemical bond, oxygen, sulfur, —NH— or —N(R$^7$)—, $R^6$ may also be ($C_1$–$C_4$-alkyl)carbonyl, ($C_1$–$C_4$-haloalkyl)carbonyl, ($C_1$–$C_4$-alkoxy)carbonyl, $C_1$–$C_4$-alkylsulfonyl or $C_1$–$C_4$-haloalkylsulfonyl;

if X is a chemical bond, $R^6$ may furthermore be hydrogen, cyano, mercapto, amino, halogen, —CH$_2$—CH(halogen)-$R^8$, —CH=CH—$R^8$ or —CH=C(halogen)-$R^8$, where $R^8$ is hydroxycarbonyl, ($C_1$–$C_4$-alkoxy)carbonyl, ($C_1$–$C_4$-alkylthio)carbonyl, aminocarbonyl, $C_1$–$C_4$-alkylaminocarbonyl, di($C_1$–$C_4$-alkyl)aminocarbonyl or di($C_1$–$C_4$-alkyl)phosphonyl;

or $R^6$ and $R^7$ together are a 1,3-propylene, tetramethylene, pentamethylene or ethyleneoxyethylene chain which may in each case be unsubstituted or may carry from 1 to 4 $C_1$–$C_4$-alkyl groups or one or two ($C_1$–$C_4$-alkoxy)carbonyl groups, or an agriculturally useful salt thereof.

2. A herbicidal composition, comprising an effective amount of at least one compound of formula I defined in claim 1 or the salt thereof, and at least one inert liquid or solid carrier and optionally at least one surfactant.

3. A composition for the desiccation or defoliation of plants, comprising an effective amount of at least one compound of formula I defined in claim 1 or the salt thereof, and at least one inert liquid or solid carrier and optionally at least one surfactant.

4. A process for preparing a herbicidal composition, which comprises mixing an effective amount of at least one compound of formula I defined in claim 1 or the salt thereof with at least one inert liquid or solid carrier and optionally at least one surfactant.

5. A process for preparing a composition having desiccant or defoliant action, which comprises mixing an effective amount of at least one compound of formula I defined in claim 1 or the salt thereof with at least one inert liquid or solid carrier and optionally at least one surfactant.

6. A method for controlling undesirable vegetation, which comprises allowing an effective amount of at least one substituted compound of formula I defined in claim 1 or the salt thereof, to act on the plants, their habitat or on seeds.

7. A method for the desiccation or defoliation of plants, which comprises allowing an effective amount of at least one compound of formula I defined in claim 1 or the salt thereof, to act on the plants.

8. The process of claim 7, wherein the plants are cotton plants.

9. A process for preparing the compound of formula I defined in claim 1 in which Z is —N=C(R$^6$)—O—, which comprises diazotizing an aminophenylpyrazole compound of formula IIIa or IIIb,

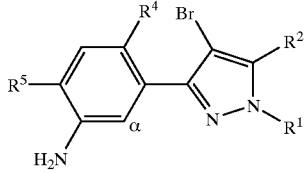

IIIa

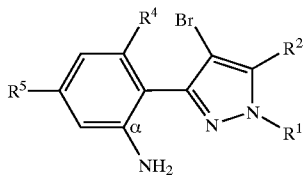

IIIb reacting the resulting diazonium salt with an alkali metal azide to give an azidophenylpyrazole compound of formula Va or Vb

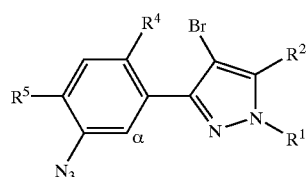

Va

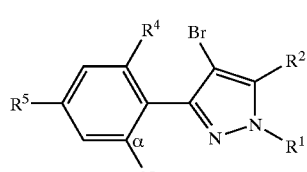

Vb and reacting the compound of formula Va or Vb with a carboxylic acid $R^6$—COOH.

10. An azidophenylpyrazole compound of formula Va or Vb

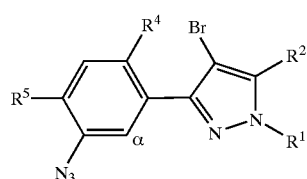

Va

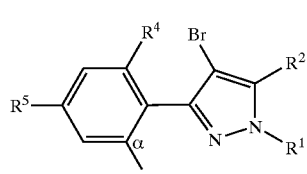

Vb wherein $R^1$ is hydrogen, $C_1$–$C_4$-alkyl or $C_1$–$C_4$-haloalkyl;

$R^2$ is cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfinyl, $C_1$–$C_4$-haloalkylsulfinyl, $C_1$–$C_4$-alkylsulfonyl or $C_1$–$C_4$-haloalkylsulfonyl;

$R^4$ is hydrogen or halogen; and $R^5$ is hydrogen, halogen, cyano, $C_1$–$C_4$-alkyl, $C_1$–$C_4$-haloalkyl, $C_1$–$C_4$-alkoxy or $C_1$–$C_4$-haloalkoxy.

11. The compound bf formula Va or Vb defined in claim 10, wherein $R^1$ is $C_1$–$C_4$-alkyl;

$R^2$ is $C_1$–$C_4$-haloalkoxy or $C_1$–$C_4$-alkylsulfonyl; and $R^5$ is halogen.

12. The compound of formula I defined in claim 1, wherein $R^1$ is $C_1$–$C_4$-alkyl;

$R^2$ is $C_1$–$C_4$-haloalkoxy or $C_1$–$C_4$-alkylsulfonyl; and $R^5$ is halogen.

13. The compound of formula I defined in claim 12, wherein x is a chemical bond, oxygen or sulfur.

14. The compound of formula I defined in claim 13, wherein $R^6$ is $C_1$–$C_6$-alkyl, $C_3$–$C_6$-alkenyl, $C_3$–$C_6$-alkynyl, $C_1$–$C_4$-alkoxy- $C_1$–$C_4$-alkyl, ($C_1$–$C_4$-alkoxy)carbonyl-$C_1$–$C_4$-alkyl, $C_3$–$C_8$-cycloalkyl, phenyl, phenyl-$C_1$–$C_4$-alkyl or 3- to 7-membered heterocycly, where each cycloalkyl and each heterocyclyl ring may contain a carbonyl or thiocarbonyl ring member, wherein the cycloalkyl, the phenyl and the heterocyclyl ring is unsubstituted or carries from one to four substituents selected from the group consisting of: cyano, nitro, amino, hydroxyl, carboxyl, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl, ($C_1$–$C_4$-alkoxy)carbonyl, ($C_1$–$C_4$-alkyl)carbonyl, ($C_1$–$C_4$-haloalkyl)carbonyl, ($C_1$–$C_4$-alkyl)carbonyloxy, ($C_1$–$C_4$-haloalkyl)carbonyloxy and di($C_1$–$C_4$-alkyl) amino; or $R^6$ is amino or halogen when X is a chemical bond.

15. The compound of formula I defined in claim 1, wherein $R^6$ is $C_1$–$C_6$-alkyl, $C_3$–$C_6$-alkenyl, $C_3$–$C_6$-alkynyl, $C_1$–$C_4$-alkoxy- $C_1$–$C_4$-alkyl, ($C_1$–$C_4$-alkoxy)carbonyl-$C_1$–$C_4$-alkyl, $C_3$–$C_8$-cycloalkyl, phenyl, phenyl-$C_1$–$C_4$-alkyl or 3- to 7-membered heterocycly, where each cycloalkyl and each heterocyclyl ring may contain a carbonyl or thiocarbonyl ring member, wherein the cycloalkyl, the phenyl and the heterocyclyl ring is unsubstituted or carries from one to four substituents selected from the group consisting of: cyano, nitro, amino, hydroxyl, carboxyl, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl, ($C_1$–$C_4$-alkoxy)carbonyl, ($C_1$–$C_4$-alkyl)carbonyl, ($C_1$–$C_4$-haloalkyl)carbonyl, ($C_1$–$C_4$-alkyl)carbonyloxy, ($C_1$–$C_4$-haloalkyl)carbonyloxy and di($C_1$–$C_4$-alkyl) amino; or $R^6$ is amino or halogen when X is a chemical bond.

16. The compound of formula I defined in claim 1, wherein $R^6$ is $C_1$–$C_6$-alkyl, $C_3$–$C_6$-alkenyl, $C_3$–$C_6$-alkynyl, $C_1$–$C_4$-alkoxy-$C_1$–$C_4$-alkyl, ($C_1$–$C_4$-alkoxy)carbonyl-$C_1$–$C_4$-alkyl, $C_3$–$C_8$-cycloalkyl, phenyl, phenyl-$C_1$–$C_4$-alkyl or 3- to 7-membered heterocycly, where each cycloalkyl and each heterocyclyl ring may contain a carbonyl or thiocarbonyl ring member, wherein the cycloalkyl, the phenyl and the heterocyclyl ring is unsubstituted or carries from one to four substituents selected from the group consisting of: cyano, nitro, amino, hydroxyl, carboxyl, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl, ($C_1$–$C_4$-alkoxy)carbonyl, ($C_1$–$C_4$-alkyl)carbonyl, ($C_1$–$C_4$-haloalkyl)carbonyl, ($C_1$–$C_4$-alkyl)carbonyloxy, ($C_1$–$C_4$-haloalkyl)carbonyloxy and di($C_1$–$C_4$-alkyl)amino; or $R^6$ is amino or halogen when X is a chemical bond.

17. The compound of formula I defined in claim 1, wherein X is a chemical bond, oxygen or sulfur.

* * * * *

UNITED STATES PATENT AND TRADEMARK OFFICE
CERTIFICATE OF CORRECTION

PATENT NO.    : 6,482,774 B1
DATED         : November 19, 2002
INVENTOR(S)   : Zagar et al.

It is certified that error appears in the above-identified patent and that said Letters Patent is hereby corrected as shown below:

Title page,
Item [57], ABSTRACT,
After formula I, Line 3, "$C_I$-$C_4$-" should be -- $C_1$-$C_4$- --;
Line 15, "$C_I$-$C_6$-alkyl, $C_I$-$C_6$-haloalkyl, cyano-$C_I$-$C_4$-" should be
-- $C_1$-$C_6$-alkyl, $C_1$-$C_6$-haloalkyl, cyano-$C_1$-$C_6$- --;
Lines 22, 23 and 26, "$C_I$-$C_4$-" should be -- $C_1$-$C_4$- --;

Column 52,
Line 4, "bf formula" should be -- of formula --.

Signed and Sealed this

Eighteenth Day of February, 2003

JAMES E. ROGAN
*Director of the United States Patent and Trademark Office*